(12) United States Patent
Krivokrysenko et al.

(10) Patent No.: US 10,183,056 B2
(45) Date of Patent: Jan. 22, 2019

(54) METHODS AND COMPOSITIONS FOR THE TREATMENT OF RADIATION-RELATED DISORDERS

(71) Applicant: CLEVELAND BIOLABS, INC., Buffalo, NY (US)

(72) Inventors: Vadim Krivokrysenko, Buffalo, NY (US); Elena Feinstein, Buffalo, NY (US)

(73) Assignee: CLEVELAND BIOLABS, INC., Buffalo, NY (US)

( * ) Notice: Subject to any disclaimer, the term of this patent is extended or adjusted under 35 U.S.C. 154(b) by 0 days.

(21) Appl. No.: 15/519,462

(22) PCT Filed: Oct. 16, 2015

(86) PCT No.: PCT/US2015/055986
§ 371 (c)(1),
(2) Date: Apr. 14, 2017

(87) PCT Pub. No.: WO2016/109002
PCT Pub. Date: Jul. 7, 2016

(65) Prior Publication Data
US 2017/0239326 A1    Aug. 24, 2017

Related U.S. Application Data

(60) Provisional application No. 62/214,572, filed on Sep. 4, 2015, provisional application No. 62/064,872, filed on Oct. 16, 2014.

(51) Int. Cl.
*A61K 38/16* (2006.01)
*A61K 45/06* (2006.01)
*C07K 14/195* (2006.01)
*C07K 14/255* (2006.01)
*A61K 9/00* (2006.01)
*C07K 14/705* (2006.01)

(52) U.S. Cl.
CPC .......... *A61K 38/164* (2013.01); *A61K 9/0019* (2013.01); *A61K 45/06* (2013.01); *C07K 14/195* (2013.01); *C07K 14/255* (2013.01); *C07K 14/705* (2013.01)

(58) Field of Classification Search
CPC ...... A61K 2300/00; A61K 2039/55561; A61K 38/00; A61K 2039/55594; A61K 38/164; C07K 14/00; C07K 14/255; C07K 14/195
See application file for complete search history.

(56) References Cited

U.S. PATENT DOCUMENTS

| | | | |
|---|---|---|---|
| 4,554,101 A | 11/1985 | Hopp | |
| 5,399,494 A | 3/1995 | Kaper et al. | |
| 5,693,476 A | 12/1997 | Scheller | |
| 6,130,082 A | 10/2000 | Majarian et al. | |
| 7,404,963 B2 | 7/2008 | Sotomayor et al. | |
| 7,638,485 B2 | 12/2009 | Gudkov | |
| 7,794,731 B2 | 9/2010 | Mizel et al. | |
| 8,007,812 B2 | 8/2011 | Gudkov et al. | |
| 8,106,005 B2 | 1/2012 | Gudkov | |
| 8,287,882 B2 | 10/2012 | Gudkov et al. | |
| 8,324,163 B2 | 12/2012 | Gudkov et al. | |
| 8,580,321 B2 | 11/2013 | Gudkov et al. | |
| 2002/0009747 A1 | 1/2002 | Miller et al. | |
| 2003/0044429 A1 | 3/2003 | Aderem et al. | |
| 2005/0147627 A1 | 7/2005 | Aderem et al. | |
| 2005/0266391 A1 | 12/2005 | Bennett et al. | |
| 2006/0275255 A1 | 12/2006 | Gudkov | |
| 2007/0202551 A1 | 8/2007 | Gudkov | |
| 2007/0269406 A1 | 11/2007 | Ichim | |
| 2008/0124361 A1 | 5/2008 | Mizel et al. | |
| 2008/0182797 A1 | 7/2008 | Nudler et al. | |
| 2009/0011982 A1 | 1/2009 | Gudkov et al. | |
| 2009/0081157 A1 | 3/2009 | Kornbluth et al. | |
| 2009/0123467 A1 | 5/2009 | Bedi et al. | |
| 2009/0175880 A1 | 7/2009 | Keler et al. | |
| 2009/0246303 A1 | 10/2009 | Gudkov et al. | |
| 2010/0056454 A1 | 3/2010 | Gudkov | |
| 2011/0319595 A1 | 12/2011 | Gudkov et al. | |
| 2013/0004515 A1 | 1/2013 | Gudkov et al. | |
| 2013/0324462 A1 | 12/2013 | Gudkov et al. | |

FOREIGN PATENT DOCUMENTS

| | | |
|---|---|---|
| WO | 1992005816 | 4/1992 |
| WO | 1993018150 | 9/1993 |
| WO | 1999029312 | 6/1999 |
| WO | 2001040280 | 6/2001 |

(Continued)

OTHER PUBLICATIONS

Krivokrysenko et al. Identification of granulocyte colony-stimulating factor and interleukin-6 as candidate biomarkers of CBLB502 efficacy as a medical radiation countermeasure. J Pharmacol Exp Therapeutics 342(2): 497-508, 2015.*

Krivokrysenko et al. The toll-like receptor 5 agonist entolimod mitigages lethal acute radiation syndrome in non-human primates. PLoS One 10(9): e0135388, 2015.*

Krivokrysenko, et al., "Identification of Granulocyte Colony-Stimulating Factor and Interleukin-6 as Candidate Biomarkers of CBLB502 Efficacy as a Medical Radiation Countermeasure", The Journal of Pharmacology and Experimental Therapeutics, 2010, vol. 343, No. 2, pp. 497-508.

International Search Report and Written Opinion for International Application No. PCT/US2015/055986, dated Jul. 14, 2016, 8 pages.

Pashenkov et al. "Phase II trial of a toll-like receptor 9-activating oligonucleotide in patients with metastic melanoma" J Clin Oncol 24: 5716-5724 2006.

(Continued)

*Primary Examiner* — Bridget E Bunner
(74) *Attorney, Agent, or Firm* — Morgan, Lewis & Bockius LLP

(57) ABSTRACT

This invention relates, in part, to methods and compositions that are useful for the treatment and/or prevention of various disorders, including radiation-related disorders, such as acute radiation syndrome.

13 Claims, 17 Drawing Sheets
(8 of 17 Drawing Sheet(s) Filed in Color)
Specification includes a Sequence Listing.

(56) References Cited

FOREIGN PATENT DOCUMENTS

| | | |
|---|---|---|
| WO | 2001055210 | 8/2001 |
| WO | 2002044363 | 6/2002 |
| WO | 2003027251 | 4/2003 |
| WO | 2003028659 | 4/2003 |
| WO | 2004086039 | 10/2004 |
| WO | 2005056041 | 6/2005 |
| WO | 2005056042 | 6/2005 |
| WO | 2005056054 | 6/2005 |
| WO | 2005056055 | 6/2005 |
| WO | 2005057218 | 6/2005 |
| WO | 2006066214 | 6/2006 |
| WO | 2006069198 | 6/2006 |
| WO | 2007030581 | 3/2007 |
| WO | 2008157473 | 12/2008 |
| WO | 2009102818 | 8/2009 |
| WO | 2010040096 | 4/2010 |
| WO | 2010133885 | 11/2010 |
| WO | 2011027222 | 3/2011 |
| WO | 2011044246 | 4/2011 |
| WO | WO 2013151994 A1 | 10/2013 |
| WO | WO 2014098649 A1 | 6/2014 |
| WO | 2014145314 A2 | 9/2014 |

OTHER PUBLICATIONS

Patchen M. L. "Amifostine plus granulocyte colony-stimulating factor therapy enhances recovery from supralethal radiation exposures: preclinical experience in animals models" European Journal of Cancer 31A(1):S17-S21 (1995).
Rensing-Ehl et al., Local Fas/APO-1 (CD95) Ligand-Mediated Tumor Cell Killing in vivo, Eur J Immunol, 1995, vol. 25, pp. 2253-2258.
Rhee et al. "Toll-like receptor 5 engagement modulates tumor development and growth in a mouse xenograft model of human colon cancer" Gastroenterology Aug. 2008; 135(2): 518-528.
Samatey F. A. et al. "Structure of the bacterial flagellar protofilament and implications for a switch for supercoiling" Nature 410:331-337 (2001).
Satyamitra M. et al. "In vivo postirradiation protection by a vitamin E analog a-TMG" Radiation Research 160 (6):655-661 (2003).
Schmidt et al. "Intratumoural injection of the toll-like receptor-2/6 agonist 'macrophage-activating lipopeptide-2' in patients with pancreatic carcinoma: a phase I/II trial" Brit J Cancer 97: 598-604 2007.
Sebastiani G. et. al. "Cloning and characterization of the murine Toll-like Receptor 5 (Tlr5) gene: sequence and mRNA expression studies in *Salmonella*-susceptible MOLF/Ei mice" Genomics 64(3):230-240 (2000).
Seed T. et al. "New strategies for the prevention of radiation injury: possible implications for countering radiation hazards of long-term space travel" Journal of Radiation Research 43:S239-S244 (2002).
Selander R. K. et al. "Molecular evolutionary genetics of the cattle-adapted serovar *Salmonella dublin*" Journal of Bacteriology 174(11):3587-3592 (1992).
Service R. F. "Tumor-Killer Made; How Does It Work?" Science 274:2009 (1996).
Sfondrini et al. "Antitumor Activity of the TLR-5 Ligand Flagellin in Mouse Models of Cancer" The Journal of Immunology 2006 176:6624-6630.
Smith K. D. et al. "Toll-like receptor 5 recognizes a conserved site on flagellin required for protofilament formation and bacterial motility" Nature Immunology 4(12):1247-1253 (2003).
Song et al. "Flagellin promotes the proliferation of gastric cancers via the Toll-like receptor 5" Int J Mol Med 28:115-119 2011.
Spadaro J. A. et al. "Radioprotectant combinations spare radiation-induced damage to the physis more than fractionation alone" Int. J. Radiat. Biol. 81(10):759-765 (2005) Abstract.
Sredni B. et al. "The immunomodulator AS101 administered orally as a chemoprotective and radioprotective agent" Int. J. Immunopharmacol. 14(4):613-619 (1992).
Streeter P. R. et al. "Activation of the G-CSF and Flt-3 receptors protects hematopoietic stem cells from lethal irradiation" Experimental Hematology 31(11):1119-1125 (2003).
Symon Z. et al. "Selective radioprotection of hepatocytes by systemic and portal vein infusions of amifostine in a rat liver tumor model" Int. J. Radiation Oncology Biol. Phys. 50(2):473-478 (2001).
Tallant T. et al. "Flagellin acting via TLR5 is the major activator of key signaling pathways leading to NF-KB and proinflammatory gene program activation in intestinal epithelial cells" BMC Microbiology 4(1):33 (2004).
Timmer et al. "Fas receptor-mediated apoptosis: a clinical application?" J Pathol 196: 125-134 2002.
Trauth et al. "Monoclonal antibody-mediated tumor regression by induction of apoptosis" Science 245: 301-305 1989.
Tsujimoto H. et al. "Flagellin enhances NK cell proliferation and activation directly and through dendritic cell—NK cell Interactions" Journal of Leukocyte Biology 78(4):888-897 (2005).
Vasquez R. J. et al. "Nanomolar concentrations of nocodazole alter microtubule dynamic instability in vivo and in vitro" Molecular Biology of the Cell 8(6):973-985 (1997).
Vijay-Kumar et al. "Flagellin Treatment Protects against Chemicals Bacteria Viruses and Radiation" The Journal of Immunology 2008 180:8280-8285.
Waddick K. G. et al. "In vitro and in vivo antileukemic activity of B43-pokeweed antiviral protein against radiation-resistant human B-cell precursor leukemia cells" Blood 86(11):4228-4233 (1995).
Watson A. J. et al. "Lessons from genetically engineered animal models. VII. Apoptosis in intestinal epithelium: lessons from transgenic and knockout mice" Am. J. Physiol. Gastrointest. Liver Physiol. 278(1):G1-G5 (2000).
Wheeler C. M. "Preventative vaccines for cervial cancer" Salud Publica de Mexico 39(4) (1997) 9 pages.
Whitnall M. H. et al. "In vivo radioprotection by 5-androstenediol: stimulation of the innate immune system" Radiation Research 156(3):283-293 (2001).
Wolska et al. "Toll-like receptors and their role in carcinogensis and anti-tumor treatment" Cell Mol Biol Letters 14:248-272 2009.
Wong G. H. W. "Protective roles of cytokines against radiation: induction of mitochondrial MnSOD" Biochimica et Biophysica Acta 1271:205-209 (1995).
Yang et al. "Antigen replacement of domains D2 and D3 in flagellin promotes mucosal IgA production and attenuates flagellin-induced inflammatory response after intranasal immunization" Human Vaccines and Immunotherap 9:5 1084-1092 2013.
Leigh et al. "A Flagellin-Derived Toll-Like Receptor 5 Agonist Stimulates Cytotoxic Lymphocyte-Mediated Tumor Immunity" PLOS ONE Jan. 2014 vol. 9 Issue 1 pp. 1-10.
Alavanja M. CR. "Biologic damage resulting from exposure to tobacco smoke from radon: implication for preventive interventions" Oncogene 21:7365-7375 (2002).
Andreassen C. N. et al. "Chemical radioprotection: a critical review of amifostine as a cytoprotector in radiotherapy" Seminars in Radiation Oncology 13(1):62-72 (2003).
Androstenediol and Androstenedione Wikipedia (online). URL: < http://en. wikipedia.org/wiki/Androstenediol> [Retrieved from the Internet: Dec. 5, 2006] 4 pages.
Bachmann M. F. et al. "Recall proliferation potential of memory CD8+ T cells and antiviral protection" The Journal of Immunology 175:4677-4685 (2005).
Ben-Yedidia T. et al. "Intranasal administration of peptide vaccine protects human/mouse radiation chimera from influenza infection" International Immunology 11(7):1043-1051 (1998).
Booth D. et. al. "Transforming growth factor-B3 protects murine small intestinal crypt stem cells and animal survival after irradiation possibly by reducing stem-cell cycling" Int. J. Cancer 86(1):53-59 (2000).
Borges H. L. et al. "DNA damage-induced cell death: lessons from the central nervous system" Cell Research 18:17-26 (2008).
Bulinski J. C. et al. "Overexpression of MAP4 inhibits organelle motility and trafficking in vivo" Journal of Cell Sciences 110:3055-3064 (1997).

(56) References Cited

OTHER PUBLICATIONS

Burdelya L. G. et al. "An agonist of toll-like receptor 5 has radioprotective activity in mouse and primate models" Science 320:226-230 (2008).
Cai et al. "Activation of toll-like receptor 5 on breast cancer cells by flagellin suppresses cell proliferation and tumor growth" Cancer Res 71 (7): 2466-2475 2011.
Cai et al. "Activation of toll-like receptor 5 on breast cancer cells by flagellin suppresses tumor development and growth" Cancer Res 70: #3819 Apr. 2010.
Carnes B. A. et al. "Mortality of atomic bomb survivors predicted from laboratory animals" Radiation Research 160 (2):159-167 (2003) Abstract.
Caron G. et. al. "Direct stimulation of human T cells via TLR5 and TLR7/8: Flagellin and R-848 up-regulate proliferation and IFN-y production by memory CD4+ T cells" The Journal of Immunology 175(3):1551-1557 (2005).
Coffman et al. Vaccine Adjuvants: Pulling Innate Immunity to Work Immunity vol. 33 Oct. 29, 2010 pp. 492-503.
Dummer et al. "An exploratory study of systemic administration of the toll-like receptor-7 agonist 852A in patients with refractory metastatic melanoma" Clin Cancer Res 14(3): 856-864 2008.
Eaves-Pyles T. D. et al. "*Salmonella flagellin*-dependent proinflammatory responses are localized to the conserved amino and carboxyl regions of the protein" The Journal of Immunology 167(12):7009-7016 (2001).
Eaves-Pyles T. et al. "Flagellin a novel mediator of *Salmonella*-induced epithelial activation and systemic inflammation: IKBa degradation induction of nitric oxide synthase induction of proinflammatory mediators and cardiovascular dysfunction" The Journal of Immunology 166(2):1248-1260 (2001).
Efferson C. L. et al. "Stimulation of human T cells by an influenza A vector expressing a CTL epitope from the HER-2/neu protooncogene results in higher numbers of antigen-specific TCRhi cells than stimulation with peptide. Divergent roles of IL-2 and IL-15" Anticancer Research 25:715-724 (2005).
Egan L. J. et al. "IkB-kinase13-dependent NF-k13 activation provides radioprotection to the intestinal epithelium" PNAS 101(8):2452-2457 (2004).
Elewaut D. et al. "NF-KB is a central regulator of the intestinal epithelial cell innate immune response induced by infection with enteroinvasive bacteria" The Journal of Immunology 163:1457-1466 (1999).
Etter et al. "The combination of chemotherapy and intraperitoneal MegaFas ligand improves treatment of ovarian carcinoma" Gynecologic Oncol 107: 14-21 2007.
Foldes G. et al. "Toll-like receptor modulation in cardiovascular disease: a target for intervention?" Expert Opinion on Investigational Drugs 15(8):857-871 (2006).
Fukuzawa N. et al. "A TLR5 agonist inhibits acute renal ischemic failure" The Journal of Immunology 187:3831-3839 (2011).
GenBank databases NCBI Accession No. M84972 Apr. 26, 1993 [online] [retrieved on Sep. 29, 2011] Retrieved from the Internet: <URL: http://www.ncbi.nlm.nih.gov/nuccore/M84972>.
Gewirtz A.T. et. al. "Cutting edge: Bacterial flagellin activates basolaterally expressed TLR5 to induce epithelial proinflammatory gene expression" The Journal of Immunology 167(4):1882-1885 (2001).
Grdina D. J. et al. "Relationships between cytoprotection and mutation prevention by WR-1065" Military Medicine 167(2):51-53 (2002).
Guan K. L. et al. "Eukaryotic proteins expressed in *Escherichia coli*: an improved thrombin cleavage and purification procedure of fusion proteins with glutathione S-transferase" Analytical Biochemistry 192:262-267 (1991).
Gudkov A. V. et al. "The role of p53 in determining sensitivity to radiotherapy" Nat. Rev. Cancer 3:117-129 (2003).
Guicciardi et al., Life and Death by Death Receptors, FASEB J, 2009, vol. 23, No. 6, pp. 1625-1637.

Haimovitz-Friedman A. et al. "Ionizing radiation acts on cellular membranes to generate ceramide and apoptosis" J. Exp. Med. 180:525-535 (1994).
Hall "Physics and Chemisty of Radiation Absorption" Radiobiology for the Radiobiologist pp. 5-15 5th ed. Lippincott Williams and Wilkins Philadelphia PA (2000).
Herbert J. M. et al. "Involvement of u-PA in the anti-apoptotic activity of TGF-beta for vascular smooth muscle cells" FEBS Letters 413(3):401-404 (1997).
Honko A. N. et al. "Effects of flagellin on innate and adaptive immunity" Immunologic Research 33(1):83-101 (2005).
Jung C. W. et al. "Antiproliferative effect of a vitamin D3 analog EB1089 on HL-60 cells by the induction of TGF-beta receptor" Leukemia Research 23(12):1105-1112 (1999).
Kemp G. et al. "Amifostine pretreatment for protection against cyclophosphamide-induced and cisplatininduced toxicities: results of a randomized control in patients with advanced ovarian cancer" Journal of Clinical Oncolouv 14(7):2101-2112 (1996).
Krieg A.M. "Development of TLR9 agonists for cancer therapy" J Clinical Invest 117(5): 1184-1194 2007.
Kyte J. et al. "A simple method for displaying the hydropathic character of a protein" J. Mol. Biol. 157:105-132 (1982).
Lehnert B. E. et al. "A new mechanism for DNA alterations induced by alpha particles such as those emitted by radon and radon progeny" Environmental Health Perspectives 105(5):1095-1101 (1997).
Li G. et al. "A special issue on DNA damage responses and genome maintenance" Cell Research 18(1):1-2 (2008).
Li J. et al."Evolutionary origin and radiation of the avian-adapted non-motile salmonellae" Journal of Medical Microbiology 38(2):129-139 (1993).
McQuiston J. R. et al. "Sequencing and comparative analysis of flagellin genes fliC fljB and flpA from *Salmonella*" Journal of Clinical Microbiology 42(5):1923-1932 (2004).
Melby T. E. et al. "The symmetrical structure of structural maintenance of chromosomes (SMC) and MukB proteins: Long antiparallel coiled coils folded at a flexible hinge" The Journal of Cell Biology 142(6):1595-1604 (1998).
Mercurio F. et al. "NF-kB as a primary regulator of the stress response" Oncogene 18:6163-6171 (1999).
Murley J. S. et al. "Delayed cytoprotection after enhancement of Sod2 (MnSOD) gene expression in SA-NH mouse sarcoma cells exposed to WR-1065 the active metabolite of amifostine" Radiation Research 158(1):101-109 (2002).
Murley J. S. et al. "Delayed radioprotection by NFKB-mediated induction of Sod2 (MnSOD) in SA-NH tumor cells after exposure to clinically used thiol-containing drugs" Radiation Research 162(5):536-546 (2004).
Mutlu-Turkoglu U. et al. "The effect of selenium and/or vitamin E treatments on radiation-induced intestinal injury in rats" Life Sciences 66(20):1905-1913 (2000).
Neish A. S. "TLRS in the Gut. II. Flagellin-induced inflammation and antiapoptosis" American Journal of Physiology: Gastrointestinal and Liver Physiology 292(2):G462-G466 (2006).
Newton S. M. C. et al. "Immune response to cholera toxin epitope inserted in *Salmonella flagellin*" Science 244:70-72 (1989).
Offringa "Tumour immunology—Exploitation of the weapon of immune destruction for cancer therapy: taking aim before firing" Current Opinion in Immunology 2005 17:159-162.
Panda D. et al. "Stabilization of microtubule dynamics by estramustine by binding to a novel site in tubulin: A possible mechanistic basis for its antitumor action" Proc. Natl. Acad. Sci. USA 94(20):10560-10564 (1997).
Burdelya, et al., "Toll-like receptor 5 agonist protects mice from dermatitis and oral mucositis caused by local radiation: Implications for head-and-neck cancer radiotherapy," International Journal of Radiation Oncology Biology Physics, vol. 83, No. 1, pp. 228-234 (May 1, 2012).
Burdelya, et al., "Central role of liver in anticancer and radioprotective activities of Toll-like receptor 5 agonist," Proceedings of the National Academy of Sciences, vol. 110, No. 20, pp. E1857-E1866 (Apr. 29, 2013).
Chow, et al., "Developmental toxicity study of CBLB502 in Wistar rats," Reproductive Toxicology, vol. 46, pp. 12-19 (2014).

(56) References Cited

OTHER PUBLICATIONS

Lei, et al., Radioprotection activity of toll-like receptor 5 agonist CBLB502 protein,: Journal of International Pharmaceutical Research, vol. 39, No. 3, pp. 225-231 (2012).

Li, et al., "CBLB502, an agonist of Toll-like receptor 5, has antioxidant and scavenging free radicals activities in vitro," International Journal of Biological Macromolecules, vol. 82, pp. 97-103 (Oct. 22, 2015).

Wang, et al., "Toll-like receptor 5 agonism protects mice from radiation pneumonitis and pulmonary fibrosis," Database Medline (Online), US National Library of Medicine, Database accession No. NLM23167416 (2012).

* cited by examiner

FIG. 1

Met Arg Gly Ser His His His His His His Gly Met Ala Ser Met Thr Gly Gly Gln Gln Met Gly
Arg Asp Leu Tyr Asp Asp Asp Lys Asp Pro Met Ala Gln Val Ile Asn Thr Asn Ser Leu
Ser Leu Leu Thr Gln Asn Asn Leu Asn Lys Ser Gln Ser Ser Leu Ser Ser Ala Ile Glu Arg
Leu Ser Ser Gly Leu Arg Ile Asn Ser Ala Lys Asp Asp Ala Ala Gly Gln Ala Ile Ala Asn Arg
Phe Thr Ser Asn Ile Lys Gly Leu Thr Gln Ala Ser Arg Asn Ala Asn Asp Gly Ile Ser Ile Ala
Gln Thr Thr Glu Gly Ala Leu Asn Glu Ile Asn Asn Asn Leu Gln Arg Val Arg Glu Leu Ser
Val Gln Ala Thr Asn Gly Thr Asn Ser Asp Ser Asp Leu Lys Ser Ile Gln Asp Glu Ile Gln Gln
Arg Leu Glu Glu Ile Asp Arg Val Ser Asn Gln Thr Gln Phe Asn Gly Val Lys Val Leu Ser
Gln Asp Asn Gln Met Lys Ile Gln Val Gly Ala Asn Asp Gly Glu Thr Ile Thr Ile Asp Leu Gln
Lys Ile Asp Val Lys Ser Leu Gly Leu Asp Gly Phe Asn Val Asn Ser Pro Gly Ile Ser Gly Gly
Gly Gly Gly Ile Leu Asp Ser Met Gly Thr Leu Ile Asn Glu Asp Ala Ala Ala Ala Lys Lys Ser
Thr Ala Asn Pro Leu Ala Ser Ile Asp Ser Ala Leu Ser Lys Val Asp Ala Val Arg Ser Ser Leu
Gly Ala Ile Gln Asn Arg Phe Asp Ser Ala Ile Thr Asn Leu Gly Asn Thr Val Thr Asn Leu
Asn Ser Ala Arg Ser Arg Ile Glu Asp Ala Asp Tyr Ala Thr Glu Val Ser Asn Met Ser Lys Ala
Gln Ile Leu Gln Gln Ala Gly Thr Ser Val Leu Ala Gln Ala Asn Gln Val Pro Gln Asn Val Leu
Ser Leu Leu Arg.

SEQ ID NO: 1

SEQUENCE LISTING

```
<160> NUMBER OF SEQ ID NOS: 1

<210> SEQ ID NO 1
<211> LENGTH: 329
<212> TYPE: PRT
<213> ORGANISM: Artificial Sequence
<220> FEATURE:
<223> OTHER INFORMATION: Synthetic polymer

<400> SEQUENCE: 1

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Ala Gln Val Ile Asn Thr Asn Ser Leu Ser Leu Leu Thr Gln
            35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175
```

```
Met Lys Ile Gln Val Gly Ala Asn Asp Gly Glu Thr Ile Thr Ile Asp
            180                 185                 190

Leu Gln Lys Ile Asp Val Lys Ser Leu Gly Leu Asp Gly Phe Asn Val
        195                 200                 205

Asn Ser Pro Gly Ile Ser Gly Gly Gly Gly Ile Leu Asp Ser Met
    210                 215                 220

Gly Thr Leu Ile Asn Glu Asp Ala Ala Ala Lys Lys Ser Thr Ala
225                 230                 235                 240

Asn Pro Leu Ala Ser Ile Asp Ser Ala Leu Ser Lys Val Asp Ala Val
            245                 250                 255

Arg Ser Ser Leu Gly Ala Ile Gln Asn Arg Phe Asp Ser Ala Ile Thr
        260                 265                 270

Asn Leu Gly Asn Thr Val Thr Asn Leu Asn Ser Ala Arg Ser Arg Ile
        275                 280                 285

Glu Asp Ala Asp Tyr Ala Thr Glu Val Ser Asn Met Ser Lys Ala Gln
        290                 295                 300

Ile Leu Gln Gln Ala Gly Thr Ser Val Leu Ala Gln Ala Asn Gln Val
305                 310                 315                 320

Pro Gln Asn Val Leu Ser Leu Leu Arg
                325
```

METHODS AND COMPOSITIONS FOR THE TREATMENT OF RADIATION-RELATED DISORDERS

CROSS REFERENCE TO RELATED APPLICATIONS

This application is the National Stage of International Patent Application No. PCT/US15/55986, filed Oct. 16, 2015, which claims the benefit of U.S. Provisional Patent Application Nos. 62/064,872, filed Oct. 16, 2014 and 62/214,572, filed Sep. 4, 2015, the entire contents of which are incorporated by reference herein.

FIELD OF THE INVENTION

This invention relates, inter alia, to methods and compositions that are useful for the treatment or prevention of various disorders, including radiation-related disorders, such as acute radiation syndrome (ARS).

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: CLE014PC-Sequencelisting.txt; date recorded: Oct. 14, 2015; file size: 4.61 KB).

BACKGROUND

With an increasing risk of nuclear and radiological emergencies, there is a critical need for development of medical radiation countermeasures (MRC) which are safe, easily administered and effective in preventing and/or mitigating the potentially lethal tissue damage caused by radiation exposure, especially high-dose radiation exposure (e.g. ARS). There are currently no FDA approved MRCs. Commercially available granulocyte colony-stimulating factor (G-CSF, filgrastim) has been of interest as a MRC; however, G-CSF has only shown variably positive results in animal studies, has limited utility in mass-casualty situations due to the need for multiple injections, supportive care, and laboratory monitoring, and is not approved by FDA for this purpose. The inflammatory cytokine interleukin (IL)-12 has also been evaluated, but did not demonstrate consistently significant radiomitigation in animal studies, has substantial inflammatory toxicity in humans, has not undergone a defined animal-to-human dose-conversion plan, and is unapproved by FDA for any use.

CBLB502 is a truncated derivative of the *Salmonella* flagellin protein that acts by triggering Toll-like receptor 5 (TLR5) signaling and has shown great promise in development as a MRC. The efficacy of MRCs, including CBLB502, for preventing and/or mitigating the potentially lethal tissue damage caused by radiation exposure is difficult to assess since they cannot be ethically tested in humans. There remains a need for safe and effective doses of MRCs, like CBLB502.

SUMMARY OF THE INVENTION

Accordingly, the present invention provides for methods and compositions that are useful in preventing and/or mitigating the potentially lethal tissue damage caused by radiation exposure, including doses, regimens, and kits that comprise CBLB502 a/k/a/ entolimod and provide safe and effective treatment and/or prevention of ARS.

In one aspect, the present invention provides a method of treating or preventing ARS, comprising administering an effective amount of CBLB502 to a human patient, where the effective amount of CBLB502 is about 0.35 to about 0.75 µg/kg or about 0.40 to about 0.60 µg/kg. In some embodiments, the effective amount of CBLB502 is about 0.4 to about 0.6 µg/kg (e.g. about 0.4, or about 0.45, or about 0.5, or about 0.55, or about 0.6 µg/kg). In some embodiments the human patient has been exposed or is at risk of being exposed to a high dose of radiation. In various embodiments, the treatment reduces morbidity or mortality of an exposed population of human patients or accelerates recovery from symptoms of ARS. In various embodiments, the human patient is administered CBLB502 within one or more of the triage, emergency care, and definitive care stages of radiation and combined injuries, for example CBLB502 may be administered within about 1 to about 48 hours, about 1 to about 25 hours, or about 5 to about 20 hours, or about 10 to about 15 hours of being exposed to radiation (e.g. within about 48 hours of being exposed to radiation, or within about 25 hours of being exposed to radiation, i.e. 48 hours or less or 25 hours or less after being exposed to radiation). In various embodiments the dose of CBLB502 is about 0.35 µg/kg, or about 0.4 µg/kg, or about 0.45 µg/kg, or about 0.5 µg/kg, or about 0.55 µg/kg, or about 0.6 µg/kg and may be slightly altered by the human patient's body weight (e.g. an absolute dose of CBLB502 of about 2 µg for a pediatric human patient of about 0 to about 5 kg (e.g. about 0, or about 1, or about 2, or about 3, or about 4, or about 5 kg); or about 3 µg for a pediatric human patient of about 6 to about 8 kg (e.g. about 6, or about 7, or about 8 kg), or about 5 µg for a pediatric human patient of about 9 to about 13 kg (e.g. 9, or about 10, or about 11, or about 12, or about 13 kg); or about 8 µg for a pediatric human patient of about 14 to about 20 kg (e.g. about 14, or about 16, or about 18, or about 20 kg), or about 12 µg for a pediatric human patient of about 21 to about 30 kg (e.g. about 21, or about 23, or about 25, or about 27, or about 30 kg), or about 13 µg for a pediatric human patient of about 31 to about 33 kg (e.g. about 31, or about 32, or about 33 kg), or about 20 µg for an adult human patient of about 34 to about 50 kg (e.g. about 34, or about 36, or about 38, or about 40, or about 42, or about 44, or about 46, or about 48, or about 50 kg), or about 30 µg for an adult human patient of about 51 to about 75 kg (e.g. about 51, or about 55, or about 60, or about 65, or about 70, or about 75 kg), or about 45 µg for an adult human patient of greater than about 114 kg (e.g. about 114, or about 120, or about 130, or about 140, or about 150 kg) In various embodiments, CBLB502 is administered by injection (e.g. intramuscular injection, or a single intramuscular injection).

In some embodiments, ARS comprises one of more of gastrointestinal syndrome; hematopoietic syndrome; neurovascular syndrome; apoptosis-mediated tissue damage, wherein the apoptosis is optionally attributable to cellular stress; and ionizing radiation induced apoptosis tissue damage. In some embodiments, the high dose of radiation (e.g. ionizing radiation) is about 5 to about 30 Gy, or about 10 to about 25 Gy, or about 15 to about 20 Gy and, optionally, sufficient for a classification of Unit Radiation Exposure Status of RES 3. In various embodiments, the high dose of radiation is the result of a radiation disaster and/or the human patient being treated has been exposed or is at risk of being exposed to a high dose of radiation as a result of one or more of a military operation or a first responder operation in a contaminated area; a nuclear explosion; a criticality accident; a radiotherapy accident; a terrorist attack; exposure from space travel; escape of radioactive waste; exposure to open source radiation; and a nuclear reactor malfunction.

In another aspect, the present invention provides a kit which is suitable for use upon exposure to a high dose of radiation, comprising CBLB502, optionally formulated for intramuscular injection, in one or more unit dosage forms of about 17.5 to about 47.5 μg (e.g. about 35 μg) and an injection needle. In some embodiments, the kit further comprises instructions for use and/or one or more of a radioactivity detector, potassium iodide (KI) or potassium iodate ($KIO_3$), gloves, face mask, hood, and cleaning solutions, and cleaning wipes. In various embodiments, the kit is suitable for military field operations. In some embodiments, the present kits further comprise ibuprofen and/or a bottle of water for oral hydration.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 shows the sequence of CBLB502 (SEQ ID NO: 1).

DETAILED DESCRIPTION OF THE INVENTION

The present invention is based, in part, on the discovery of effective and safe doses of CBLB502 for use in humans for the treatment of ARS. The present inventors have surprisingly discovered that the human dose is less than 1 μg/kg, which is far less than conventional biologics (which are often administered in the mg/kg range) and far less than prior animal studies on CBLB502 (e.g. Science 320, 226 (2008) and *J Pharmacol Exp Ther.* 343(2):497-508 (2012) (the contents of which are hereby incorporated by reference in their entireties).

In one aspect, the present invention provides a method of treating or preventing ARS, comprising administering an effective amount of CBLB502 to a human patient in need thereof, where the effective amount of CBLB502 is about 0.35 to about 0.75 μg/kg. In some embodiments, the effective amount of CBLB502 is about 0.4 to about 0.6 μg/kg (e.g. about 0.4, or about 0.45, or about 0.5, or about 0.55, or about 0.6 μg/kg). In some embodiments, the effective amount of CBLB502 is about 2 μg/subject to about 45 μg/subject, or about 5 to about 40, or about 10 to about 30, or about 15 to about 25 μg/subject. In another aspect, the present invention provides for use of about 0.35 to about 0.75 μg/kg of CBLB502 (e.g. about 0.4 to about 0.6 μg/kg) in the treatment or prevention of ARS. In another aspect, the invention provides a use of about 0.35 to about 0.75 μg/kg of CBLB502 (e.g. about 0.4 to about 0.6 μg/kg) in the manufacture of a medicament for the treatment or prevention of ARS.

In one aspect, the present invention provides a method of reducing the risk of death following exposure to potentially lethal irradiation (for instance, ≥2 Gy) occurring as the result of a radiation disaster comprising administering an effective amount of CBLB502 to a human patient in need thereof. In various embodiments, the effective amount of CBLB502 is about 0.4 to about 0.6 μg/kg (e.g. about 0.4, or about 0.45, or about 0.5, or about 0.55, or about 0.6 μg/kg).

Figure 7:
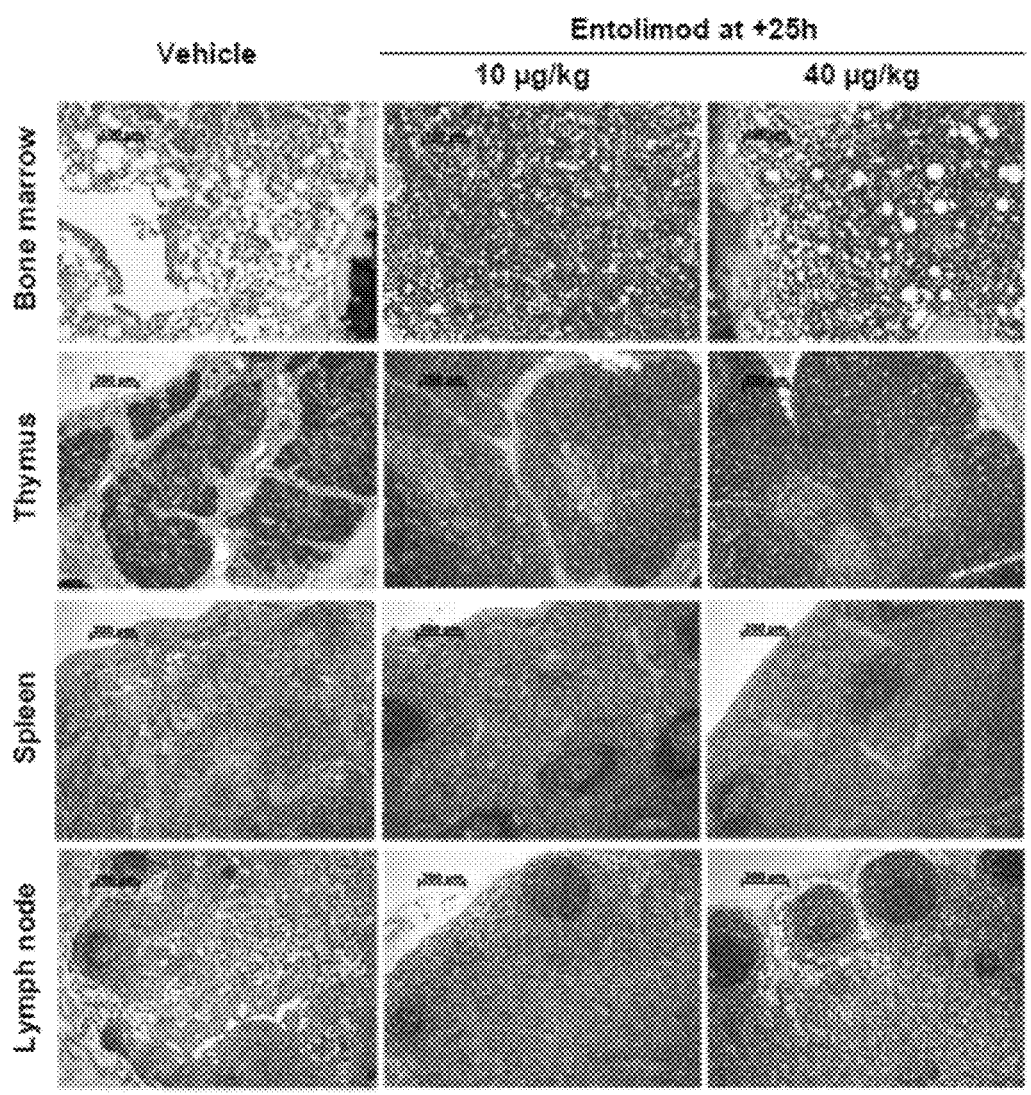
FIG. 7 shows comparable restorative effects of single 10 or 40 μg/kg entolimod treatments given 25 hours after TBI on morphological recovery of hematopoietic and lymphoid organs in NHPs 40 days after irradiation with $LD_{50/40}$ of TBI. Representative histological images (hematoxylin-eosin staining) of sternum bone marrow sections, thymuses, spleens and mesenteric lymph nodes from animals that survived to study termination on Day 40 post-TBI (study Rs-14). Scale bars: 100 μm for bone marrow, 200 μm for thymus, spleen, and lymph node.

CBLB502 is a flagellin-related polypeptide (see, e.g., FIG. 7 of U.S. Patent Publication No. 2003/0044429, the contents of which are incorporated herein by reference in their entirety). As used herein "CBLB502" (aka "Entolimod") refers to a polypeptide which comprises the sequence of SEQ ID NO: 1 or a sequence of about 95%, or about 96%, or about 97% or about 98%, or about 99% sequence similarity thereto.

In some embodiments, CBLB502 activates TLR5 signaling and, optionally, activation of TLR5 induces expression of the nuclear factor NF-κB, which in turn activates numerous targets, including inflammatory-related cytokines. In further embodiments, CBLB502 induces expression of proinflammatory cytokines. In further embodiments, CBLB502 induces expression of anti-inflammatory molecules. In another embodiment, CBLB502 induces expression of anti-apoptotic molecules. In yet a further embodiment, CBLB502 induces expression of anti-bacterial molecules. Targets of NF-κB, include, but are not limited to, IL-β, TNF-α, IL-6, IL-8, IL-18, G-CSF, TNFSF13B, keratinocyte chemoattractant (KC), BLIMP1/PRDM1, CCL5, CCL15, CCL17, CCL19, CCL20, CCL22, CCL23, CXCL1, CCL28, CXCL11, CXCL10, CXCL3, CXCL1, GRO-beta, GRO-gamma, CXCL1, ICOS, IFNG, IL-1A, IL-1B, IL1RN, IL-2, IL-9, IL-10, IL-11, IL-12, IL-12B, IL-12A, IL-13, IL-15, IL-17, IL-23A, IL-27, EBI3, IFNB1, CXCL5, KC, liGp1, CXCL5, CXCL6, LTA, LTB, CCL2, CXCL9, MCP-1/JE, CCL3, CCL4, CXCL3, CCL20, CXCL10, CXCL5, CCL5, CCL1, TNF beta, TNFSF10, TFF3, TNFSF15, CD86, complement component 8a, CCL27, defensin-β3, MIG, MIP-2, and/or NOD2/CARD15. Targets of NF-κB, include, but are not limited to G-CSF and IL-6. In some embodiments, any of these targets find use as biomarkers (e.g. for dosing and/or determination of presence and/or extent of a radiation-based disorder). Further biomarkers include numbers, including relative numbers, of blood cell counts, including but not limited to, lymphocytes, neutrophils, platelets, and ratio of neutrophils to lymphocytes.

In some embodiments, CBLB502 is administered to a human patient at an effective amount (a.k.a. dose) of less than about 1 µg/kg, for instance, about 0.35 to about 0.75 µg/kg or about 0.40 to about 0.60 µg/kg. In some embodiments, the dose of CBLB502 is about 0.35 µg/kg, or about 0.40 µg/kg, or about 0.45 µg/kg, or about 0.50 µg/kg, or about 0.55 µg/kg, or about 0.60 µg/kg, or about 0.65 µg/kg, or about 0.70 µg/kg, or about 0.75 µg/kg, or about 0.80 µg/kg, or about 0.85 µg/kg, or about 0.90 µg/kg, or about 0.95 µg/kg or about 1 µg/kg. In various embodiments, the absolute dose of CBLB502 is about 2 µg/subject to about 45 µg/subject, or about 5 to about 40, or about 10 to about 30, or about 15 to about 25 µg/subject. In some embodiments, the absolute dose of CBLB502 is about 20 µg, or about 30 µg, or about 40 µg.

In various embodiments, the dose of CBLB502 may be determined by the human patient's body weight. For example, an absolute dose of CBLB502 of about 2 µg for a pediatric human patient of about 0 to about 5 kg (e.g. about 0, or about 1, or about 2, or about 3, or about 4, or about 5 kg); or about 3 µg for a pediatric human patient of about 6 to about 8 kg (e.g. about 6, or about 7, or about 8 kg), or about 5 µg for a pediatric human patient of about 9 to about 13 kg (e.g. 9, or about 10, or about 11, or about 12, or about 13 kg); or about 8 µg for a pediatric human patient of about 14 to about 20 kg (e.g. about 14, or about 16, or about 18, or about 20 kg), or about 12 µg for a pediatric human patient of about 21 to about 30 kg (e.g. about 21, or about 23, or about 25, or about 27, or about 30 kg), or about 13 µg for a pediatric human patient of about 31 to about 33 kg (e.g. about 31, or about 32, or about 33 kg), or about 20 µg for an adult human patient of about 34 to about 50 kg (e.g. about 34, or about 36, or about 38, or about 40, or about 42, or about 44, or about 46, or about 48, or about 50 kg), or about 30 µg for an adult human patient of about 51 to about 75 kg (e.g. about 51, or about 55, or about 60, or about 65, or about 70, or about 75 kg), or about 45 µg for an adult human patient of greater than about 114 kg (e.g. about 114, or about 120, or about 130, or about 140, or about 150 kg).

In various embodiments, CBLB502 is administered within about 1 to about 48 hours, or about 1 to about 25 hours, or about 5 to about 20 hours, or about 10 to about 15 hours of a human patient being exposed to radiation. In some embodiments, CBLB502 is administered within about 1, or about 2, or about 3, or about 4, or about 5, or about 6, or about 7, or about 8, or about 9, or about 10, or about 11, or about 12, or about 13, or about 14, or about 15, or about 16, or about 17, or about 18, or about 19, or about 20, or about 21, or about 22, or about 23, or about 24, or about 25, or about 26, or about 27, or about 28, or about 29, or about 30, or about 31, or about 32, or about 33, or about 34, or about 35, or about 36, or about 37, or about 38, or about 39, or about 40, or about 41, or about 42, or about 43, or about 44, or about 45, or about 46, or about 47, or about 48 hours of a human patient being exposed to radiation. In one embodiment, a human patient is administered CBLB502 within about 25 hours of being exposed to radiation. In another embodiment, a human patient is administered CBLB502 within about 48 hours of being exposed to radiation.

The medical management of radiation and combined injuries can be divided into three stages: triage, emergency care, and definitive care. During triage, patients are prioritized and rendered immediate lifesaving care. Emergency care includes therapeutics and diagnostics necessary during the first 12 to 24 hours. Definitive care is rendered when final disposition and therapeutic regimens are established. In one embodiment, CBLB502 is administered as part of the triage emergency care stages. For example, it may be used during a military field operation as described herein and, optionally, may find use in a kit. In various embodiments, CBLB502 is administered within one or more of the triage, emergency care, and definitive care stages of radiation and combined injuries.

Administration of CBLB502 (and/or additional agents) described herein can, independently, be one to four times daily or one to four times per month or one to six times per year or once every two, three, four or five years. Administration can be for the duration of one day or one month, two months, three months, six months, one year, two years, three years, and may even be for the life of the human patient. The dosage may be administered as a single dose or divided into multiple doses. In some embodiments, CBLB502 is administered about 1 to about 3 times (e.g. 1, or 2 or 3 times). In some embodiments, CBLB502 is administered once. In some embodiments, CBLB502 (and/or additional agents) described herein is administered as a slow IV infusion or drip (e.g. over about 0.5, or about 1, or about 1.5, or about 2, or about 2.5, or about 3, or about 5, or about 10 hours).

Various modes of administration of CBLB502 and additional agents are disclosed herein. In one embodiment, CBLB502 is administered parenterally. In some embodiments, CBLB502 is administered by injection, e.g. intramuscular injection. In some embodiments, CBLB502 is by a single intramuscular injection. In some embodiments, administration is accomplished using a kit as described herein (e.g. via a unit dose form, e.g. a pre-loaded (a.k.a. pre-dosed or pre-filled) syringe or a pen needle injector (injection pen)).

In various embodiments, the present methods and compositions provide treatment or prevention of radiation-related disorders, such as ARS. In various embodiments, the treatments described herein reduce morbidity or mortality of an exposed population of human patients or accelerates recovery from symptoms of ARS. ARS often presents as a sequence of phased symptoms, which may vary with individual radiation sensitivity, type of radiation, and the radiation dose absorbed. Generally, without wishing to be bound by theory, the extent of symptoms will heighten and the duration of each phase will shorten with increasing radiation dose. ARS can be divided into three phases: prodromal phase (a.k.a. N-V-D stage), latent period and manifest illness. In various embodiments, CBLB502, as describe herein, may be administered to a human patient in any one of these three stages (i.e. CBLB502 may be administered to a human patient in the prodromal phase, CBLB502 may be administered to a human patient in latent period, or CBLB502 may be administered to a human patient in manifest illness stage).

In the prodromal phase there is often a relatively rapid onset of nausea, vomiting, and malaise. Use of antiemetics, (e.g. oral prophylactic antiemetics) such as granisetron (KYTRIL), ondansetron (ZOFRAN), and 5-HT3 blockers with or without dexamethasone, may be indicated in situations where high-dose radiological exposure has occurred, is likely, or is unavoidable. Accordingly, in various embodiments, CBLB502 may be administered to a human patient in receiving an anti-emetic agent or CBLB502 may be administered to a human patient in combination with an anti-emetic agent. For example, CBLB502 may also be added to the following antiemetic regimens: Ondansetron: initially 0.15 mg/kg IV; a continuous IV dose option consists of 8 mg followed by 1 mg/h for the next 24 hours. Oral dose is 8 mg every 8 hours as needed or Granisetron (oral dosage form): dose is usually 1 mg initially, then repeated 12 hours after the first dose. Alternatively, 2 mg may be taken as one dose. IV dose is based on body weight; typically 10 μg/kg (4.5 μg/lb) of body weight.

In the latent period, a human patient may be relatively symptom free. The length of this phase varies with the dose. The latent phase is longest preceding the bone-marrow depression of the hematopoietic syndrome and may vary between about 2 and 6 weeks. The latent period is somewhat shorter prior to the gastrointestinal syndrome, lasting from a few days to a week. It is shortest of all preceding the neurovascular syndrome, lasting only a matter of hours. These times are variable and may be modified by the presence of other disease or injury. Manifest illness presents with the clinical symptoms associated with the major organ system injured (marrow, intestinal, neurovascular).

In some embodiments, the present invention relates to the mitigation of, or protection of cells from, the effects of exposure to radiation. In some embodiments, the present invention pertains to a method of mitigating and/or protecting a human patient from radiation comprising administering CBLB502 at the disclosed doses and regimens (and/or additional agents) described herein. In some embodiments, the radiation is ionizing radiation. In some embodiments, the ionizing radiation is sufficient to cause gastrointestinal syndrome or hematopoietic syndrome.

In some embodiments, the ARS comprises one of more of gastrointestinal syndrome; hematopoietic syndrome; neurovascular syndrome; apoptosis-mediated tissue damage, wherein the apoptosis is optionally attributable to cellular stress; and ionizing radiation induced apoptosis tissue damage.

Hematopoietic syndrome (a.k.a. bone marrow syndrome) is characterized by loss of hematopoietic cells and their progenitors making it impossible to regenerate blood and lymphoid system. This syndrome is often marked by a drop in the number of blood cells, i.e., aplastic anemia. This may result in infections (e.g. opportunistic infections) due to a low amount of white blood cells, bleeding due to a lack of platelets, and anemia due to few red blood cells in the circulation. These changes can be detected by blood tests after receiving a whole-body acute dose.

Conventional trauma and burns resulting from a bomb blast are complicated by the poor wound healing caused by hematopoietic syndrome, increasing mortality. Death may occur as a consequence of infection (result of immunosuppression), hemorrhage and/or anemia. Hematopoietic syndrome usually prevails at the lower doses of radiation and leads to the more delayed death than GI syndrome.

Gastrointestinal syndrome is caused by massive cell death in the intestinal epithelium, predominantly in the small intestine, followed by disintegration of intestinal wall and death from bacteriemia and sepsis. Symptoms of this form of radiation injury include nausea, vomiting, loss of appetite, loss of absorptive capacity, hemorrhage in denuded areas, and abdominal pain. Illustrative systemic effects of gastrointestinal syndrome include malnutrition, dehydration, renal failure, anemia, sepsis, etc. Without treatment (including, for example, bone marrow transplant), death is common (e.g. via infection from intestinal bacteria). In some embodiments, CBLB502, at the doses and regimens described herein, may be used in combination with bone marrow transplant. In some embodiments, CBLB502, at the doses and regimens described herein, may be used in combination with one or more inhibitors of GI syndrome and/or any of the additional agents described herein.

Neurovascular syndrome presents with neurological symptoms such as dizziness, headache, or decreased level of consciousness, occurring within minutes to a few hours, and with an absence of vomiting. Additional symptoms include extreme nervousness and confusion; severe nausea, vomiting, and watery diarrhea; loss of consciousness; and burning sensations of the skin. Neurovascular syndrome is commonly fatal.

In some embodiments, the present invention provides a method for reducing the risk of death following exposure to irradiation comprising administering an effective amount of CBLB502. In some embodiments, the radiation is potentially lethal, and, optionally, occurs as the result of a radiation disaster. In various embodiments, CBLB502 is administered within 25 hours following radiation exposure. In various embodiments, CBLB502 is administered within 48 hours following radiation exposure. In some embodiments, the present invention provides a method for reducing the risk of death following exposure to potentially lethal irradiation occurring as the result of a radiation disaster, comprising administering CBLB502 within 25 hours following radiation exposure. In some embodiments, the present invention provides a method for reducing the risk of death following exposure to potentially lethal irradiation occurring as the result of a radiation disaster, comprising administering CBLB502 within 48 hours following radiation exposure In some embodiments, CBLB502 at the disclosed doses and regimens is used to treat a disorder linked to apoptosis which is attributable to cellular stress (see, e.g. U.S. Pat. Nos. 7,638,485 and 8,106,005, the contents of which are hereby incorporated by reference in their entirety). In some embodiments, CBLB502 (and/or additional agents) described herein are administered prior to, together with, or after the tissue damage. In some embodiments, the cellular stress is radiation. In some embodiments, CBLB502 (and/or additional agents) are administered in combination with any additional agent described herein, including but not limited to a radioprotectant (e.g. an antioxidant (e.g. amifostine and vitamin E), a cytokine (e.g. a stem cell factor)), etc. Injury and death of normal cells from ionizing radiation is a combination of a direct radiation-induced damage to the exposed cells and an active genetically programmed cell reaction to radiation-induced stress resulting in a suicidal death or apoptosis. Apoptosis plays a key role in massive cell loss occurring in several radiosensitive organs (e.g., hematopoietic and immune systems, epithelium of digestive tract, etc.), the failure of which determines general radiosensitivity of the organism. In some embodiments, administration of CBLB502 (and/or additional agents) of the invention to a human patient in need thereof suppresses apoptosis in cells. In some embodiments, CBLB502 (and/or additional agents) of the invention are administered to a human patient to protect healthy cells from the damaging effects of the radiation treatment.

In various embodiments, the present invention provides a method for reducing apoptosis following exposure to irradiation. In an embodiment, the present invention provides a method for reducing apoptosis of hematopoietic cells following irradiation. In another embodiment, the present invention provides a method for reducing apoptosis of gastrointestinal cells following irradiation.

In various embodiments, administration of CBLB502 at the disclosed dosages stimulates and protects stem cells. For example, the present invention and composition may stimulate and protect hematopoietic stem cells including various hematopoietic progenitor cells. In another example, the present invention and composition may stimulate and protect gastrointestinal stem cells such as intestinal crypt stem cells. In some embodiments, the stem cells may be stimulated to proliferate and regenerate. Accordingly the present invention provides methods of expanding the number of stem cells such as hematopoietic stem cells or gastrointestinal stem cells in a patient. In some embodiments, hematopoietic progenitor cells or gastrointestinal progenitor cells are expanded. In various embodiments, the present invention provides methods and compositions that protect the stem cells or progenitors cells from cell death (e.g., apoptosis or necrosis).

In various embodiments, methods and compositions of the present invention significantly enhances recovery of the hematopoietic and GI systems following irradiation. For example, methods and compositions of the present invention enhances bone marrow recovery following irradiation. In another example, methods and compositions of the present invention enhances regeneration of the GI crypt.

Exposure to ionizing radiation (IR) may be short- or long-term, and/or it may be experienced as a single or multiple doses and/or it may be applied to the whole body or locally. The present invention, in some embodiments, pertains to nuclear accidents or military attacks, which may involve exposure to a single high dose of whole body irradiation (sometimes followed by a long-term poisoning with radioactive isotopes), as further described herein. The same is true (with strict control of the applied dose), for example, for pretreatment of patients for bone marrow transplantation when it is necessary to prepare hematopoietic organs for donor's bone marrow by "cleaning" them from the host blood precursors. Cancer treatment may involve multiple doses of local irradiation that greatly exceeds lethal dose if it were applied as a total body irradiation (e.g. a radiotherapy accident). Poisoning or treatment with radioactive isotopes results in a long-term local exposure to radiation of targeted organs (e.g., thyroid gland in the case of inhalation of $^{125}$I). Further, there are many physical forms of ionizing radiation differing significantly in the severity of biological effects.

At the molecular and cellular level, radiation particles are able to produce breakage and cross-linking in the DNA, proteins, cell membranes and other macromolecular structures. Ionizing radiation also induces the secondary damage to the cellular components by giving rise to the free radicals and reactive oxygen species (ROS). Multiple repair systems counteract this damage, such as, several DNA repair pathways that restore the integrity and fidelity of the DNA, and antioxidant chemicals and enzymes that scavenge the free radicals and ROS and reduce the oxidized proteins and lipids. Cellular checkpoint systems detect the DNA defects and delay cell cycle progression until damage is repaired or decision to commit cell to growth arrest or programmed cell death (apoptosis) is reached Radiation can cause damage to mammalian organism ranging from mild mutagenic and carcinogenic effects of low doses to almost instant killing by high doses. Overall radiosensitivity of the organism is determined by pathological alterations developed in several sensitive tissues that include hematopoietic system, reproductive system and different epithelia with high rate of cell turnover.

Acute pathological outcome of gamma irradiation leading to death is different for different doses and may be determined by the failure of certain organs that define the threshold of organism's sensitivity to each particular dose. Thus, lethality at lower doses occurs from bone marrow aplasia, while moderate doses kill faster by inducing a gastrointestinal (GI) syndrome. Very high doses of radiation can cause almost instant death eliciting neuronal degeneration. Organisms that survive a period of acute toxicity of radiation can suffer from long-term remote consequences that include radiation-induced carcinogenesis and fibrosis developing in exposed organs (e.g., kidney, liver or lungs) in the months and years after irradiation. Cellular DNA is a major target of IR that causes a variety of types of DNA damage (genotoxic stress) by direct and indirect (e.g. free radical-based) mechanisms. All organisms maintain DNA repair system capable of effective recovery of radiation-damaged DNA; errors in DNA repair process may lead to mutations.

CBLB502, at the doses and regimens described herein, possesses strong pro-survival activity at the cellular level and on the organism as a whole. In response to super-lethal doses of radiation, CBLB502 may inhibit both gastrointestinal and hematopoietic syndromes, which are major causes of death from acute radiation exposure. As a result of these properties, CBLB502 may be used to treat the effects of natural radiation events and nuclear accidents. Moreover, CBLB502 can be used in combination with other radioprotectants, thereby, dramatically increasing the scale of protection from ionizing radiation.

CBLB502, at the doses and regimens described herein, may be used as a radioprotective agent to extend the range of tolerable radiation doses by, for example, increasing radioresistance of human organism beyond the levels achievable by currently available measures (shielding and application of existing bioprotective agents) and drastically increase the chances of crew survival in case of nuclear accidents or large-scale solar particle events, for example.

CBLB502, at the doses and regimens described herein, may inhibit radiation-induced programmed cell death or apoptosis in response to damage in DNA and other cellular structures. In some embodiments, CBLB502 as described herein may not deal with damage at the cellular level and may not prevent mutations. Free radicals and reactive oxygen species (ROS) are the major cause of mutations and other intracellular damage. Antioxidants and free radical scavengers are effective at preventing damage by free radicals.

Further, in some embodiments, the present invention relates to the prevention or treatment of cutaneous radiation syndrome (CRS), i.e. skin symptoms of radiation exposure (e.g. redness (optionally associated with itching), blistering, ulceration, hair loss, damaged sebaceous and sweat glands, atrophy, fibrosis, decreased or increased skin pigmentation, ulceration or necrosis of the exposed tissue moist desquamation and collapse of the dermal vascular system after two months, resulting in the loss of the full thickness of the exposed skin.

In various embodiments, administration of CBLB502 at the disclosed dosages reduces the incidence of wounds, septic complications, and microbial infections in patients following irradiation.

In some embodiments, the present human patients experience leukopenia and/or neutropenia (e.g. absolute neutrophil count (ANC)<100 cells/µL. In some embodiments, the present methods and compositions pertain to a human patient which presents a lymphocyte count reduction of about 50% within about 24 to about 48 hours. In some embodiments, the human patient's lymphocyte count is less than about 1000 cells/µL, or about 900 cells/µL, or about 800 cells/µL, or about 700 cells/µL, or about 600 cells/µL, or about 500 cells/µL, or about 400 cells/µL, or about 300 cells/µL, or about 200 cells/µL, or about 100/cells µL (e.g. within about 24 to about 48 hours). In some embodiments, the patient's lymphocyte profile is assessed by the Andrews Lymphocyte Nomogram (see Andrews G A, Auxier J A, Lushbaugh C C. *The Importance of Dosimetry to the Medical Management of Persons Exposed to High Levels of Radiation*. In *Personal Dosimetry for Radiation Accidents*. Vienna: International Atomic Energy Agency; 1965, the contents of which are hereby incorporated by reference). In some embodiments, the present methods and compositions pertain to a human patient which presents a thrombocyte count reduction of about 50% within about 24 to about 48 hours. In some embodiments, the present human patients experience thrombocytopenia, anemia, and/or neutropenia. Thrombocytopenia is defined as a platelet count of below 50,000/μL. For example, thrombocytopenia may be characterized as grade 1 thrombocytopenia (i.e., platelet count of 75,000 to 150,000/μL), grade 2 (i.e., platelet count of 50,000 to <75,000 μL), grade 3 (platelet count of 25,000 to <50,000/μL), or grade 4 (i.e., platelet count of below 25,000/μL). Anemia may be diagnosed in men as having a hemoglobin content of less than 13 to 14 g/dL and in women as having a hemoglobin content of 12 to 13 g/dL. For example, anemia is divided into various grades based on hemoglobin levels: grade 0 (within normal limits, ≥12 g/dL); grade 1 (mild, 11.9 to 10 g/dL); grade 2 (moderate, 9.9 to 8 g/dL); grade 3 (serious/severe, 7.9 to 6.5 g/dL); and grade 4 (life-threatening, <6.5 g/dL). Neutropenia may be defined as having an absolute neutrophil count (ANC) of less than 1,500 cells/$mm^3$. For example, neutropenia is graded as grade 1 (i.e., ANC of 1,500/$mm^3$ or less to more than 2,000/$mm^3$), grade 2 (ANC of 1,000/$mm^3$ or less to more than 1,500/$mm^3$), grade 3 (ANC of 500/$mm^3$ or less to more than 1,000/$mm^3$), or grade 4 (ANC of less than 500/$mm^3$). In various embodiments, the present methods and compositions reduces the duration and severity of thrombocytopenia, anemia, and/or neutropenia in a patient following irradiation. For example, the present methods and compositions may reduce the duration and severity of Grade 4 thrombocytopenia, anemia, and/or neutropenia in a patient following irradiation.

In various embodiments, the high dose of radiation refers to a whole body dose. In various embodiments, the high dose of radiation may not be uniform. In various embodiments, the ARS is a result of a high dose of radiation. In various embodiments, the high dose of radiation is about 2 Gy, or about 2.5 Gy, or about 3 Gy, or about 3.5 Gy, or about 4 Gy, or about 4.5 Gy, or about 5 Gy, or about 10 Gy, or about 15 Gy, or about 20 Gy, or about 25 Gy, or about 30 Gy. In various embodiments, the high dose of radiation is about 5 to about 30 Gy, or about 10 to 25 Gy, or about 15 to 20 Gy. In some embodiments, the high dose of radiation is assessed by one or more of physical dosimetry and/or biological dosimetry (e.g. multiparameter dose assessments), cytogenics (e.g. chromosomal analysis for, for example, blood samples (including, by way of non-limiting example, dicentric analysis).

In various embodiments, whole-body radiation doses can be divided into sublethal (<2 Gy), potentially lethal (2-10 Gy), and supralethal (>10 Gy).

The radiation exposure status (RES) of a given unit is based on the operational exposure above normal background radiation. It is designed to be an average, based upon unit-level dosimeters. In various embodiments, the high dose of radiation is sufficient for a classification of Unit Radiation Exposure Status of RES 3.

In various embodiments, the radiation is ionizing radiation (e.g. one or more of alpha particles, beta particles, gamma rays, and neutrons) In various embodiments, when radiation interacts with atoms, energy is deposited, resulting in ionization (electron excitation). This ionization may damage certain critical molecules or structures in a cell by direct and indirect action. The radiation may directly hit a particularly sensitive atom or molecule in the cell. The damage from this is irreparable; the cell either dies or is caused to malfunction. The radiation also can damage a cell indirectly by interacting with water molecules in the body. The energy deposited in the water leads to the creation of unstable, toxic hyperoxide molecules; these then damage sensitive molecules and afflict subcellular structures.

In some embodiments, the radiation may be caused by one or more of the following radioactive materials: Americium (e.g. $^{241}$Am), Cesium (e.g. 137Cs), Cobalt (e.g. 60 Co), Uranium (e.g. depleted Uranium), Iodine (e.g. $^{131, 132, 134, 135}$I), Phosphorus (e.g. $^{32}$P), Plutonium (e.g. $^{238, 239}$Pu), Radium (e.g. $^{226}$Ra), Strontium (e.g. $^{90}$Sr), Tritium (e.g. $^3$H), and Uranium (e.g. 235, 238, 239U).

In various embodiments, the high dose of radiation is the result of a radiation disaster. In various embodiments, the human patient is been exposed or is at risk of being exposed to a high dose of radiation, which may be a result of one or more of a military operation or a first responder operation in a contaminated area; a nuclear explosion; a criticality accident; a radiotherapy accident; a terrorist attack; exposure from space travel; escape of radioactive waste; exposure to open source radiation; and a nuclear reactor malfunction.

In some embodiments, the present methods and compositions find use in accordance with military operations and/or are suitable for military operations. In some embodiments, the present methods and compositions find use in accordance with U.S. Field Manual (FM) 3-11.3, "MULTI-SERVICE TACTICS, TECHNIQUES, AND PROCEDURES FOR CHEMICAL, BIOLOGICAL, RADIOLOGICAL, AND NUCLEAR CONTAMINATION AVOIDANCE," the contents of which are hereby incorporated by reference in their entirety.

In some embodiments, CBLB502 at the doses and regimens described herein may be used in combination with one or more additional agents. In some embodiments, CBLB502 at the doses and regimens described herein may be used in a human patient undergoing treatment with one or more additional agent. In some embodiments, CBLB502 is used as an adjuvant or neoadjuvant to any of the additional agents described herein.

Adjuvant therapy, also called adjuvant care, is treatment that is given in addition to the primary, main or initial treatment. By way of non-limiting example, adjuvant therapy may be an additional treatment usually given after primary care where there remains a statistical risk of relapse. In certain embodiments, neoadjuvant therapy refers to therapy to provide a beneficial effect prior to any primary care.

In various embodiments, the additional agents of the present invention include one or more of blood products, colony stimulating factors, cytokines and/or growth factors, antibiotics, diluting and/or blocking agents, mobilizing or chelating agents, stem cell transplants, antioxidants or free radicals, and radioprotectants.

In some embodiments, the blood product is one or more of hematopoietic growth factors, such as filgrastim (e.g. NEUPOGEN), a granulocyte colony-stimulating factor (G-CSF), which may be optionally pegylated (e.g. NEULASTA); sargramostim (LEUKINE); and a granulocyte-macrophage colony-stimulating factor (GM-CSF) and a KSF.

In some embodiments, the additional agent is one or more cytokines and/or growth factors that may confer radioprotection by replenishing and/or protecting the radiosensitive stem cell populations. Radioprotection with minimal side effects may be achieved by the use of stem cell factor (SCF, c-kit ligand), Flt-3 ligand, and interleukin-1 fragment IL-1b-rd. Protection may be achieved through induction of proliferation of stem cells (e.g. via all mentioned cytokines), and prevention of their apoptosis (e.g. via SCF). The treatment allows accumulation of leukocytes and their precursors prior to irradiation thus enabling quicker reconstitution of the immune system after irradiation. SCF efficiently rescues lethally irradiated mice with a dose modifying factor (DMF) in range 1.3-1.35 and is also effective against gastrointestinal syndrome. Flt-3 ligand also provides strong protection in mice and rabbits.

Several factors, while not cytokines by nature, stimulate the proliferation of the immunocytes and may be used in combination with CBLB502 at the doses and regimens described herein. For example, 5-AED (5-androstenediol) is a steroid that stimulates the expression of cytokines and increases resistance to bacterial and viral infections. Synthetic compounds, such as ammonium tri-chloro(dioxoethylene-O,O'-) tellurate (AS-101), may also be used to induce secretion of numerous cytokines and for combination with CBLB502. Growth factors and cytokines may also be used to provide protection against the gastrointestinal syndrome. Keratinocyte growth factor (KGF) promotes proliferation and differentiation in the intestinal mucosa, and increases the post-irradiation cell survival in the intestinal crypts. Hematopoietic cytokine and radioprotectant SCF may also increase intestinal stem cell survival and associated short-term organism survival.

In certain embodiments, CBLB502 may be added to a regimen of cytokines (e.g. for FILGRASTIM (G-CSF) 2.5-5 µg/kg/d QD s.c. (100-200 µg/m$^2$/d); for SARGRAMOSTIM (GM-CSF) 5-10 µg/kg/d QD s.c. (200-400 µg/m$^2$/d); and/or for PEGFILGRASTIM (pegG-CSF) 6 mg once s.c.).

In some embodiments, the additional agent is an interleukin, such as IL-12 (e.g. HEMAMAX (NEUMEDICINES, INC.)).

In some embodiments, the antibiotic is one or more of an anti-bacterial (anti-gram positive and anti-gram negative agents), and/or anti-fungal, and/or anti-viral agent. By way of non-limiting example, in some embodiments, the antibiotic may be a quinolone, e.g. ciprofloxacin, levofloxacin, a third- or fourth-generation cephalosporin with pseudomonal coverage: e.g., cefepime, ceftazidime, or an aminoglycoside: e.g. gentamicin, amikacin, penicillin or amoxicillin, acyclovir, vanomycin. In various embodiments, the antibiotic targets *Pseudomonas aeruginosa.*

In some embodiments, the additional agent is a diluting and/or blocking agents. For example, stable iodide compounds may be used (e.g. liquid (ThyroShield) and the tablet (losat) KI (NUKEPILLS), Rad Block, I.A.A.A.M., No-Rad, Life Extension (LEF), KI4U, NukeProtect, ProKI)). A 130 mg dose of daily of oral potassium iodide (KI) may be used in conjunction with CBLB502.

In some embodiments, the additional agent is a mobilizing or chelating agent. Illustrative mobilizing agents include propylthiouracil and methimazole, with may reduce the thyroid's retention of radioactive compounds. Further CBLB502 can be used alongside increasing oral fluids to a human patient to promote excretion. Illustrative chelating agents are water soluble and excreted in urine. Illustrative chelating agents include DTPA and EDTA. Dimercaprol forms stable chelates with mercury, lead, arsenic, gold, bismuth, chromium, and nickel and therefore may be considered for the treatment of internal contamination with the radioisotopes of these elements. Penicillamine chelates copper, iron, mercury, lead, gold, and possibly other heavy metals.

In some embodiments, the additional agent is a stem cell transplant (e.g. bone marrow transplant, PBSCT, MSCT). In some embodiments the stem cell transplant is Remestemcel-L (Osiris) of CLT-008 (Cellerant).

In some embodiments, the additional agent is an antioxidant or free radical. Antioxidants and free radical scavengers that may be used in the practice of the invention include, but are not limited to, thiols, such as cysteine, cysteamine, glutathione and bilirubin; amifostine (WR-2721); vitamin A; vitamin C; vitamin E; and flavonoids such as Indian holy basil (*Ocimum sanctum*), orientin and vicenin.

In some embodiments, the additional agent may be a radioprotectant e.g. an antioxidant (e.g. amifostine and vitamin E, gamma tocotrienol (a vitamin-E moiety), and genistein (a soy byproduct)), a cytokine (e.g. a stem cell factor), a growth factor (e.g. keratinocyte growth factor), a steroid (e.g. 5-androstenediol), ammonium trichloro(dioxoethylene-O,O')tellurate, thyroid protecting agents (e.g. Potassium iodide (KI) or potassium iodate ($KIO_3$) (e.g. liquid (ThyroShield) and the tablet (losat) KI (NUKEPILLS), Rad Block, I.A.A.A.M., No-Rad, Life Extension (LEF), KI4U, NukeProtect, ProKI)), anti-nausea agents, anti-diarrhea agents, antiemetics ((e.g. oral prophylactic antiemetics) such as granisetron (KYTRIL), ondansetron (ZOFRAN), and 5-HT3 blockers with or without dexamethasone), analgesics, anxiolytics, sedatives, cytokine therapy, and antibiotics.

Gastric lavage and emetics, which can be used as additional agents, can be used to empty the stomach promptly and completely after the ingestion of poisonous materials. Purgatives, laxatives, and enemas, which also can be used as additional agents, can reduce the residence time of radioactive materials in the colon. Further additional agents include ion exchange resins which may limit gastrointestinal uptake of ingested or inhaled radionuclides, ferric ferrocyanide (Prussian blue) and alginates, which have been used in humans to accelerate fecal excretion of cesium-137.

In still other embodiments, the additional agent may be an agent used to treat radiation-related disorders, such as, for example, 5-AED (Humanetics), Ex-RAD (Onconova), Beclometasone Dipropionate (Soligenix), detoxified endotoxin, EA-230 (Exponential Biotherapies), ON-01210.Na (Onconova), Sothrombomodulin alfa (PAION), Remestemcel-L (Osiris), BIO-100, BIO-200, BIO-300, BIO-400, BIO-500 (Humanetics), CLT-008 (Cellerant), EDL-2000 (Rx-Bio), Homspera (ImmuneRegen), MnDTEIP (Aeolus Pharmaceuticals), RLIP-76 (Terapio), and RX-100 and RX 101 (RxBio).

Further, in some embodiments, CBLB502 (and/or additional agents) can be used in combination with shielding; reduction of radiation exposure time; and use of agents to reduce body exposure (e.g. uses of gloves, face mask, hood, protective clothing (e.g. anticontamination suits such as TYVEK ANTI-C SUITS or MOPP-4)).

CBLB502 (and/or additional agents) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Prop-*

*erties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methyl benzoate, o-acetoxybenzoate, naphthalene-2-benzoate, isobutyrate, phenylbutyrate, a-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower al kylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glutamine; and amino acids such as arginine, lysine, and the like.

In some embodiments, the compositions described herein are in the form of a pharmaceutically acceptable salt.

Further, CBLB502 (and/or additional agents) described herein can be administered to a human patient as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a human patient. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

The present invention includes the described CBLB502 (and/or additional agents) in various formulations. CBLB502 (and/or additional agents) described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, CBLB502 (and/or additional agents) can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The formulations comprising CBLB502 (and/or additional agents) of the present invention may conveniently be presented in unit dosage forms, as further described herein, and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art)

In one embodiment, CBLB502 (and/or additional agents) described herein is formulated in accordance with routine procedures as a composition adapted for a mode of administration described herein (e.g. injection, for example, intramuscular injection).

Routes of administration include, for example: intramuscular, intradermal, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In some embodiments, the administering is effected orally or by parenteral injection. The mode of administration can be left to the discretion of the practitioner and/or human patient (e.g. in the case of emergency use). In most instances, administration results in the release of any agent described herein into the bloodstream.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

CBLB502 (and/or additional agents) described herein can also be administered orally. CBLB502 (and/or additional agents) can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In one embodiment, CBLB502 (and/or additional agents) described herein is formulated in accordance with routine procedures as a composition adapted for oral administration to humans. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving CBLB502 (and/or additional agents) described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

The dosage of any additional agent described herein as well as the dosing schedule can depend on various parameters, including, but not limited to, the human patient's general health, and the administering physician's and/or human patient's discretion. Any additional agent described herein, can be administered prior to (e.g., about 5 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, 8 weeks, or about 12 weeks before), concurrently with, or subsequent to (e.g., about 5 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks after) the administration of CBLB502, to a human patient in need thereof. In various embodiments any agent described herein is administered about 1 minute apart, about 10 minutes apart, about 30 minutes apart, less than about 1 hour apart, about 1 hour apart, about 1 hour to about 2 hours apart, about 2 hours to about 3 hours apart, about 3 hours to about 4 hours apart, about 4 hours to about 5 hours apart, about 5 hours to about 6 hours apart, about 6 hours to about 7 hours apart, about 7 hours to about 8 hours apart, about 8 hours to about 9 hours apart, about 9 hours to about 10 hours apart, about 10 hours to about 11 hours apart, about 11 hours to about 12 hours apart, no more than about 24 hours apart or no more than about 48 hours apart.

The dose of CBLB502 is disclosed herein. In general, the dose of any additional agent that is useful is known to those in the art. For example, doses may be determined with reference *Physicians' Desk Reference,* 66th Edition, PDR Network; 2012 Edition (Dec. 27, 2011), the contents of which are incorporated by reference in its entirety. In some embodiment, the present invention allows a patient to receive doses that exceed those determined with reference *Physicians' Desk Reference.*

The dosage of any additional agent described herein can depend on several factors including the severity of the condition, whether the condition is to be treated or prevented, and the age, weight, and health of the human patient to be treated. Additionally, pharmacogenomic (the effect of genotype on the pharmacokinetic, pharmacodynamic or efficacy profile of a therapeutic) information about a particular human patient may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

In another embodiment, delivery can be in a vesicle, in particular a liposome (see Langer, 1990, *Science* 249:1527-1533; Treat et al., in *Liposomes in the Therapy of Infectious Disease and Cancer,* Lopez-Berestein and Fidler (eds.), Liss, New York, pp. 353-365 (1989).

CBLB502 and/or additional agents described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

The dosing regimen of CBLB502 is disclosed herein. The dosage regimen for any additional agent described herein can be selected in accordance with a variety of factors including type, species, age, weight, sex and medical condition of the human patient; the severity of the condition to be treated; the route of administration; the renal or hepatic function of the human patient; the pharmacogenomic makeup of the individual; and the specific compound of the invention employed. CBLB502 (and/or additional agents) described herein can be administered in a single daily dose, or the total daily dosage can be administered in divided doses of two, three or four times daily. Furthermore, CBLB502 (and/or additional agents) described herein can be administered continuously rather than intermittently throughout the dosage regimen.

In some embodiments, the human patient is a pediatric human. In other embodiments, the human patient is an adult human. In other embodiments, the human patient is a geriatric human. As females tend to be more tolerant to radiation, in some embodiments, the human patient is a male.

The invention also provides kits that can simplify the administration of CBLB502 and/or any additional agent described herein. An exemplary kit of the invention comprises CBLB502 and/or any additional agent described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of CBLB502 as disclosed herein and an effective amount of another composition, such as an additional agent as described herein.

In one aspect, the present invention provides a kit suitable for use upon exposure to a high dose of radiation, comprising CBLB502 in a unit dosage form. In some embodiments, the kit comprises CBLB502 in a unit dosage form of about 1 µg to about 50 µg (e.g. about 1, or about 3, or about 5, or about 10, or about 15, or about 20, or about 25, or about 30, or about 35, or about 40, or about 45, or about 45 µg). In some embodiments, the kit further comprises an injection needle (e.g. in a unit dose form, e.g. a pre-loaded (a.k.a. pre-dosed or pre-filled) syringe or a pen needle injector (injection pen)). In some embodiments, the kit comprises CBLB502 which is formulated for intramuscular injection. In some embodiments, the kit comprises CBLB502 (and/or any additional agent) in about 1 to about 3 unit doses. In some embodiments, the present kits further comprise ibuprofen and/or a bottle of water for oral hydration.

In various embodiments, the kit is suitable for military field operations. In various embodiments, the kit further comprises one or more of a radioactivity detector (e.g. a Geiger counter, AN/VDR-2, AN/PDR-77, ADM-300S or a similar device), potassium iodide (KI) or potassium iodate ($KIO_3$) (e.g. liquid (ThyroShield) and the tablet (losat) KI (NUKEPILLS), Rad Block, I.A.A.A.M., No-Rad, Life Extension (LEF), KI4U, NukeProtect, ProKI; doses of which may be about 130 mg), gloves, face mask, hood, and cleaning solutions, optionally comprising hypochlorite; and cleaning wipes.

Definitions

The following definitions are used in connection with the invention disclosed herein. Unless defined otherwise, all technical and scientific terms used herein have the same meaning as commonly understood to one of skill in the art to which this invention belongs.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "additional agent" as used herein is refers to any agent described herein in addition to CBLB502. As used herein, an additional agent refers to an agent that can be used in a combination therapy with CBLB502 or the CBLB502 is administered to a human patient that is undergoing treatment with an additional agent.

An "effective amount," when used in connection with medical uses is an amount that is effective for providing a measurable treatment, prevention, or reduction in the rate of pathogenesis of a disease of interest.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

Generally, for administering therapeutic agents (e.g. CBLB502 (and/or additional agents) described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized. Effective amounts of CBLB502 are disclosed herein.

This invention is further illustrated by the following non-limiting examples.

EXAMPLES

Example 1: Non-Human Primate (NHP) Dosing Study

Healthy adult, male or nonpregnant female rhesus macaques were randomized to receive a single intramuscular dose of 0.0 (n=40), 0.3 (n=20), 1.0 (n=19), 3.0 (n=20), 6.6 (n=20), 10 (n=20), 40 (n=20), or 120 (n=20) μg/kg of CBLB502 (Entolimod) 25 hours after irradiation (7.2 Gy of total body irradiation). No transfusions, systemic antibiotics, fluids, or hematopoietic growth factors were provided.

Figure 2:
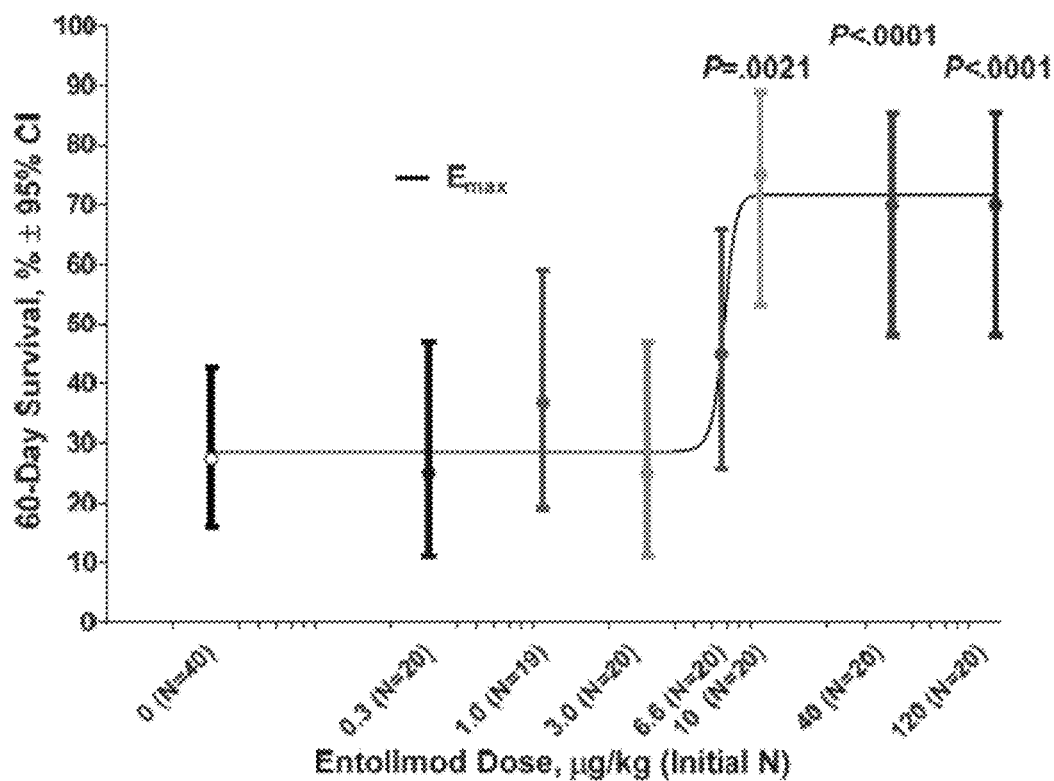
FIG. 2 shows a 60-day survival dose-dependent study.

FIG. 2 shows a 60-day survival dose-dependent study in non-human primates. CBLB502 increased 60-day survival in a dose-dependent manner. The maximal survival benefit was at 10 μg/kg, plateauing across CBLB502 doses of 10 μg/kg (adjusted P=0.0021), 40 μg/kg (adjusted P<0.0001), and 120 μg/kg (nominal P<0.0001). Sixty-day survival was 27.5% in the placebo group and 75.0% in the 10 μg/kg dose group. These data suggest, inter alia, that the effective dose of CBLB502 in non-human primates is greater than at least 3.0 mg/kg.

Example 2: Mitigation of Lethal Acute Radiation Syndrome in Non-Human Primates

Methods:

CBLB502 (aka Entolimod) was expressed in *E. coli* and purified to >98% purity (at SynCo BioPartners, LLC, Amsterdam, The Netherlands) using a validated cGMP process involving 2-step (ion-exchange and hydrophobic interaction) chromatographic purification followed by endotoxin removal with a dedicated ion exchange column. Release testing indicates <100 EU/mg endotoxin, <5 ng/mg residual DNA, and <100 ng/mg host cell protein content in the entolimod drug product. Absence of additional contaminating TLR ligands was confirmed using specific TLR-expressing reporter cell lines (InvivoGen, San Diego, Calif.). The vehicle for entolimod was Dulbecco's Phosphate-Buffered Saline (PBS; Gibco BRL, Life Technologies Inc., Grand Island, N.Y.) in earlier studies and PBS-0.1% Tween 80 (O'Brien Pharmacy, Mission, Kans.) in later studies. Animals received a single injection of entolimod or vehicle in the quadriceps muscle, using a dose volume of 0.2 ml/kg, at 1, 4, 16, 25 or 48 hours after the end of irradiation.

For these studies, 2-5 year old rhesus macaques of both genders that weighed between 3 and 7 kg were used. The animals were research and irradiation naïve, clinically healthy, and certified to be free of specific pathogenic microorganisms (such as *Salmonella* sp., *Shigella* sp., *Mycobacterium tuberculosis*, cercopithecine herpesvirus type I (B virus), and *Toxoplasma gondii*). All animals received helminthicide treatment at their breeding facilities. The care and use of nonhuman primates (*Macaca mulatta*, Chinese subspecies, from Sichuan Province) were in accordance with the principles outlined in the current Guide for the Care and Use of Laboratory Animals published by the National Institutes of Health, and the recommendations of the Weatherall report for The Use of Non-Human Primates in Research (December 2006).

Approximately equal numbers of male and female animals were included in each study group. During the entire observation period (before and after irradiation), animals were housed in individual stainless steel cages in environment-controlled rooms with room temperature of 16-29° C., relative humidity of 30-70%, and a 12 hour light/dark cycle. In addition to fresh fruits and vegetables daily, animals were fed either primate chow or commercial certified primate biscuits. Fresh drinking water was provided ad libitum.

In some irradiation studies, animals received 25 mg/kg pentobarbital sodium in the animal room to achieve mild anesthesia before transportation and an additional 8-10 mg/kg Ketamine injection during transit to the irradiation facility. For irradiation, sedated animals were restrained in plastic irradiation chairs. 5-11 animals were irradiated simultaneously, with balanced inclusion of animals from all study groups in each irradiation cohort. Male and female animals were irradiated separately. Animals were irradiated bilaterally using the cobalt-60 (60Co) gamma-ray sources located at Sichuan Atomic Energy Institute. The first source (used in studies Rs-03, Rs-04, Rs-06, and Rs-08) was a vertical bundle of vertically aligned 60Co rods. The second source (used in studies Rs-09 and Rs-14) was configured as a vertical rectangular array of vertically aligned 60Co rods. Dose rates in different experiments varied from ~0.8 to 1.1 Gy/min (0.94, 0.92, 0.83, 0.73, 1.06 and 1.03 Gy/min for studies Rs-03, Rs-04, Rs-06, Rs-08, Rs-09 and Rs-14, respectively) and animals received a total 6.5-6.75 Gy in-air dose (equivalent to 6.0-6.2 Gy midline dose for ~3-5 kg animals). Individual animal dosimetry was performed using thermoluminescent dosimeter (TLD) sets provided and evaluated by Global Dosimetry Solutions, Inc.

In Study Rs-22, animals were sedated with ketamine (10-20 mg/kg) and placed in plastic restraint boxes for the duration of transport and irradiation. Animals were irradiated using a rotating 6 MV LINAC source (Varian Clinac 2100EX) to a uniform total body in-air dose of 11 Gy, at a dose rate of 0.8±0.025 Gy/min (to achieve a 10.1 Gy midline dose). Dose measurements were made at the center of the cylindrical phantom (diameter=8-10 cm) containing a PTW 31010 0.1cc Semiflex Ion chamber placed on the both sides of each animal. NanoDot dosimeters were used for measurement of individual surface doses.

All animals participating in studies with survival as the primary endpoint were observed for 40 days after total body irradiation (TBI). During this period, cage-side observations were performed two or three times each day, at least 6 hours apart. Signs of morbidity and moribundity were recorded. Blood was repeatedly collected from saphenous or cephalic veins for monitoring of complete blood counts (pre-dose, then almost every day on days 1-15, then every 3-4 days) and cytokine and entolimod levels (pre-dose, then at least at 1, 2, 4, 8, 24 hours post-dose). During blood collection, animals were briefly restrained without sedation. Body weights (at least once per week) and body temperature (at least twice per week) were also recorded. Food and fruit consumption was evaluated daily on a semiquantitative scale (good, fair, or poor). Following irradiation, no intensive individualized supportive care was provided other than oral rehydration, topical anti-infective treatment of lesions and general analgesia with fentanyl patches and/or buprenorphine when deemed necessary by the study veterinarian. No ketamine or opiates known to affect the immune system were used in the study after entolimod treatment. For nutritional support, animals were provided with water soaked biscuits and extra amount of fruit.

Moribund animals were subjected to euthanasia based on pre-specified criteria: severe weight loss (>20% loss of initial weight over a 3-day period); complete anorexia (for >3 days, with signs of deterioration); weakness and inability to obtain food or water (for >24 hours); complete unresponsiveness; low core body temperature (<35.9° C.) following a period of febrile neutropenia; severe rapidly developing acute anemia (<40 g/L hemoglobin, <13% hematocrit, and a drop of ≥7% in hematocrit between consecutive tests); and/or other signs of severe organ system dysfunction with a poor prognosis (as determined by a veterinarian). The euthanasia criteria were based on those generally recommended by veterinarian guidelines for studies involving terminal endpoints with addition of 2 ARS-specific criteria recommended by Armed Forces Radiobiology Research Institute (AFRRI), relating to the rapid onset of acute anemia or drop in core body temperature following a period of febrile neutropenia. Similar criteria for moribund animal euthanasia were also applied by other groups conducting efficacy studies in the NHP model of ARS [27-29, 36, 37]. In studies with survival as the primary endpoint, all animals that survived to day 40 after TBI were subjected to scheduled euthanasia. In studies aimed at evaluation of gastrointestinal (GI) tract morphology, animals were euthanized at 8 hours or 5-7 days after TBI (depending on the study). All animals that were euthanized or found dead were subjected to gross pathology examination, with samples of bone marrow (sternum), spleen, thymus, lymph nodes, and GI tract segments collected for histological examination. In Study Rs-14, bone marrow aspirates were collected from iliac crests for colony forming assays.

General histological analysis of organ samples was performed by light microscopy of paraffin sections (3-5 µm thick, 1-3 per organ or intestinal segment of each animal) stained with hematoxylin-eosin (H&E). Immunohistochemical detection of SOD2 expression, TUNEL staining and EdU incorporation analyses were performed in deparaffinized sections. The following antibodies were used for immunohistochemical evaluation: goat anti-SOD2 (N-20) pAb (sc-18503, Santa Cruz Biotechnology, Santa Cruz, Calif.); mouse anti-smooth muscle actin mAb conjugated with Cy3 (C6198, Sigma-Aldrich, St. Louis, Mo.); rabbit anti-phospho-histone H3 pAb (06-570, Millipore, Billerica, Mass.); and rabbit anti-neuro-specific tubulin beta III pAb (ab18207, Abcam, Cambridge, UK). The following reagents and kits were used histochemical evaluation: ApopTag Fluorescent In Situ Apoptosis Detection Kit (S7110, Chemicon, Millipore, Billerica, Mass.) for TUNEL detection, and azide-modified Alexa Fluor 488 (Invitrogen, Life Technologies, Grand Island, N.Y.) for EdU incorporation. Samples were examined using a Zeiss Axiolmager A1 microscope equipped an epifluorescent light source; images were captured with an AxioCam MRc digital camera and processed with a Zeiss Axio Imager Z1 microscope (Carl Zeiss, Germany).

The extent of morphologic alterations observed in histological sections was assessed by a blind semi-quantitative evaluation.

Analysis of total CFC numbers (which includes CFU-G, CFU-M, CFU-GM, CFU-GEMM, and BFU-E colonies) as well as separate analyses of BFU-E and CFU-Mk were performed using media and reagents from StemCell Technologies according to the manufacturer's instructions (MethoCult, Cat. #28404; MegaCult-C Cat. #28413; StemCell Technologies, Vancouver, Canada). The number of colonies per $10^4$ live cells was calculated.

Complete blood counts (CBC) analysis was performed using automated blood cell counters (at Frontier Biosciences: Cell-Dyn 3700SL, Abbott, USA; at UIC TRL: Advia 120, Siemens Healthcare, USA). Cytokine levels in plasma (using K2EDTA as an anticoagulant) were determined using Luminex multiplex immunological assays at Armed Forces Radiobiology Research Institute (Bethesda, Md.), Baylor Institute for Immunology Research (Dallas, Tex.), or Millipore Corporation (St. Charles, Mo.). In study Rs-03, levels of G-CSF, IL-4, IL-6, IL-10, and IFNγ were analyzed using human-targeted Fluorokine MAP assays from R&D Systems (Minneapolis, Minn.) and levels of IL-2, IL-3, IL-8, IL-12p70, and IP-10 were tested using Upstate (Temecula, Calif.) human-targeted Beadlyte Multi-Cytokine Flex assays. In studies Rs-09 and Rs-14, levels of G-CSF, IL-6, IL-8, and IFNγ were analyzed using Non-Human Primate Cytokine/Chemokine Milliplex Panel from Millipore, Inc. (Billerica, Mass.) and IL-10 was analyzed using human-targeted Fluorokine MAP Luminex assay from R&D Systems (Minneapolis, Minn.).

Entolimod levels in serum or plasma were determined using a sandwich ELISA method employing proprietary entolimod-specific polyclonal antibodies.

For statistical analysis, the numbers of surviving animals (at 40 days after irradiation) were compared pair-wise using Fisher's exact test. Kinetics of mortality was compared between groups by Log rank test. For analysis of the effect of entolimod treatment on survival, the natural logarithm of odds ratio of survival (odds of survival in the treated group divided by that in the control group) was chosen as the metric. The odds associated with a probability p were defined as $p/(1-p)$. For a group of size n with 100% survival, odds were defined as $(n-0.5)/n$; for groups with 0% survival odds were defined as $0.5/n$. Quantitative data were evaluated using Student's t-test. All tests were two-sided. P-values <0.05 were considered statistically significant. Error bars in graphs represent standard errors (unless specified otherwise). GraphPad Prism 5.0 and Microsoft Excel 2007-2010 were used for most statistical analyses.

Calculation of days with Grade 4 cytopenia/anemia: definition of a study day as cytopenic/anemic was based on actual values when available, or on imputed values for days when samples were not collected. Imputation was performed by linear interpolation over time between actual measurements, or by using the last observation carried forward between the day of last available measured value and the day of death. Percentage of live days with Grade 4 cytopenia/anemia was calculated as number of days with cytopenia/anemia divided by number of days the animal was alive during the 40-day observation period.

Area under the curve (AUC) values for cytokine and entolimod levels were calculated using the trapezoid rule. To eliminate the influence of differences in basal cytokine levels, AUC values were background-adjusted by subtracting the minimum observed factor concentration from all other concentrations before calculation.

Figure 3:
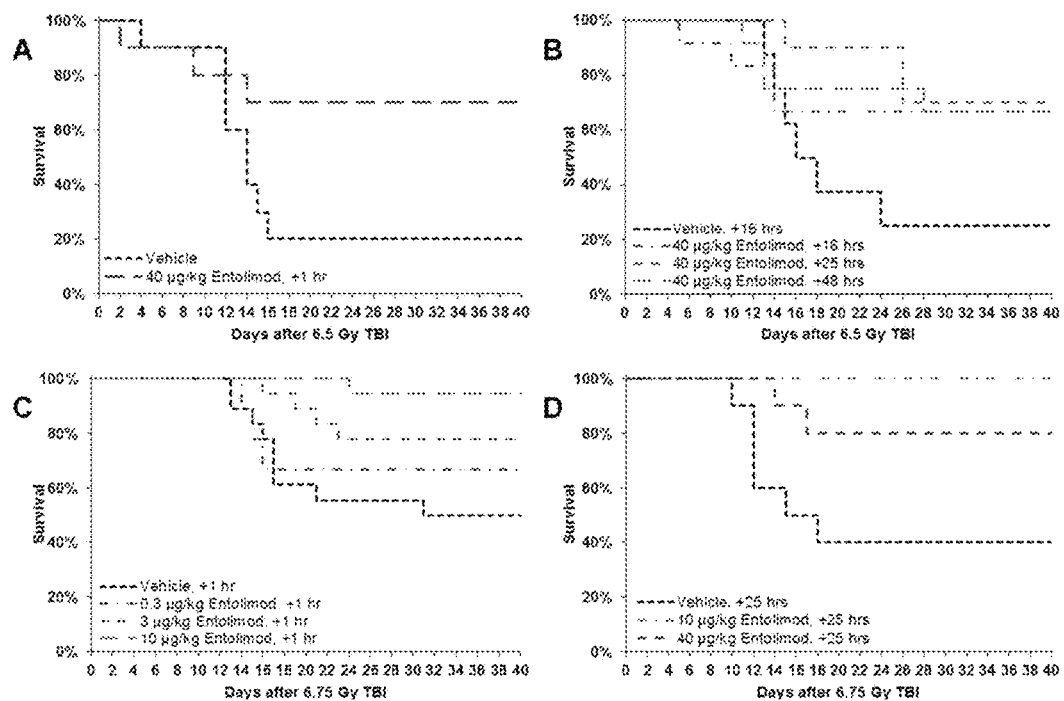
FIG. 3A-D shows improved survival of non-human primates (NHPs) injected with entolimod 1-48 hours after lethal irradiation. Kaplan-Meier plots of non-human primate (NHP) survival over the 40 days following exposure to $LD_{50/40}$-$LD_{75/40}$ doses of total body irradiation (TBI) are shown. Time frame of entolimod efficacy (panels A, B) was evaluated in studies Rs-03 (treatment at 1 hour after $LD_{75/40}$ TBI; N=10) and Rs-06 (treatment at 16, 25, or 48 hours after $LD_{75/40}$ TBI; N=8-12). Dose-dependence of entolimod efficacy (panels C, D) was tested in studies Rs-09 (treatment at 1 hour after $LD_{50/40}$ TBI; N=18) and Rs-14 (treatment at 25 hours after $LD_{50/40}$ TBI; N=10).

Results:

Treatment of NHPs with Entolimod within 48 Hours after Lethal TBI Significantly Reduces the Risk of Death from ARS To investigate the potency of entolimod in increasing survival of NHPs when administered after lethal TBI, a series of non-GLP studies in rhesus macaques were performed using a TBI dose range of $LD_{50/40}$-$LD_{75/40}$ (50-75% lethal over 40 days). This TBI dose range was chosen as being an approximate upper threshold at which exposed individuals would be at substantial risk of death, but might still be salvageable by medical therapy. This study presents the results generated within four survival experiments, designated Rs-03, Rs-06, Rs-09 and Rs-14, involving a total of 164 animals. The study groups for all 4 experiments are shown in Table 1.

respectively, whereas survival in all entolimod-treated groups was 67-75%. Thus, NHP survival was improved by an absolute 42-50% with survival odds ratios ranging from 6 to 9.3 regardless of entolimod administration time within the first 48 hours after TBI (FIG. 3, panels A and B; and Table 1).

The two subsequent studies, Rs-09 and Rs-14, explored dose-dependence of the survival effect of entolimod in NHPs at the boundaries of the 25-hour post-TBI period with the drug injected at either 1 or 25 hours after TBI, respec-

TABLE 1

Efficacy of a single injection of entolimod in increasing 40-day survival of lethally irradiated NHPs when administered at different dose levels within 1-48 hours after TBI

| Study | Irradiation dose | Entolimod dose, μg/kg | Injection time(s) relative to TBI, h | Group size(n) | No. of survivors | % of survivors | Absolute survival increase % | P-value [A] | Survival odds ratio vs. vehicle | Mean survival time ± SE, days | P-value [B] |
|---|---|---|---|---|---|---|---|---|---|---|---|
| Rs-03 | ~$LD_{75/40}$ (6.5 Gy)[C] | 0 (vehicle) | +1 | 10 | 2 | 20% | — | — | — | 18.7 ± 3.7 | — |
|  |  | 40 | +1 | 10 | 7 | 70% | 50% | 0.07 | 9.33 | 30.8 ± 4.8 | 0.06 |
| Rs-06 | ~$LD_{75/40}$ (6.5 Gy)[C] | 0 (vehicle) | +16 | 8 | 2 | 25% | — | — | — | 23.3 ± 3.8 | — |
|  |  | 40 | +16 | 12 | 8 | 67% | 42% | 0.17 | 6.00 | 30.6 ± 4.1 | 0.17 |
|  |  | 40 | +25 | 10 | 7 | 70% | 45% | 0.15 | 7.00 | 35.0 ± 2.7 | 0.02 |
|  |  | 40 | +48 | 12 | 8 | 67% | 42% | 0.17 | 6.00 | 32.4 ± 3.4 | 0.10 |
| Rs-09 | ~$LD_{50/40}$ (6.75 Gy)[D] | 0 (vehicle) | +1 | 18 | 9 | 50% | — | — | — | 29.4 ± 2.7 | — |
|  |  | 0.3 | +1 | 18 | 12 | 67% | 17% | 0.50 | 2.00 | 32.0 ± 2.7 | 0.44 |
|  |  | 3 | +1 | 18 | 14 | 78% | 28% | 0.16 | 3.50 | 35.7 ± 2.0 | 0.07 |
|  |  | 10 | +1 | 18 | 17 | 94% | 44% | 0.007 | 17.00 | 39.2 ± 0.8 | 0.003 |
| Rs-14 | ~$LD_{50/40}$ (6.75 Gy)[D] | 0 (vehicle) | +25 | 10 | 4 | 40% | — | — | — | 24.5 ± 4.3 | — |
|  |  | 10 | +25 | 10 | 10 | 100% | 60% | 0.01 | 28.50[G] | 40.0 ± 0.0 | 0.004 |
|  |  | 40 | +25 | 10 | 8 | 80% | 40% | 0.17 | 6.00 | 35.3 ± 3.1 | 0.06 |
| Pooled vehicle vs. ≥10 μg/kg entolimod, +25 h | ~$LD_{50-75/40}$ (6.5-6.75 Gy) | 0 (vehicle)[E] | +1-+25 | 46 | 17 | 37% | — | — | — | 24.9 ± 1.8 | — |
|  |  | ≥10[F] | +25 | 30 | 25 | 83% | 46% | 0.0001 | 8.53 | 36.8 ± 1.4 | 0.0001 |

[A] P-value by Fisher's exact test (two-tailed) for comparisons vs. vehicle groups within individual studies or in pooled group analysis
[B] P-value by Log rank test (two-tailed) for comparisons vs. vehicle groups within individual studies or in pooled group analysis
[C] Source I: Sichuan Atomic Energy Institute, cylindrical bundle of Co-60 rods
[D] Source II: Sichuan Atomic Energy Institute, vertical array of Co-60 rods
[E] Vehicle-treated animals from studies Rs-03, Rs-06, Rs-09, and Rs-14
[F] Entolimod-treated animals from studies Rs-06 and Rs-14
[G] Survival odds and survival odds ratios adjusted due to 100% survival are shown in italics Note:
The frequency of moribund euthanasia was as follows: Study Rs-03 - 91% (1/11 - found dead), Study Rs-06 - 100%; Study Rs-09 - 85% (3/20 - found dead); Rs-14 - 88% (1/8 - found dead). The likely cause of death in all the non-euthanized animals was acute hemorrhage.

In all of these studies, the effects of intramuscular (i.m.) injection of entolimod were monitored for 40 days after irradiation. In addition to monitoring animal morbidity and mortality, multiple physiological parameters, blood cell counts, levels of elicited cytokines in peripheral blood (pharmacodynamics) and entolimod pharmacokinetics (PK) were evaluated. To prevent suffering, moribund animals were euthanized according to a predefined set of criteria (uniformly used in NHP studies described here). No supportive care was provided other than oral rehydration (drinking water given ad libitum) and non-systemic treatment of external lesions. Study groups were composed of approximately equal numbers of male and female animals. Following irradiation, animals generally developed a clinical picture of ARS with typical prodromal and manifest illness features.

First, in studies Rs-03 and Rs-06, the effective timeframe for radiomitigative efficacy of 40 μg/kg entolimod (a dose previously established as radioprotective in NHPs) was examined. Animals (n=8-12 per group) were irradiated with 6.5 Gy TBI and treated with entolimod at 1, 16, 25, or 48 hours after irradiation. Forty-day survival in vehicle-treated groups was 20% and 25% in studies Rs-03 and Rs-06, tively. Animals (n=10-18 per group) were irradiated with 6.75 Gy TBI (from a different radiation source compared to the two first studies) and received vehicle or entolimod injections at 0.3, 3 or 10 μg/kg (Rs-09) or 10 or 40 μg/kg (Rs-14) dose levels. Forty-day survival in vehicle-treated groups was 50% (Rs-09) or 40% (Rs-14), while entolimod doses of 10-40 μg/kg were fully efficacious in rescuing 80-100% of irradiated NHPs. These data correspond to increases in survival of 40-60% with survival odds ratios ranging between 6 and 28.5. Entolimod treatment at 3 μg/kg provided partial efficacy (28% survival increase) and the lowest tested dose of 0.3 μg/kg showed little or no efficacy (17% survival increase) (FIG. 3, panels C and D; and Table 1).

The survival advantage of 40-60% provided by efficacious entolimod doses was uniformly observed across all four of the studies reported here, although statistical significance was not reached in some individual groups (probably due to their small size). Similarity of study design elements, treatment regimens, and animal populations allowed meta-analysis in which similarly treated groups were pooled. Pooling of vehicle-treated groups from all 4 studies (n=46) resulted in 37% 40-day survival, while pooling of all groups treated with fully efficacious 10 and 40 µg/kg entolimod doses at 25 hours after TBI (n=30) indicated 83% 40-day survival. This 46% increase in 40-day survival was highly statistically significant (P=0.0001 by Fisher's exact test) with a survival odds ratio of 8.5 (Table 1).

The kinetics of mortality was similar in all 4 studies, with the majority of deaths occurring on days 12-16 after TBI and no deaths occurring after day 30. Mean survival time ranged from 18.7±3.7 to 29.4±2.7 days in vehicle-treated groups (24.9±1.8 days with all vehicle-treated groups pooled), while after 10 µg/kg entolimod treatment, mean survival time substantially increased to a range of 30.6±4.1 to 40.0±0.0 days (36.8±1.4 days in pooled group analysis; P=0.0001 by Log-rank test for difference in survival kinetics) (FIG. 3 and Table 1).

Entolimod Treatment Accelerates Recovery of Hematopoiesis in Lethally Irradiated NHPs Radiation damage to the hematopoietic (HP) system is one of the major causes of lethality at ~$LD_{50}$-$LD_{70}$ doses of TBI. Therefore, to investigate the mechanisms underlying entolimod's radiomitigative efficacy, the content of different hematopoietic cell types was examined in peripheral blood and bone marrow samples collected in the four NHP studies described above.

Figure 4:
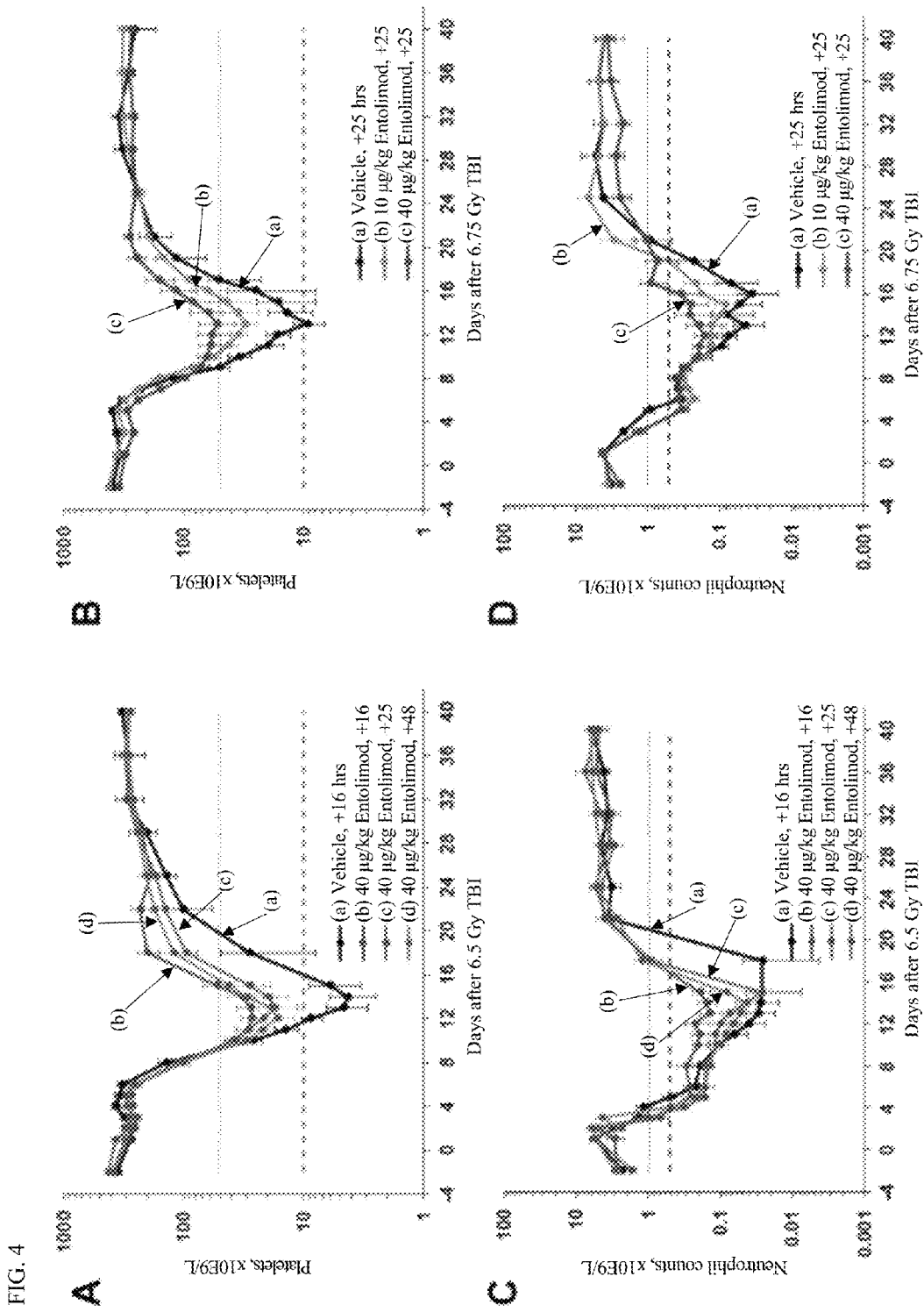
FIG. 4A-H shows accelerated hematological recovery of peripheral blood in NHPs injected with entolimod 16-48 hours post-irradiation. NHPs were treated with a single injection of entolimod at 16-48 hours after $LD_{50/40}$ or $LD_{75/40}$ TBI. Panels A, C, E, G: Effect of 40 μg/kg entolimod administered at different time points (16, 25 or 48 hours) after 6.5 Gy TBI ($LD_{75/40}$; study Rs-06; N=8-12). Panels B, D, F, H: Effect of different entolimod doses (10 or 40 μg/kg) administered at 25 hours after 6.75 Gy TBI ($LD_{75/40}$; study Rs-14; N=10). Cytopenia/anemia thresholds: dotted lines—Grade 3 (platelets <50,000/μL; neutrophils <1,000/μL; hemoglobin <80 g/L); dashed lines—Grade 4 (platelets <10,000/μL; neutrophils <500/μL; hemoglobin <65 g/L). Error bars represent standard errors.
Figure 4:
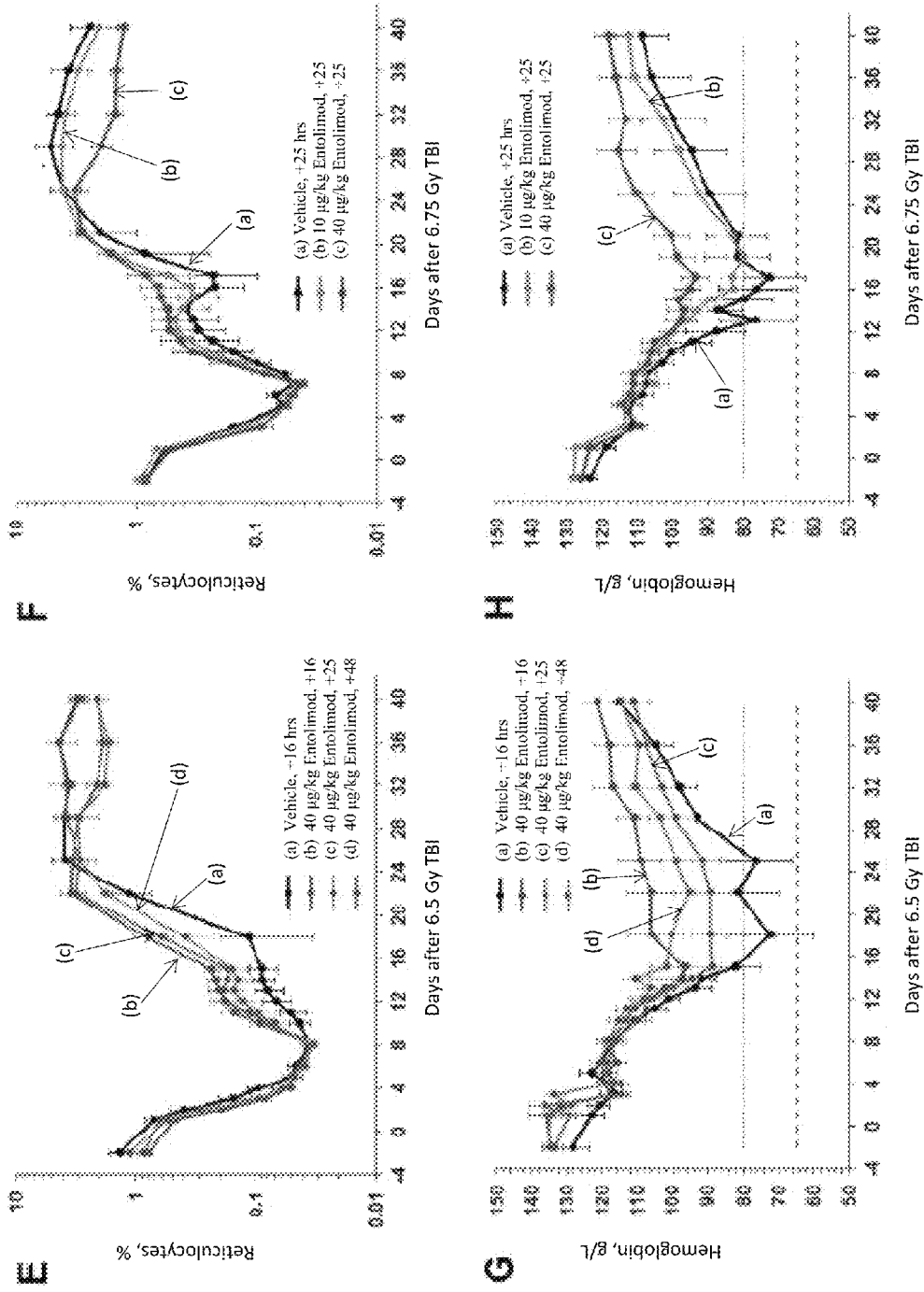
Figure 5:
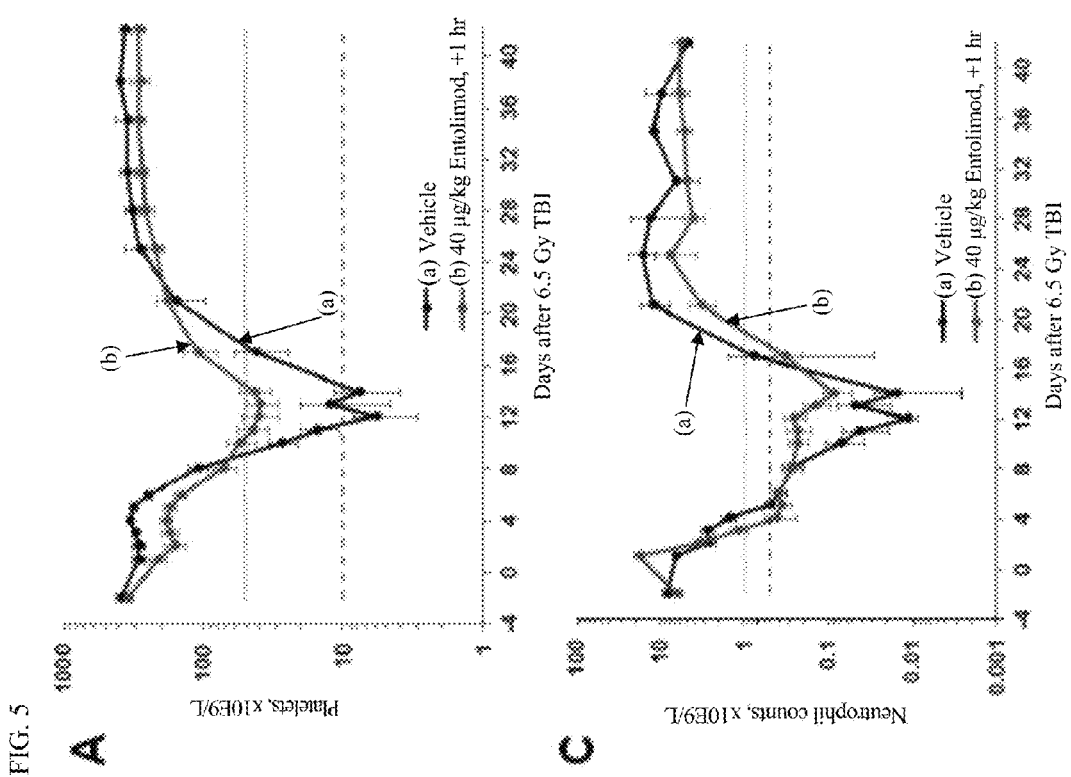
FIG. 5A-H shows accelerated recovery of the peripheral blood cellularity and hemoglobin content in NHPs irradiated with $LD_{50/40}$ or $LD_{75/40}$ of TBI and treated with different doses of entolimod 1 hour later. Panels A, C, E, G: study Rs-03; N=10. Panels B, D, F, H: study Rs-09; N=18. Cytopenia/anemia thresholds: dotted lines—Grade 3 (platelets <50,000/μL; neutrophils <1,000/μL; hemoglobin <80 g/L); dashed lines—Grade 4 (platelets <10,000/μL; neutrophils <500/μL; hemoglobin <65 g/L). Error bars represent standard errors.
Figure 5:
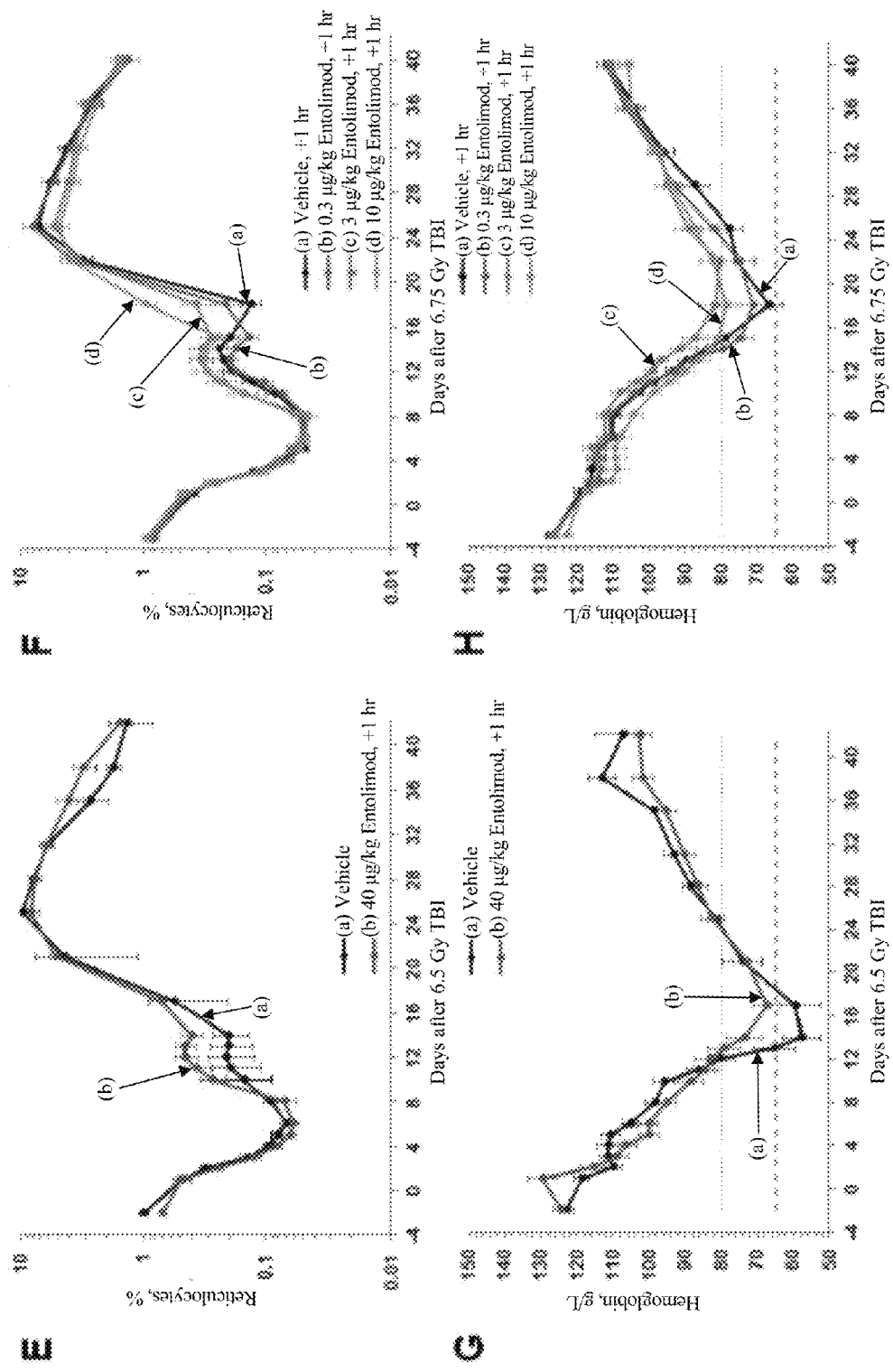

Comparison of hematology data from control lethally irradiated NHPs and those treated with a single injection of entolimod revealed that across all four studies, the efficacious drug doses of ≥10 µg/kg reduced the duration and severity of thrombocytopenia, neutropenia, and anemia when given at any tested time point within 1-48 hours post-TBI (FIG. 4, panels A-D, G-H; FIG. 5, panels A-D, G-H; Tables 2-6).

TABLE 2

Mean nadir values of neutrophils, platelets and hemoglobin in peripheral blood following total body irradiation and vehicle or entolimod treatment

| Study | Irradiation dose | Entolimod dose, µg/kg | Injection time(s) relative to TBI, h | Group size (n) | Neutrophils Mean nadir ± SE ($\times 10^3$/µL) | P-value[A] | Platelets Mean nadir ± SE ($\times 10^3$/µL) | P-value[A] | Hemoglobin Mean nadir ± SE (g/L) | P-value[A] |
|---|---|---|---|---|---|---|---|---|---|---|
| Rs-03 | ~$LD_{75/40}$ (6.5 Gy)[B] | 0 (vehicle) | +1 | 10 | 0.01 ± 0.005 | — | 31 ± 27.9 | — | 59.8 ± 7.4 | — |
|  |  | 40 | +1 | 10 | 0.18 ± 0.128 | 0.20 | 59.6 ± 26.2 | 0.46 | 77.8 ± 6.9 | 0.09 |
| Rs-06 | ~$LD_{75/40}$ (6.5 Gy)[B] | 0 (vehicle) | +16 | 8 | 0.01 ± 0.011 | — | 3.2 ± 1.7 | — | 72.5 ± 5.4 | — |
|  |  | 40 | +16 | 12 | 0.06 ± 0.017 | 0.05 | 34 ± 16.4 | 0.09 | 92.9 ± 7.4 | 0.04 |
|  |  | 40 | +25 | 10 | 0.02 ± 0.007 | 0.51 | 15.8 ± 5.9 | 0.07 | 83.3 ± 5.4 | 0.18 |
|  |  | 40 | +48 | 12 | 0.02 ± 0.005 | 0.85 | 12.5 ± 4.6 | 0.08 | 93.1 ± 3.2 | 0.01 |
| Rs-09 | ~$LD_{50/40}$ (6.75 Gy)[C] | 0 (vehicle) | +1 | 18 | 0.01 ± 0.001 | — | 8 ± 1.4 | — | 66.1 ± 3.7 | — |
|  |  | 0.3 | +1 | 18 | 0.01 ± 0.003 | 0.44 | 7.2 ± 1.2 | 0.66 | 69.1 ± 3.5 | 0.56 |
|  |  | 3 | +1 | 18 | 0.02 ± 0.006 | 0.02 | 16.6 ± 3.7 | 0.04 | 78.9 ± 4.1 | 0.03 |
|  |  | 10 | +1 | 18 | 0.03 ± 0.009 | 0.01 | 22.4 ± 3.9 | 0.002 | 76.7 ± 3.7 | 0.05 |
| Rs-14 | ~$LD_{50/40}$ (6.75 Gy)[C] | 0 (vehicle) | +25 | 10 | 0.01 ± 0.006 | — | 6.8 ± 2.4 | — | 60.2 ± 7.6 | — |
|  |  | 10 | +25 | 10 | 0.04 ± 0.011 | 0.11 | 21.8 ± 5.4 | 0.03 | 77.5 ± 3.8 | 0.06 |
|  |  | 40 | +25 | 10 | 0.07 ± 0.029 | 0.09 | 39.9 ± 12.4 | 0.03 | 89.6 ± 4.4 | 0.005 |
| Pooled vehicle vs. ≥10 µg/kg entolimod, +25 h | ~$LD_{50-75/40}$ (6.5-6.75 Gy) | 0 (vehicle)[D] | +1-+25 | 46 | 0.01 ± 0.003 | — | 11.9 ± 6.1 | — | 64.6 ± 2.9 | — |
|  |  | ≥10[E] | +25 | 30 | 0.04 ± 0.011 | 0.006 | 25.9 ± 5.1 | 0.08 | 83.5 ± 2.7 | <0.0001 |

[A] P-value by Student's t-test (two-tailed) for comparisons vs. vehicle groups within individual studies or in pooled group analysis
[B] Source I: Sichuan Atomic Energy Institute, cylindrical bundle of Co60 rods
[C] Source II: Sichuan Atomic Energy Institute, vertical array of Co60 rods
[D] Vehicle-treated animals from studies Rs-03, Rs-06, Rs-09, and Rs-14
[E] Entolimod-treated animals from studies Rs-06 and Rs-14

TABLE 3

S1 Table. Incidence and duration of Grade 4 neutropenia (neutrophil count <500 cells/µL) in lethally irradiated NHPs treated with vehicle or entolimod

| Study | Irradiation dose | Entolimod dose, µg/kg | Injection time(s) relative to TBI, h | Group size (n) | Mean % live days ± SE with Grade 4 neutropenia | P-value[A] | Incidence of Grade 4 neutropenia | P-value[B] |
|---|---|---|---|---|---|---|---|---|
| Rs-03 | ~$LD_{75/40}$ (6.5 Gy)[C] | 0 (vehicle) | +1 | 10 | 56% ± 6% | — | 100% | — |
|  |  | 40 | +1 | 10 | 33% ± 6% | 0.01 | 90% | >0.05 |
| Rs-06 | ~$LD_{75/40}$ (6.5 Gy)[C] | 0 (vehicle) | +16 | 8 | 60% ± 6% | — | 100% | — |
|  |  | 40 | +16 | 12 | 47% ± 6% | 0.13 | 100% | >0.05 |
|  |  | 40 | +25 | 10 | 44% ± 6% | 0.08 | 100% | >0.05 |
|  |  | 40 | +48 | 12 | 51% ± 8% | 0.35 | 100% | >0.05 |
| Rs-09 | ~$LD_{50/40}$ (6.75 Gy)[D] | 0 (vehicle) | +1 | 18 | 51% ± 4% | — | 100% | — |
|  |  | 0.3 | +1 | 18 | 48% ± 5% | 0.65 | 100% | >0.05 |
|  |  | 3 | +1 | 18 | 44% ± 4% | 0.22 | 100% | >0.05 |
|  |  | 10 | +1 | 18 | 38% ± 2% | 0.01 | 100% | >0.05 |
| Rs-14 | ~$LD_{50/40}$ (6.75 Gy)[D] | 0 (vehicle) | +25 | 10 | 55% ± 6% | — | 100% | — |
|  |  | 10 | +25 | 10 | 37% ± 2% | 0.01 | 100% | >0.05 |
|  |  | 40 | +25 | 10 | 42% ± 5% | 0.11 | 100% | >0.05 |

TABLE 3-continued

S1 Table. Incidence and duration of Grade 4 neutropenia (neutrophil count <500 cells/μL) in lethally irradiated NHPs treated with vehicle or entolimod

| Study | Irradiation dose | Entolimod dose, μg/kg | Injection time(s) relative to TBI, h | Group size (n) | Mean % live days ± SE with Grade 4 neutropenia | P-value[A] | Incidence of Grade 4 neutropenia | P-value[B] |
|---|---|---|---|---|---|---|---|---|
| Pooled vehicle vs. ≥10 μg/kg entolimod, +25 h | ~LD$_{50\text{-}75/40}$ (6.5-6.75 Gy) | 0 (vehicle)[E] ≥10[F] | +1-+25 +25 | 46 30 | 55% ± 3% 41% ± 3% | — 0.001 | 100% 100% | — >0.05 |

[A]P-value by Student's t-test (two-tailed) against vehicle groups in individual studies or in pooled group analysis
[B]P-value by Fisher's exact test (two-tailed) against vehicle groups in individual studies or in pooled group analysis
[C]Source I: Sichuan Atomic Energy Institute, cylindrical bundle of Co-60 rods
[D]Source II: Sichuan Atomic Energy Institute, vertical array of Co-60 rods
[E]Vehicle-treated animals from studies Rs-03, Rs-06, Rs-09, and Rs-14
[F]Entolimod-treated animals from studies Rs-06 and Rs-14

TABLE 4

S2 Table. Incidence and duration of absolute neutropenia (neutrophil count <10 cells/μL) in lethally irradiated NHPs treated with vehicle or entolimod

| Study | Irradiation dose | Entolimod dose, μg/kg | Injection time(s) relative to TBI, h | Group size (n) | Mean % live days ± SE with absolute neutropenia | P-value[A] | Incidence of absolute neutropenia | P-value[B] |
|---|---|---|---|---|---|---|---|---|
| Rs-03 | ~LD$_{75/40}$ (6.5 Gy)[C] | 0 (vehicle) 40 | +1 +1 | 10 10 | 16% ± 4% 1% ± 1% | — 0.002 | 80% 0% | — 0.001 |
| Rs-06 | ~LD$_{75/40}$ (6.5 Gy)[C] | 0 (vehicle) 40 40 40 | +16 +16 +25 +48 | 8 12 10 12 | 15% ± 3% 3% ± 2% 6% ± 2% 8% ± 3% | — 0.01 0.03 0.11 | 88% 25% 50% 50% | — 0.02 >0.05 >0.05 |
| Rs-09 | ~LD$_{50/40}$ (6.75 Gy)[D] | 0 (vehicle) 0.3 3 10 | +1 +1 +1 +1 | 18 18 18 18 | 10% ± 2% 11% ± 3% 7% ± 2% 4% ± 1% | — 0.74 0.39 0.02 | 78% 72% 50% 56% | — >0.05 >0.05 >0.05 |
| Rs-14 | ~LD$_{50/40}$ (6.75 Gy)[D] | 0 (vehicle) 10 40 | +25 +25 +25 | 10 10 10 | 6% ± 2% 2% ± 1% 5% ± 3% | — 0.19 0.84 | 50% 30% 50% | — >0.05 >0.05 |
| Pooled vehicle vs. ≥10 μg/kg entolimod, +25 h | ~LD$_{50\text{-}75/40}$ (6.5-6.75 Gy) | 0 (vehicle)[E] ≥10[F] | +1-+25 +25 | 46 30 | 11% ± 1% 4% ± 1% | — 0.0003 | 74% 43% | — 0.01 |

[A]P-value by Student's t-test (two-tailed) against vehicle groups in individual studies or in pooled group analysis
[B]P-value by Fisher's exact test (two-tailed) against vehicle groups in individual studies or in pooled group analysis
[C]Source I: Sichuan Atomic Energy Institute, cylindrical bundle of Co-60 rods
[D]Source II: Sichuan Atomic Energy Institute, vertical array of Co-60 rods
[E]Vehicle-treated animals from studies Rs-03, Rs-06, Rs-09, and Rs-14
[F]Entolimod-treated animals from studies Rs-06 and Rs-14

TABLE 5

S3 Table. Incidence and duration of Grade 4 thrombocytopenia (platelet count <10,000 cells/μL) in lethally irradiated NHPs treated with vehicle or entolimod

| Study | Irradiation dose | Entolimod dose, μg/kg | Injection time(s) relative to TBI, h | Group size (n) | Mean % live days ± SE with Grade 4 thrombocytopenia | P-value[A] | Incidence of Grade 4 thrombocytopenia | P-value[B] |
|---|---|---|---|---|---|---|---|---|
| Rs-03 | ~LD$_{75/40}$ (6.5 Gy)[C] | 0 (vehicle) 40 | +1 +1 | 10 10 | 20% ± 4% 2% ± 1% | — 0.003 | 80% 20% | — 0.02 |
| Rs-06 | ~LD$_{75/40}$ (6.5 Gy)[C] | 0 (vehicle) 40 40 40 | +16 +16 +25 +48 | 8 12 10 12 | 26% ± 5% 6% ± 3% 11% ± 4% 13% ± 4% | — 0.003 0.02 0.04 | 88% 33% 60% 58% | — 0.03 >0.05 >0.05 |
| Rs-09 | ~LD$_{50/40}$ (6.75 Gy)[D] | 0 (vehicle) 0.3 3 10 | +1 +1 +1 +1 | 18 18 18 18 | 9% ± 2% 9% ± 2% 5% ± 2% 3% ± 2% | — 0.89 0.09 0.03 | 72% 67% 44% 28% | — >0.05 >0.05 0.02 |

TABLE 5-continued

S3 Table. Incidence and duration of Grade 4 thrombocytopenia (platelet count <10,000 cells/μL) in lethally irradiated NHPs treated with vehicle or entolimod

| Study | Irradiation dose | Entolimod dose, μg/kg | Injection time(s) relative to TBI, h | Group size (n) | Mean % live days ± SE with Grade 4 thrombocytopenia | P-value[A] | Incidence of Grade 4 thrombocytopenia | P-value[B] |
|---|---|---|---|---|---|---|---|---|
| Rs-14 | ~LD$_{50/40}$ (6.75 Gy)[D] | 0 (vehicle) | +25 | 10 | 20% ± 5% | — | 80% | — |
|  |  | 10 | +25 | 10 | 2% ± 1% | 0.004 | 40% | >0.05 |
|  |  | 40 | +25 | 10 | 4% ± 2% | 0.01 | 30% | >0.05 |
| Pooled vehicle vs. ≥10 μg/kg entolimod, +25 h | ~LD$_{50-75/40}$ (6.5-6.75 Gy) | 0 (vehicle)[E] | +1-+25 | 46 | 17% ± 2% | — | 78% | — |
|  |  | ≥10[F] | +25 | 30 | 5% ± 2% | <0.0001 | 43% | 0.003 |

[A]P-value by Student's t-test (two-tailed) against vehicle groups in individual studies or in pooled group analysis
[B]P-value by Fisher's exact test (two-tailed) against vehicle groups in individual studies or in pooled group analysis
[C]Source I: Sichuan Atomic Energy Institute, cylindrical bundle of Co60 rods
[D]Source II: Sichuan Atomic Energy Institute, vertical array of Co60 rods
[E] Vehicle-treated animals from studies Rs-03, Rs-06, Rs-09, and Rs-14
[F]Entolimod-treated animals from studies Rs-06 and Rs-14

TABLE 6

S4 Table. Incidence and duration of Grade 4 anemia (hemoglobin level <65 g/L) in lethally irradiated NHPs treated with vehicle or entolimod

| Study | Irradiation dose | Entolimod dose, μg/kg | Injection time(s) relative to TBI, h | Group size (n) | Mean % live days ± SE with Grade 4 anemia | P-value[A] | Incidence of Grade 4 anemia | P-value[B] |
|---|---|---|---|---|---|---|---|---|
| Rs-03 | ~LD$_{75/40}$ (6.5 Gy)[C] | 0 (vehicle) | +1 | 10 | 11% ± 3% | — | 70% | — |
|  |  | 40 | +1 | 10 | 6% ± 3% | 0.29 | 20% | >0.05 |
| Rs-06 | ~LD$_{75/40}$ (6.5 Gy)[C] | 0 (vehicle) | +16 | 8 | 8% ± 5% | — | 25% | — |
|  |  | 40 | +16 | 12 | 2% ± 2% | 0.25 | 8% | >0.05 |
|  |  | 40 | +25 | 10 | 6% ± 4% | 0.78 | 20% | >0.05 |
|  |  | 40 | +48 | 12 | 1% ± 1% | 0.20 | 0% | >0.05 |
| Rs-09 | ~LD$_{50/40}$ (6.75 Gy)[D] | 0 (vehicle) | +1 | 18 | 9% ± 3% | — | 44% | — |
|  |  | 0.3 | +1 | 18 | 7% ± 2% | 0.49 | 33% | >0.05 |
|  |  | 3 | +1 | 18 | 6% ± 3% | 0.50 | 17% | >0.05 |
|  |  | 10 | +1 | 18 | 6% ± 3% | 0.41 | 17% | >0.05 |
| Rs-14 | ~LD$_{50/40}$ (6.75 Gy)[D] | 0 (vehicle) | +25 | 10 | 12% ± 4% | — | 60% | — |
|  |  | 10 | +25 | 10 | 1% ± 1% | 0.01 | 20% | >0.05 |
|  |  | 40 | +25 | 10 | 1% ± 1% | 0.02 | 10% | >0.05 |
| Pooled vehicle vs. ≥10 μg/kg entolimod, +25 h | ~LD$_{50-75/40}$ (6.5-6.75 Gy) | 0 (vehicle)[E] | +1-+25 | 46 | 10% ± 2% | — | 50% | — |
|  |  | ≥10[F] | +25 | 30 | 3% ± 2% | 0.003 | 17% | 0.004 |

[A]P-value by Student's t-test (two-tailed) against vehicle groups in individual studies or in pooled group analysis
[B]P-value by Fisher's exact test (two-tailed) against vehicle groups in individual studies or in pooled analysis
[C]Source I: Sichuan Atomic Energy Institute, cylindrical bundle of Co60 rods
[D]Source II: Sichuan Atomic Energy Institute, vertical array of Co60 rods
[E] Vehicle-treated animals from studies Rs-03, Rs-06, Rs-09, and Rs-14
[F]Entolimod-treated animals from studies Rs-06 and Rs-14

In the context of ARS, anemia should be interpreted as a result of hemorrhage exacerbated by radiation-imposed suppression of compensating erythropoiesis (FIG. 4, panels E and F; and FIG. 5., panels E and F) since mature erythrocytes are radioresistant and their life span in the circulation of NHPs is 60 days.

Although small group sizes reduced the statistical significance of the effects in some individual cases, the positive trends indicating entolimod-mediated amelioration of HP ARS were clearly observed in all reported studies (Tables 2-6). In pooled group analysis (analogous to that described for survival), entolimod effects were highly statistically significant. Thus, nadir neutrophil counts were increased by entolimod treatment from 0.01±0.003×10$^3$/μl to 0.04±0.011×10$^3$/μl (P=0.006), nadir platelet counts—from 11.9±6.1×10$^3$/μl to 25.9±5.1×10$^3$/μl (P=0.08), and nadir hemoglobin levels—from 64.6±2.9×10$^3$/μl to 83.5±2.7×10$^3$/μl (P<0.0001) (Table 2). At the same time, the proportion of live days (when a particular animal was alive and had cytopenia) with Grade 4 neutropenia (neutrophil counts <500/μl) was decreased by entolimod treatment from 55%±3% in vehicle-treated groups to 41%±3% (P=0.001, Table 3), with Grade 4 thrombocytopenia (platelet counts <10,000/μl)—from 17%±2% to 5%±2% (P<0.0001, Table 5), and with Grade 4 anemia (hemoglobin level <65 g/L)—from 10%±2% to 3%±2% (P=0.003, Table 6). While entolimod treatment did not change the incidence of Grade 4 neutropenia (proportion of animals that developed this condition at least once during 40 days of observation), it reduced the incidence of Grade 4 thrombocytopenia from 78% in vehicle-treated groups to 43% (pooled group analysis, P=0.003, Table 5), and of Grade 4 anemia—from 50% in control groups to 17% (pooled group analysis, P=0.004, Table 6). In addition to decreased severity and duration of thrombocytopenia, accelerated recovery of erythropoiesis in entolimod-treated NHPs (FIG. 4, panels E and F; and FIG. 5, panels E and F) also contributed to markedly decreased incidence of ARS-associated Grade 4 anemia. Unlike the survival endpoint, where saturation of entolimod's effect was achieved at dose of 10 µg/kg (FIG. 3, panels C and D), the effect of entolimod on hematological parameters continued to improve between 10 and 40 µg/kg doses (FIG. 4, panels B, D, F and H). This is consistent with the notion that achieving certain threshold levels (for example, above Grade 4 cytopenias/anemia) is sufficient to support survival.

Figure 6:
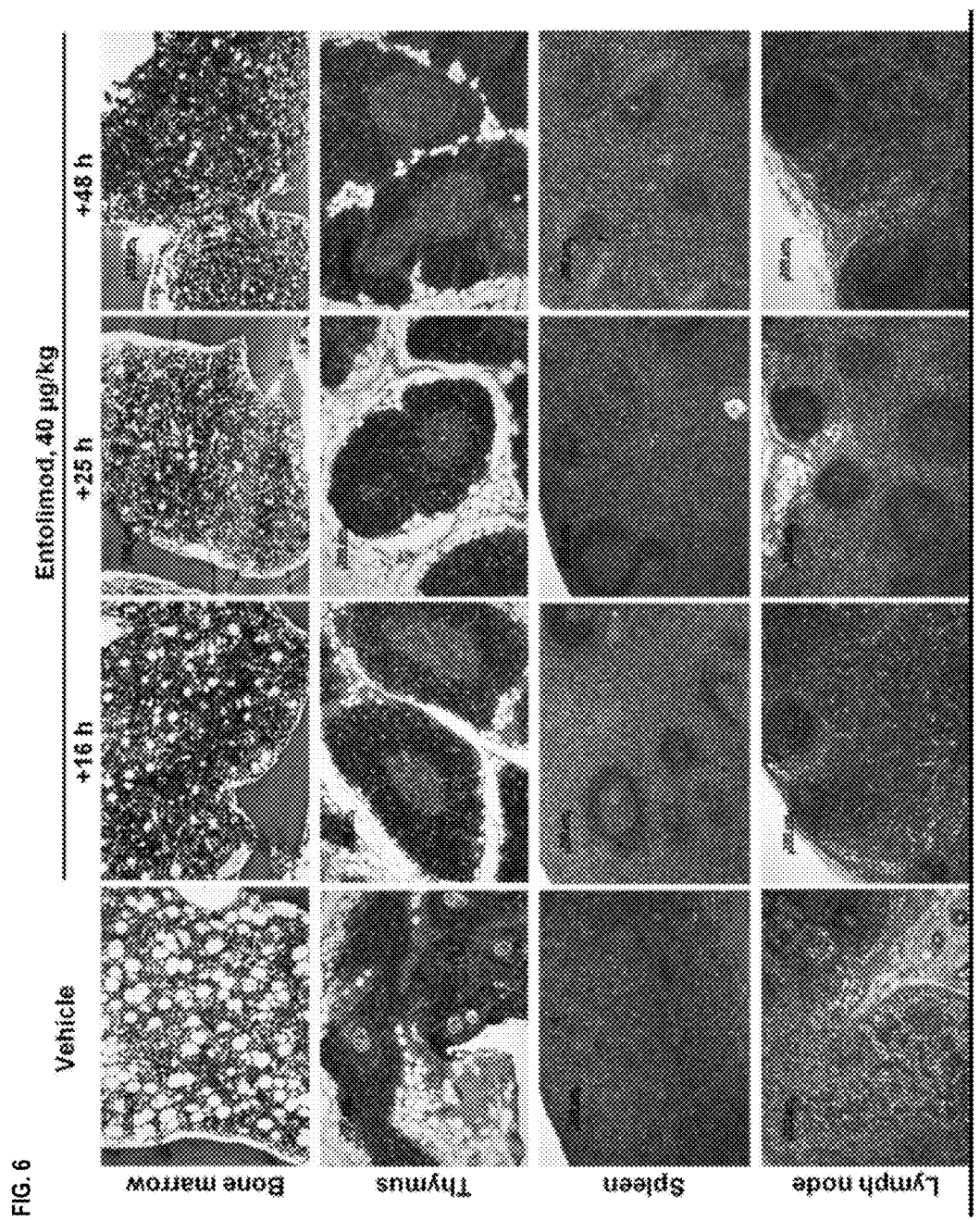
FIG. 6 shows enhanced morphological recovery of hematopoietic and lymphoid organs in NHPs treated with entolimod post-irradiation. NHPs were treated with a single injection of 40 μg/kg entolimod 16, 25 or 48 hours after $LD_{75/40}$ total body irradiation (TBI). Tissue morphology was assessed 40 days post-irradiation and compared to that in control NHPs treated with vehicle 16 hours after $LD_{75/40}$ TBI. Representative histological images (hematoxylin-eosin staining) of sternum bone marrow sections, thymuses, spleens and mesenteric lymph nodes of animals that survived to study termination on Day 40 post-TBI (study Rs-06) are shown. Scale bars: 100 μm for bone marrow, 200 μm for thymus, spleen, and lymph node.

Consistent with the finding of accelerated recovery of blood cellularity after hematopoietic nadirs in entolimod-treated irradiated NHPs, the bone marrow (BM) of treated animals displayed accelerated morphological recovery. Analysis of hematoxylin-eosin-stained sternum sections collected from surviving NHPs at 40 days post-TBI showed that BM from animals given a single injection of 40 µg/kg entolimod within 48 hours after TBI was considerably better regenerated compared to control monkeys. The hematopoietic cells were not only numerous, but also densely arranged in clusters among the sinusoids and the inconspicuous fat component. The elements of the three hematopoietic lineages (granulocytic, erythroid, and megakaryocytic) were spread out and in close contact with each other. In some animals, BM morphology was normal or close to normal, although others still had slightly or moderately hypoplastic BM. In contrast, BM of control NHPs was clearly less cellular and contained more adipose elements. Accelerated morphological recovery in entolimod-treated NHPs was also observed in lymphoid organs, including thymus, spleen and lymph nodes (FIG. 6). These differences were statistically significant when blindly assigned semi-quantitative histological scores were compared (Table 7). Similar effects were induced by a single injection of 10 µg/kg entolimod administered at 25 hours after TBI (FIG. 7; and Table 8).

TABLE 7

Histological evaluation of hematopoietic/lymphoid organs from NHPs that survived to day 40 after 6.5 Gy TBI and vehicle or entolimod treatment (study Rs-06)

| | Mean score [A] ± SE | | | P-value vs. vehicle [B] | | |
| | | Entolimod, 40 µg/kg | | | | |
| | Vehicle | 16 h | 25 h | 48 h | Entolimod, 40 µg/kg | | |
| Organ/tissue | (N = 2) | (N = 8) | (N = 7) | (N = 8) | 16 h | 25 h | 48 h |
| Bone marrow | 1.3 ± 0.3 | 3.4 ± 0.1 | 3.6 ± 0.2 | 3.4 ± 0.2 | 0.04 | 0.01 | 0.02 |
| Thymus | 1.0 ± 0.0 | 2.4 ± 0.5 | 2.6 ± 0.5 | 2.3 ± 0.4 | 0.02 | 0.02 | 0.02 |
| Spleen | 1.0 ± 0.0 | 2.0 ± 0.3 | 1.7 ± 0.4 | 1.5 ± 0.2 | 0.01 | 0.14 | 0.03 |
| Lymph node | 1.0 ± 0.0 | 1.6 ± 0.3 | 1.9 ± 0.3 | 2.0 ± 0.2 | 0.05 | 0.02 | 0.001 |

[A] Scoring was performed based on a 5-grade scale developed for each organ: 0 - total aplasia; 1 - pronounced atrophy, 2 - moderate atrophy, 3 - slight atrophy, close to normal morphology; 4 - normal morphology. Scoring criteria for individual organs are described in Supporting Information, S1 Methods.
[B] Student's t-test vs. vehicle, 2-tailed.

TABLE 8

Semi-quantitative histological evaluation of hematopoietic/lymphoid organs from NHPs that survived to day 40 after 6.75 Gy TBI followed by vehicle or entolimod treatment (study Rs-14)

| | Mean score [A] ± SE | | | P-value vs. vehicle [B] | |
| | | Entolimod, +25 h | | | |
| | | 10 | 40 | Entolimod, +25 h | |
| | Vehicle | µg/kg | µg/kg | 10 | 40 |
| Organ/tissue | (N = 4) | (N = 10) | (N = 8) | µg/kg | µg/kg |
| Bone marrow | 2.2 ± 0.7 | 3.7 ± 0.1 | 3.9 ± 0.0 | 0.1 | 0.1 |
| Thymus [C] | 2.1 ± 0.1 | 3.5 ± 0.2 | 3.8 ± 0.1 | 0.007 | 0.002 |
| Spleen | 1.0 ± 0.3 | 2.7 ± 0.2 | 3.6 ± 0.1 | 0.004 | 0.001 |
| Lymph node | 1.2 ± 0.2 | 2.3 ± 0.3 | 3.7 ± 0.1 | 0.007 | 0.0003 |

[A] Scoring was performed based on a 5-grade scale developed for each organ: 0 - total aplasia; 1 - pronounced atrophy, 2 - moderate atrophy, 3 - slight atrophy, close to normal morphology; 4 - normal morphology. Scoring criteria for individual organs are described in Supplementary Methods.
[B] Student's t-test vs. vehicle, 2-tailed.
[C] Due to thymus atrophy, fewer thymus samples were evaluated compared to other organs (N = 2, 4, and 6 for vehicle, 10 µg/kg, and 40 µg/kg groups, respectively).

Figure 8:
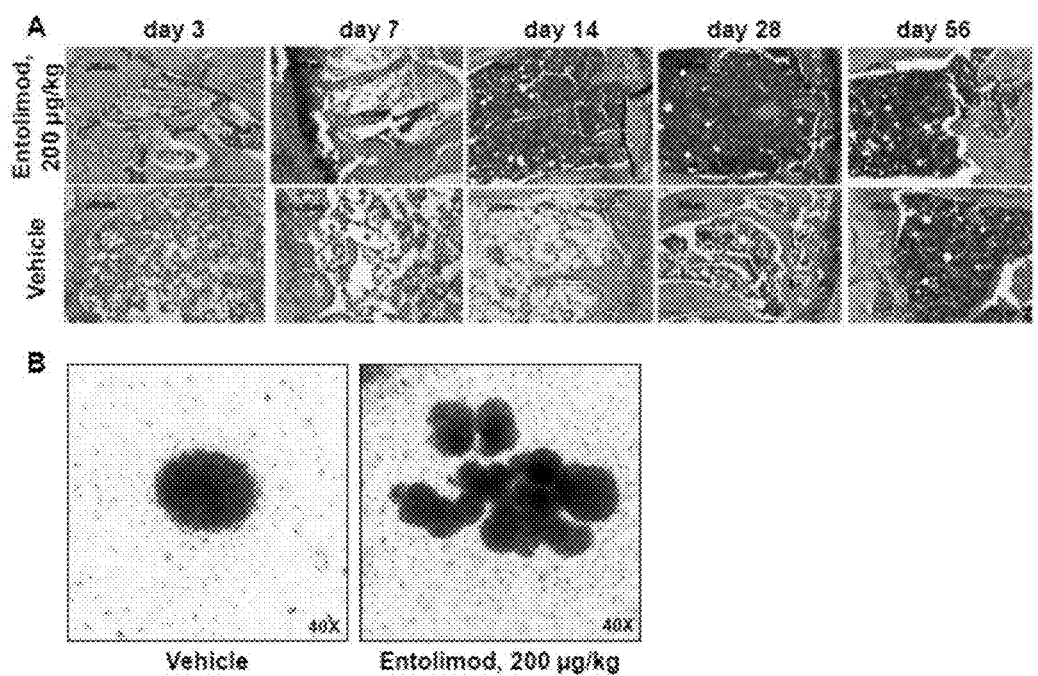
FIG. 8A-B shows accelerated kinetics of bone marrow regeneration and proliferating phenotype of CFU-GM colonies in entolimod-treated CD2F1 mice after $LD_{50/30}$ of TBI and entolimod treatment. Male CD2F1 mice were irradiated with 9 Gy TBI and injected i.m. with vehicle or 200 μg/kg entolimod 25 h later. Groups of 5 mice were sacrificed at the indicated time points for evaluation of histopathology and bone marrow clonogenic potential. Panel A: Representative microphotographs of hematoxylin-eosin-stained bone marrow sections. Scale bar—100 μm. Panel B: Appearance of CFU-GM colonies grown from bone marrow collected on day 7 after TBI.

To investigate the kinetics of entolimod-elicited BM recovery in more detail, a dedicated study was performed in which mice were injected with vehicle or entolimod 25 hours after 9 Gy TBI (~$LD_{50/30}$) and then euthanized for histological and other evaluations at different time points. As shown in FIG. 8, panel A, the first histological signs of active hematopoiesis were evident in the BM of entolimod-treated mice as early as 3 days after TBI (2 days after drug treatment), with full-scale hematopoiesis observed by day 14. In comparison, the onset of hematopoietic recovery in vehicle-treated mice occurred between post-irradiation days 14 and 28, and full-scale hematopoiesis was further shifted to a time interval between days 28 and 56. Interestingly, the first signs of hematopoiesis in the BM of entolimod-treated mice were localized to the trabecular cell lining, suggesting stimulation of the HP stem cell compartment by entolimod. Indeed, as early as 7 days after TBI, very early granulo-monocytic progenitors (CFU-GM colonies) from entolimod-treated mice were elevated in number and displayed increased proliferative potential compared to those from vehicle-treated mice (FIG. 8, panel B).

Analysis of BM aspirates obtained from NHPs on day 40 after exposure to 6.75 Gy TBI and treated with either vehicle (n=4) or 40 µg/kg entolimod (n=4) 25 hours later revealed a clear positive influence of the drug on the content of hematopoietic progenitor cells, including total colony forming cells (CFC), erythroid burst forming units (BFU-E), and megakaryocyte colony forming units (CFU-Mk) (granulocyte lineage progenitors were not separately analyzed). The most substantial entolimod-elicited effect was on CFU-Mk, for which the frequency per $10^4$ viable BM cells was increased ~4.8-fold from 0.34±0.11 in vehicle-treated animals to 1.63±0.05 (P<0.05). The frequencies of CFC and BFU-E in entolimod-treated animals were increased by 22% and 36%, respectively, compared to vehicle-treated controls. The observed dominance of entolimod's effect on CFU-Mk compared to progenitors of other lineages at this late time point (40 days after TBI) may be due to differences in the kinetics of recovery of different HP lineages, with the thrombopoietic lineage being known for its slow restoration following BM ablation and transplantation compared to other lineages.

Taken together, these data demonstrate, inter alia, that entolimod is a potent mitigator of radiation injury in the HP system, and acts via stimulation of accelerated hematopoietic recovery.

Entolimod Treatment Reduces Initial Damage in the GI Tract and Accelerates its Regeneration in Lethally Irradiated NHPs Acute high-dose irradiation sufficient to induce GI ARS results in high degrees of apoptosis in the GI tract mucosa and submucosal elements (lamina propria, mucosa muscularis, lymphoid accumulations), leading to atrophy, increased permeability, susceptibility to hemorrhage (especially on the background of thrombocytopenia) and/or intussusceptions. Histological analyses were used to evaluate the effects of entolimod treatment on these signs of radiation damage to the NHP GI tract.

Assessment of NHP GI histology at 40 days after $LD_{50-75/40}$ TBI doses did not reveal substantial differences between surviving entolimod- or vehicle-treated irradiated animals (Table 9), most likely due to near-completion of regeneration by this late post-TBI time point regardless of treatment. Nevertheless, mean histological scores were generally higher in entolimod-treated groups compared to vehicle-treated control groups (Table 9). This radiomitigative/pro-regeneration effect of entolimod was most apparent in the radiosensitive small intestine and was observed in all histological substructures of the GI tract (villi and/or surface epithelium; crypts; and lamina propria with submucosa). The level of radiomitigation was moderate in the cecum and minimal to nonexistent in the colon and rectum, where radiation injury was not prominent (as observed in histological analysis of samples from animals that died during the course of the study).

TABLE 9

Semi-quantitative histological evaluation of GI tract segments from NHPs that survived to day 40 after 6.5 Gy TBI and vehicle or entolimod treatment (study Rs-06)

| | Mean score [A] ± SE | | | | P-value vs. vehicle [B] | | |
|---|---|---|---|---|---|---|---|
| | | Entolimod, 40 µg/kg | | | Entolimod, 40 µg/kg | | |
| | Vehicle | +16 h | +25 h | +48 h | | | |
| Organ/tissue | (N = 2) | (N = 8) | (N = 7) | (N = 8) | 16 h | 25 h | 48 h |
| Duodenum | 2.4 ± 0.1 | 3.1 ± 0.2 | 2.9 ± 0.2 | 3.2 ± 0.1 | 0.03 | 0.07 | 0.01 |
| Jejunum | 2.8 ± 0.3 | 3.8 ± 0.1 | 3.6 ± 0.1 | 3.6 ± 0.1 | 0.21 | 0.24 | 0.25 |
| Ileum | 3.3 ± 0.3 | 3.6 ± 0.1 | 3.6 ± 0.1 | 3.7 ± 0.1 | 0.35 | 0.36 | 0.31 |
| Cecum | 2.8 ± 0.2 | 3.5 ± 0.1 | 3.6 ± 0.1 | 3.4 ± 0.1 | 0.11 | 0.05 | 0.10 |
| Colon | 3.6 ± 0.3 | 3.5 ± 0.1 | 3.3 ± 0.1 | 3.5 ± 0.1 | 0.71 | 0.46 | 0.76 |
| Rectum | 3.0 ± 0.7 | 3.0 ± 0.2 | 3.0 ± 0.2 | 3.4 ± 0.2 | 0.98 | 0.98 | 0.64 |

[A] 0: severely abnormal; 1: markedly abnormal; 2: moderately abnormal; 3: mildly abnormal; 4: normal (see Supplementary Methods). Sample-average scores were calculated for each sample over evaluated histological sub-structures (villi/epithelium, crypts, lamina propria/submucosa, Brunner's glands). Mean sample-average scores per group are shown.
[B] Student's t-test vs. vehicle, 2-tailed.

To assess the effect of entolimod on the GI component of ARS during the peak of GI damage, three additional dedicated NHP studies were designed (Table 10). In these studies, irradiated animals (a total of 48 NHPs, equal numbers of males and females) were euthanized at different time points between 8 hours and 7 days after TBI, when signs of immediate and early radiation-induced GI damage are typically observed along with indications of the initiation of recovery processes. The animals received TBI doses sufficient to induce moderate to severe GI injury (6.5-11 Gy, expected to cause 70-100% mortality) and entolimod doses ranging between 0.3 and 40 µg/kg at 1 to 25 hours after TBI. Some animals received EdU injections prior to euthanasia to allow evaluation of crypt proliferation by visualization of EdU incorporation on histological sections.

TABLE 10

Layout of studies dedicated to assessment of entolimod effects on GI tract histopathology in the course of ARS

| Study Number | Irradiation dose and source | Entolimod dose, µg/kg | Injection time relative to TBI, h | Group size | Timing of scheduled euthanasia (after TBI) |
|---|---|---|---|---|---|
| Rs-04 | ~$LD_{75/40}$ (6.5 Gy); Co60[A] | 0 (vehicle) | +1 | 2 | 8 h |
| | | 40 | +1 | 2 | 8 h |
| | | 0 (vehicle) | +1 | 2 | 5 d |
| | | 40 | +1 | 2 | 5 d |
| Rs-08 | ~$LD_{75/40}$ (6.5 Gy); Co60[A] | 0 (vehicle) | +1 | 2 | 8 h |
| | | 3 | +1 | 2 | 8 h |
| | | 10 | +1 | 2 | 8 h |
| | | 40 | +1 | 4 | 8 h |
| | | 100 | +1 | 2 | 8 h |
| | | 200 | +1 | 2 | 8 h |
| | | 0 (vehicle) | +1 | 2 | 5 d |
| | | 3 | +1 | 2 | 5 d |
| | | 10 | +1 | 2 | 5 d |
| | | 40 | +1 | 4 | 5 d |
| | | 100 | +1 | 2 | 5 d |
| | | 200 | +1 | 2 | 5 d |
| | | 40 | +16 | 2 | 5 d |
| | | 40 | +25 | 2 | 5 d |

TABLE 10-continued

Layout of studies dedicated to assessment of entolimod effects on GI tract histopathology in the course of ARS

| Study Number | Irradiation dose and source | Entolimod dose, µg/kg | Injection time relative to TBI, h | Group size | Timing of scheduled euthanasia (after TBI) |
|---|---|---|---|---|---|
| Rs-22 | >LD$_{75/40}$ (11 Gy); LINAC[B] | 0 (vehicle) 40 | +4 +4 | 4 4 | 7 d[C] 7 d[C] |

Figure 9:
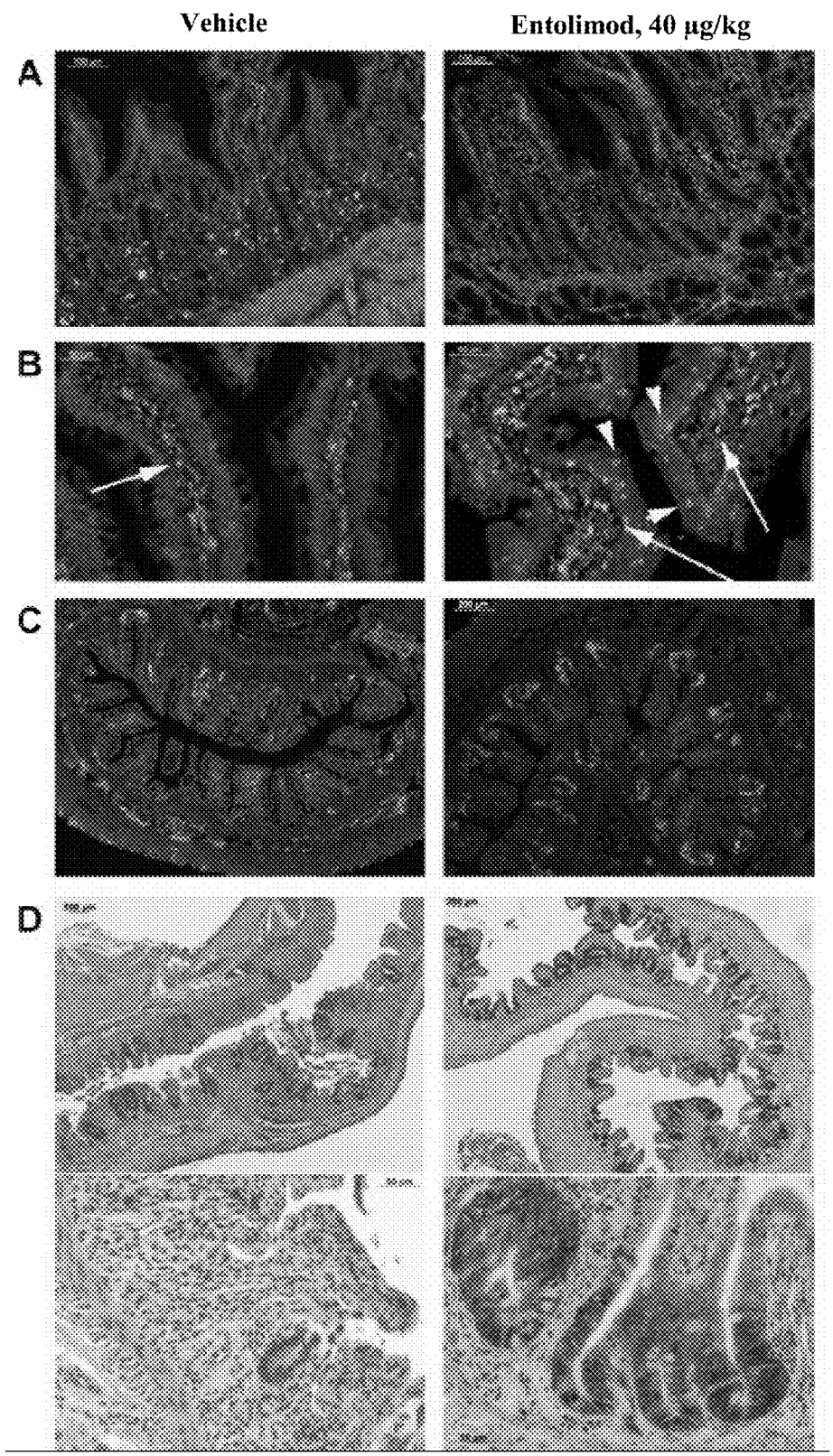
FIG. 9A-D shows entolimod treatment ameliorates radiation damage in the gastrointestinal (GI) tract. Panels A, B: Small intestine sections from NHPs 8 hours after exposure to 6.5 Gy TBI and treatment with vehicle or 40 μg/kg entolimod 1 h later (study Rs-04). Blue—DAPI nuclear staining, red—smooth muscle actin immunostaining. Panel A: TUNEL staining showing fewer apoptotic cells (green) in GI crypts of entolimod-treated NHPs (scale bar 100 μm); Panel B: SOD2 immunostaining (green) showing more positive cells in GI villi (arrowheads) and lamina propria (arrows) of entolimod-treated NHPs (scale bar 50 μm). Panels C, D: Small intestine sections of NHPs 7 days after exposure to 11 Gy TBI and treatment with vehicle or 40 μg/kg entolimod 4 h later (study Rs-22). Panel C: Visualization of proliferating cells in the jejunum crypts: EdU (10 mg/kg i.v. 1 h before euthanasia) inclusion in replicating DNA (green) and phosphohistone 3 immunostaining of mitotic cells (red) showing more intensive proliferation of GI crypts in entolimod-treated NHPs (scale bar—200 μm). Panel D: H&E staining of ileum sections: upper panels—low magnification (scale bar—200 μm), lower panels—high magnification (scale bar—50 μm).
Figure 10:
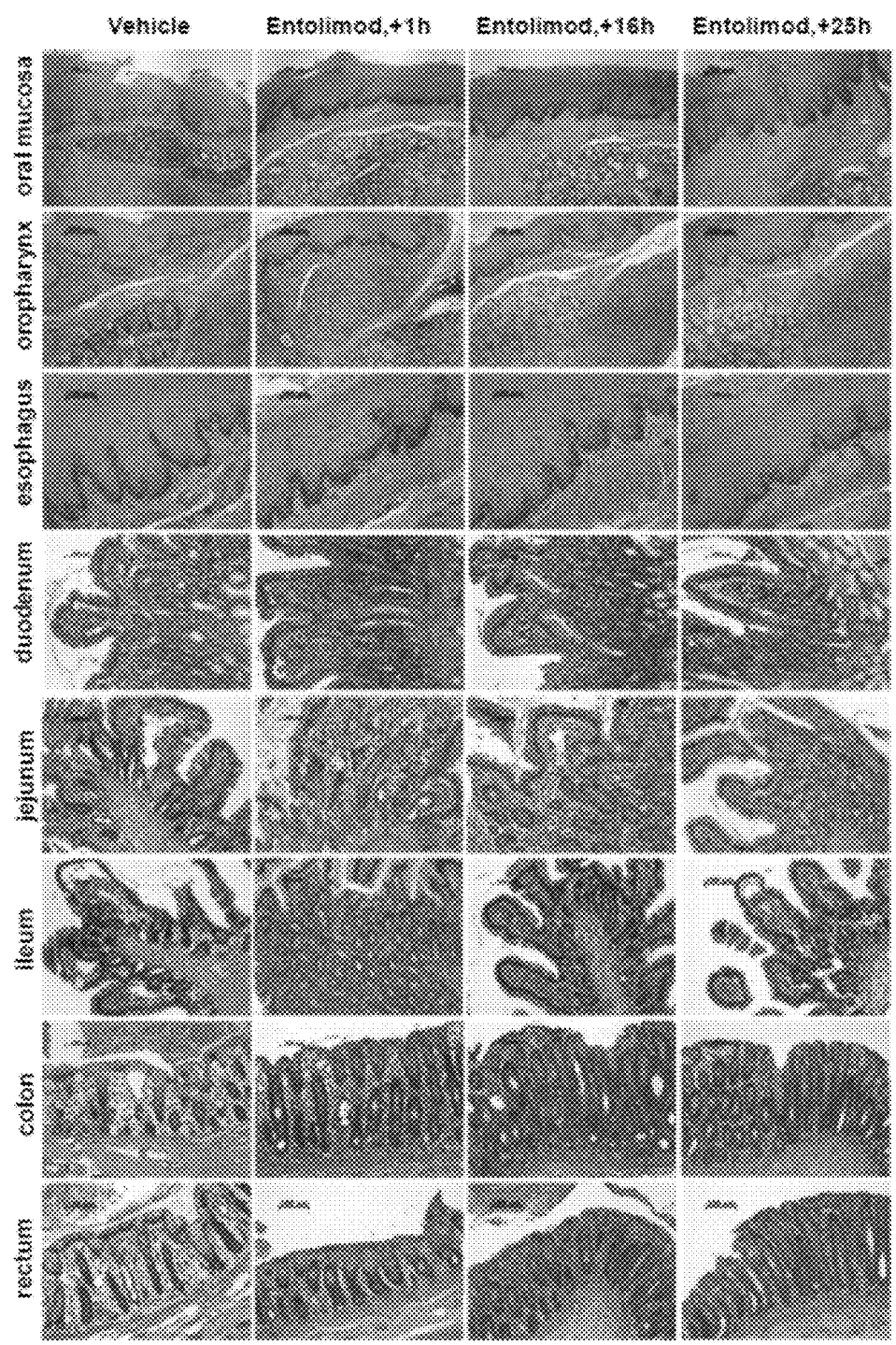
FIG. 10 shows improved GI tract morphology in NHPs irradiated with 6.5 Gy TBI and treated with a single injection of entolimod at 1, 16, or 25 hours later. Rhesus macaques were injected i.m. with vehicle or 40 μg/kg entolimod 1, 16 or 25 h after 6.5 Gy TBI (study Rs-08). Samples were collected on day 5 after TBI for H&E staining. Scale bars—200 μm for oral mucosa and oropharynx; 100 μm—for all other GI tract segments.
Figure 11:
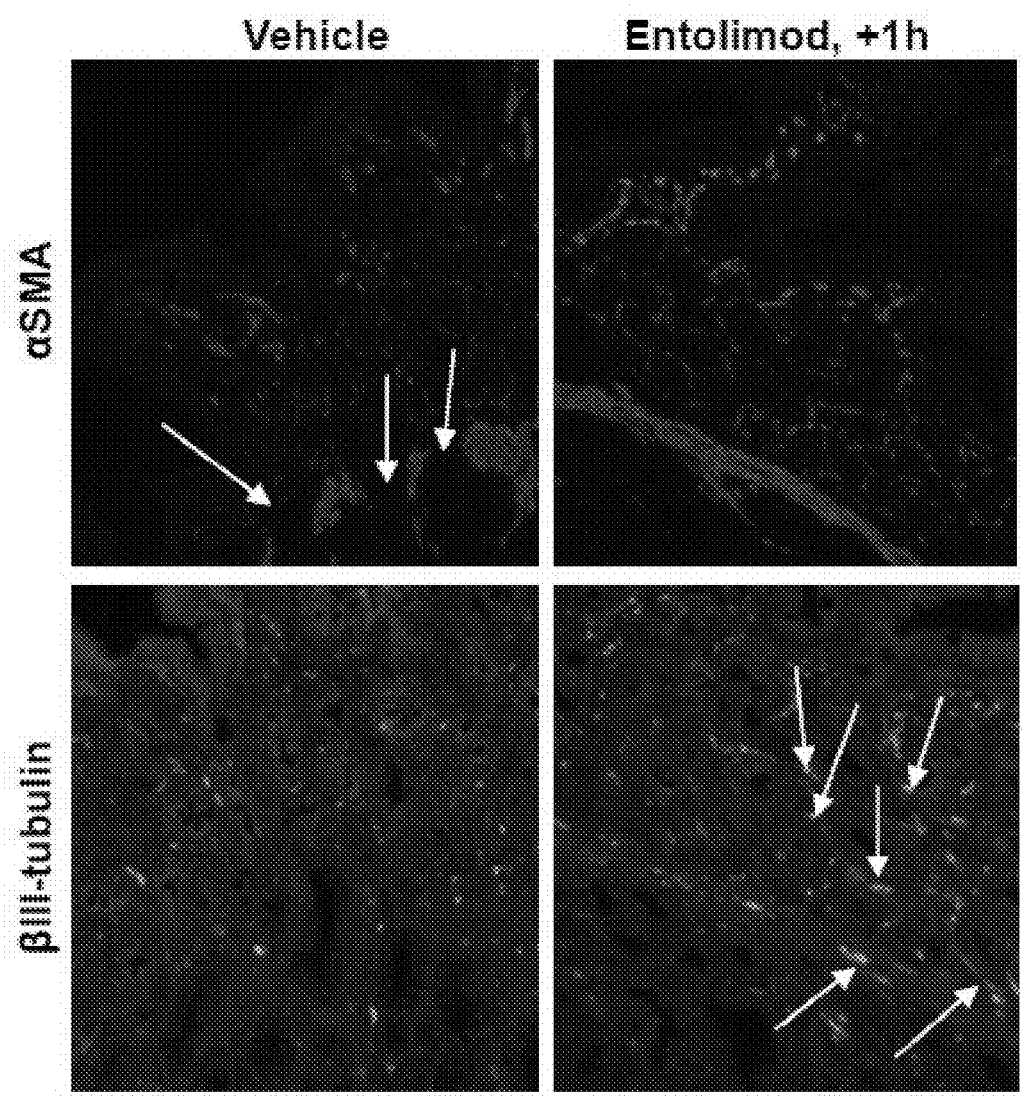
FIG. 11 shows improved preservation of intestinal innervation and muscularis mucosae integrity in the GI tract of irradiated NHPs treated with entolimod 1 hour after 6.5 Gy TBI. Rhesus macaques were injected i.m. with vehicle or 40 μg/kg entolimod 1 h after 6.5 Gy TBI and duodenum samples were collected 5 days later (study Rs-08). Upper panels: arrows point to disruptions of muscularis mucosae (red)—present mostly in vehicle-treated NHPs. Bottom panels: arrows point to axons and neural termini (green) in the cryptal area of the small intestine—more abundant in entolimod-treated NHPs.

[A]Source I: Sichuan Atomic Energy Institute, cylindrical bundle of cobalt rods
[B]Source III: UIC TRL, 6 MV LINAC source (Varian Clinac 2100EX)
[C]10 mg/kg EdU, i.v. 1 h before euthanasia At 8 hours after 6.5 Gy TBI, the number of apoptotic cells counted in ~200 small intestine crypts was ~4.2-fold lower in animals treated with entolimod 1 hour after TBI (~1.16 TUNEL-positive cells/crypt) compared to vehicle-treated animals (~4.74 TUNEL-positive cells/crypt) (FIG. 9, panel A). There were only a few apoptotic cells in the crypts of the large intestine and rectum (~0.3 cells/crypt) regardless of treatment. Administration of entolimod also resulted in more robust expression of the NF-κB-regulated anti-oxidant enzyme SOD2 in small intestine villi, crypts and lamina propria (FIG. 9, panel B). Entolimod-treated (1 hour after TBI) NHPs showed improved morphology in all analyzed GI segments at 5 days after exposure to 6.5 Gy TBI compared to vehicle-treated controls (FIG. 10). In addition to showing improved preservation/recovery of intestinal villi, crypts, and lymphoid accumulations in the lamina propria, entolimod-treated animals demonstrated better preservation of elements of the intestinal nervous system and muscularis mucosa (FIG. 11). The mitigative effect of entolimod on radiation-induced injury to the GI tract was inversely proportional to the time interval between irradiation and drug administration, but was still clearly observed even when the drug was given 25 hours after TBI (FIG. 10). At 7 days after 11 Gy TBI, irradiated and entolimod-treated (40 µg/kg, at 4 hours after TBI) NHPs, unlike vehicle-treated animals, demonstrated massive crypt regeneration as indicated by robust EdU incorporation (FIG. 9, panel C) and tissue morphology (microcolony growth visible by light microscopy, FIG. 9, panel D). Parallel semiquantitative blind histological assessment of radiation injury in different tissue elements throughout the small and large intestines showed statistically significant differences, indicating a beneficial effect of entolimod treatment (Table 11 and Table 12).

TABLE 11

Histological evaluation of GI tract segments on day 7 after 11 Gy TBI and vehicle or 40 µg/kg entolimod treatment at +4 hours (study Rs-22, N = 4/group)

| GI segment | Vehicle score [A], mean ± SE | Entolimod score [A], mean ± SE | T-test P-value (E vs. V) [B] |
|---|---|---|---|
| Oral Mucosa | 0.9 ± 0.03 | 1.5 ± 0.06 | 0.001 |
| Esophagus | 1.1 ± 0.03 | 1.7 ± 0.09 | 0.01 |
| Stomach | 1.1 ± 0.05 | 2.3 ± 0.08 | 0.0001 |
| Duodenum | 1.0 ± 0.05 | 1.6 ± 0.03 | 0.0004 |
| Jejunum | 0.9 ± 0.07 | 1.3 ± 0.12 | 0.05 |
| Ileum | 1.1 ± 0.07 | 1.3 ± 0.02 | 0.04 |
| Cecum | 1.1 ± 0.07 | 1.3 ± 0.03 | 0.08 |
| Ascending Colon | 0.9 ± 0.17 | 1.5 ± 0.15 | 0.05 |
| Transverse Colon | 1.0 ± 0.17 | 1.4 ± 0.02 | 0.08 |
| Descending Colon | 0.9 ± 0.19 | 1.3 ± 0.03 | 0.12 |
| Rectum | 1.1 ± 0.03 | 1.2 ± 0.05 | 0.15 |

[A] 0: severely abnormal; 1: markedly abnormal; 2: moderately abnormal; 3: mildly abnormal; 4: normal (see Supporting Information, S1 Methods).
[B] Student's t-test of entolimod (E) vs. vehicle (V) scores, 2-tailed

TABLE 12

Semi-quantitative histological evaluation of GI tract sub-structures on day 7 after 11 Gy TBI and vehicle or 40 ug/kg entolimod treatment at 4 h post-TBI (study Rs-22, N = 4)

| Intestinal structure | Vehicle score [A], mean ± SE | 40 µg/kg Entolimod score [A], mean ± SE | T-test P-value (E vs. V) [B] |
|---|---|---|---|
| MALT [C] | 1.0 ± 0.03 | 1.4 ± 0.04 | <0.0001 |
| Lamina Propria | 1.0 ± 0.04 | 1.3 ± 0.03 | <0.0001 |
| Surface Epithelium | 1.1 ± 0.06 | 1.4 ± 0.03 | <0.0001 |
| Crypts | 1.1 ± 0.07 | 1.4 ± 0.06 | <0.0001 |
| Villi | 0.9 ± 0.09 | 1.3 ± 0.06 | <0.0001 |

[A] 0: severely abnormal; 1: markedly abnormal; 2: moderately abnormal; 3: mildly abnormal; 4: normal (see Supplementary Methods).
[B] Student's t-test of 40 µg/kg entolimod (E) vs. vehicle (V) scores, 2-tailed.
[C] Mucosa-associated lymphoid tissue.

Without wishing to be bound by theory, it is believed that entolimod effectively mitigates radiation injury to the GI system, likely acting via reduction of apoptosis and stimulation of regeneration.

Figure 12:
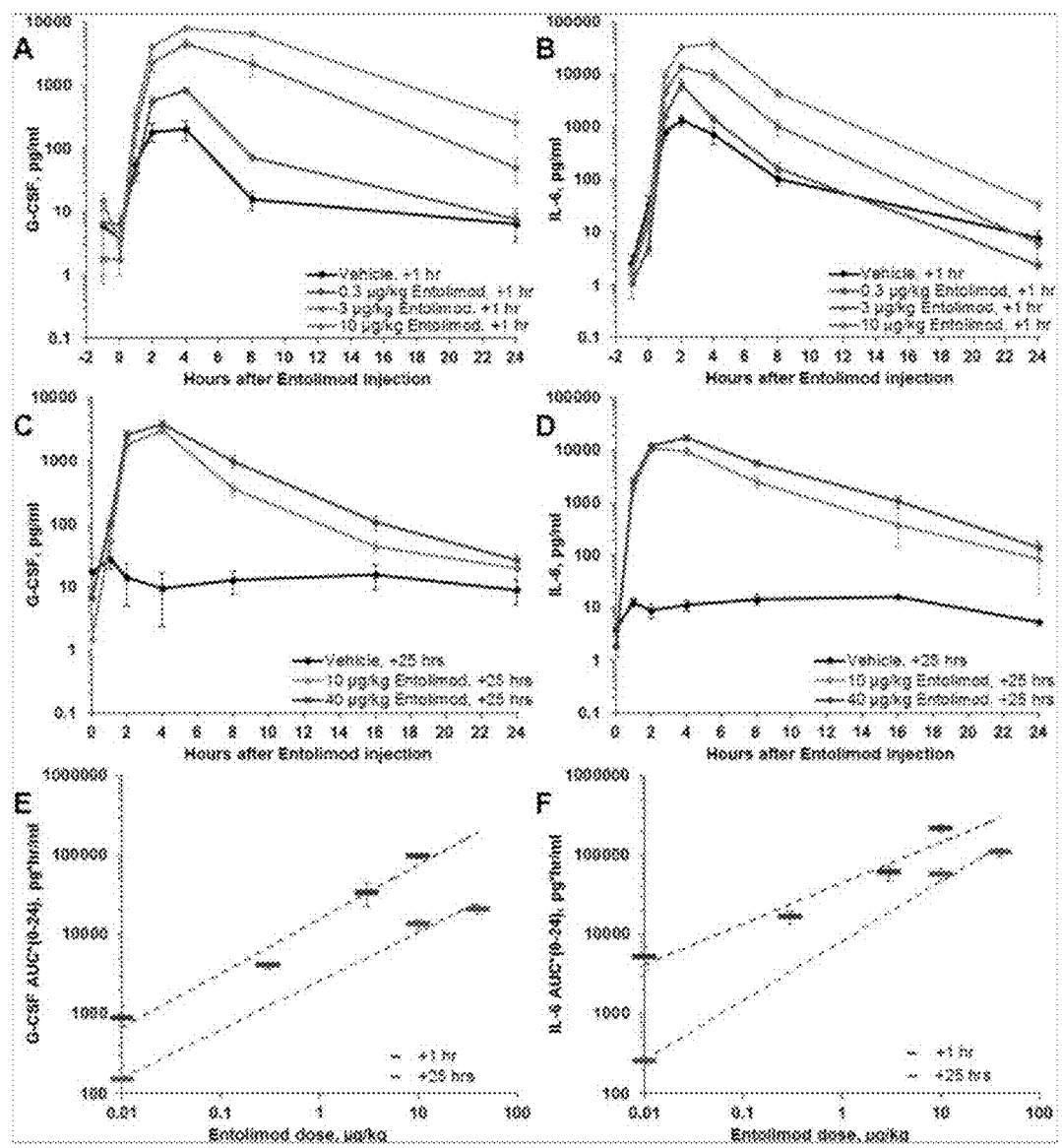
FIG. 12A-F shows the effect of entolimod treatment on G-CSF and IL-6 levels in peripheral blood of irradiated NHPs. Panels A, B: Effect of different entolimod doses administered 1 h after $LD_{50/40}$ TBI (6.75 Gy; study Rs-09; N=18). Panels C, D: Effect of different entolimod doses administered 25 h after $LD_{50/40}$ TBI (6.75 Gy; study Rs-14; N=10). Panels E, F: Comparison of dose-dependence of background-adjusted Area Under the Curve ($AUC_{0-24}$) values for G-CSF and IL-6 after entolimod treatment given 1 h versus 25 h after $LD_{50/40}$ TBI (with dashed log-linear regression lines). Error bars represent standard errors.

Pharmacokinetics and Pharmacodynamic Effects of Entolimod in Lethally Irradiated NHPs In the NHP studies reported here, plasma levels of numerous cytokines were measured at multiple time points following entolimod treatment. G-CSF and IL-6, previously established as potential entolimod efficacy biomarkers, displayed the most substantial and consistent dose-dependent responses to the drug when administered after LD$_{50-75/40}$ TBI doses, with levels peaking on average at 2-4 hours after drug administration (FIG. 12). These results are similar to observations made in non-irradiated NHPs and NHPs irradiated with LD$_{20-30/40}$ TBI doses. Both of these cytokines were induced somewhat by radiation alone (FIGS. 12, A and B); therefore, treatment with entolimod close to TBI (e.g., at 1 hour after TBI) resulted in a combined effect of both treatments on the magnitude of cytokine increase. When entolimod was administered at 25 hours after TBI (after dissipation of radiation-induced G-CSF and IL-6 responses in vehicle-treated animals), entolimod-elicited cytokine profiles were more similar to those seen in non-irradiated animals (FIG. 12, C-F).

Figure 13:
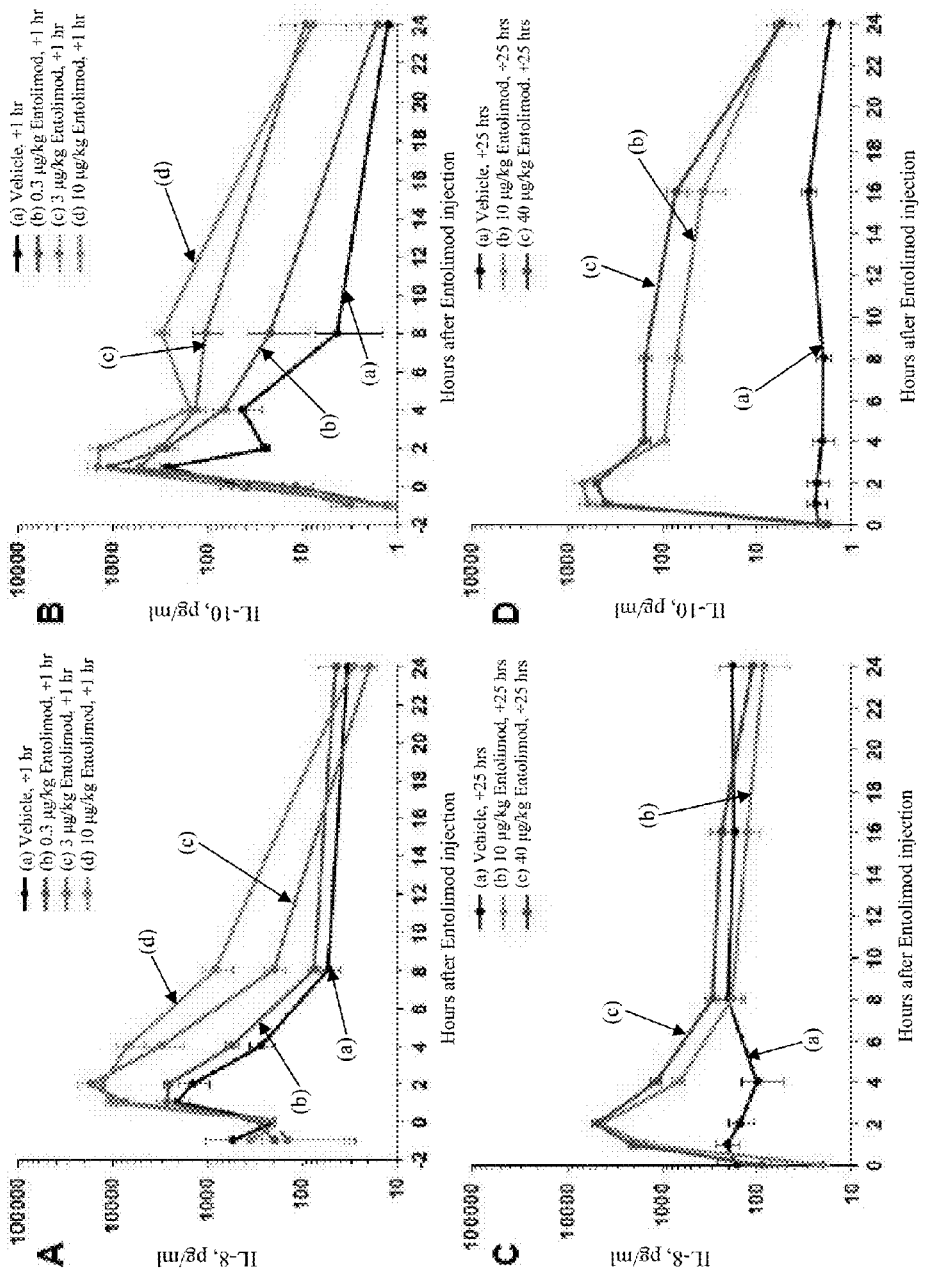
FIG. 13A-D shows the effect of single dose entolimod treatment on IL-8 and IL-10 levels in the peripheral blood of NHPs irradiated with $LD_{50/40}$ or $LD_{75/40}$ doses of TBI. Panels A, B: Effects of different entolimod doses administered 1 h after TBI (study Rs-09; N=18). Panels C, D: Effect of different entolimod doses administered 25 h after TBI (study Rs-14; N=10). Error bars represent standard errors.

Among other cytokines previously shown to be substantially influenced by entolimod in non-irradiated or sublethally irradiated (LD$_{20-30/40}$ TBI) NHPs, IL-8, with neutrophil-mobilizing activity, and IL-10, with anti-inflammatory activity, are also worth mentioning (FIG. 13). Both factors were found to be strongly responsive to entolimod and, to some extent, also to TBI. However, the magnitude of their elevation by entolimod and its dependence on drug dose were less consistent among different studies compared to G-CSF or IL-6. Neither radiation nor entolimod elicited any apparent response in pro-inflammatory cytokines such as IL-2, IP-10, IL-12p70, IL-4, IFNγ, or IL-3.

Figure 14:
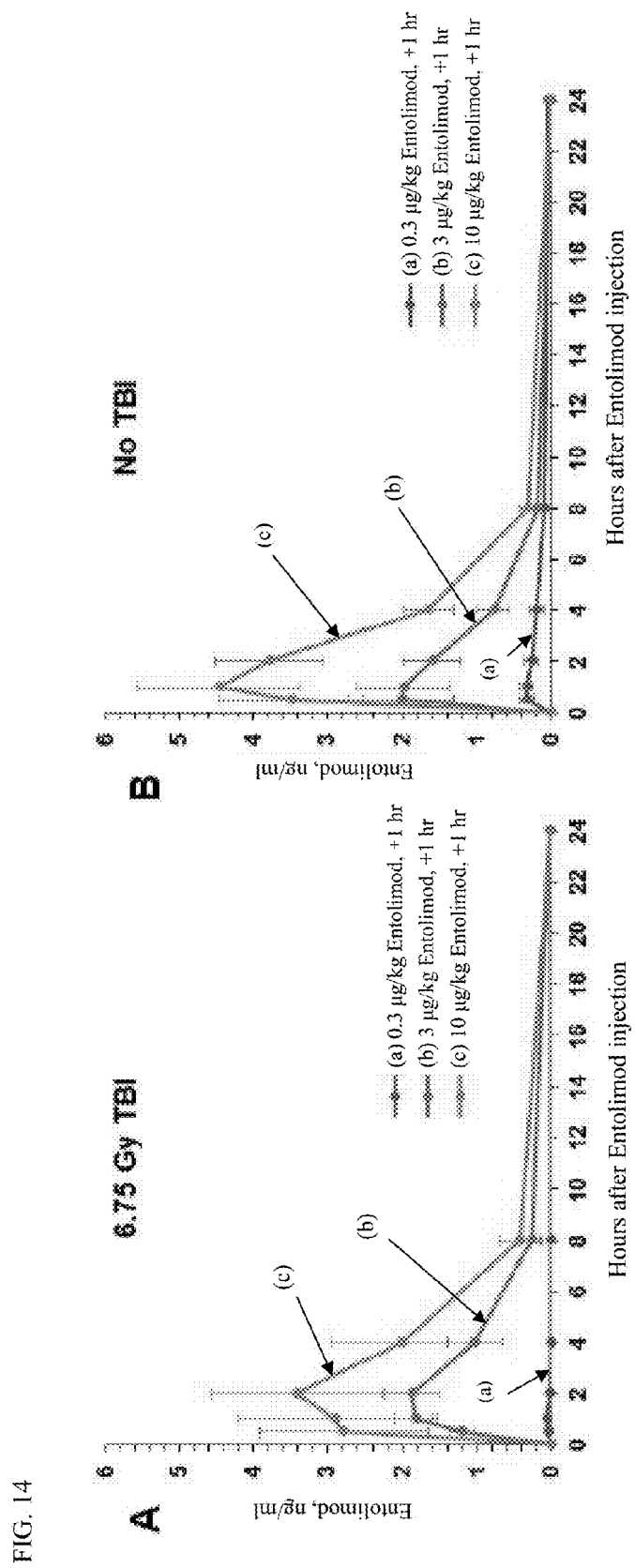
FIG. 14A-B shows entolimod concentrations in the peripheral blood of NHPs (irradiated with $LD_{50/40}$ (6.75 Gy) TBI or non-irradiated) at different times after single intramuscular injection of the indicated drug doses. Panel A: Entolimod levels after injection of different doses 1 h after TBI (study Rs-09; N=18). Panel B: Entolimod levels after injection of the same dose levels in non-irradiated NHPs (study 04-Rs-04; N=6). Error bars represent standard errors.

The pharmacokinetics of entolimod was similar in irradiated and non-irradiated NHPs, with $C_{max}$ and $AUC_{0-24}$ values being very close at identical drug doses. In both irradiated and non-irradiated NHPs, measured concentrations and exposures of entolimod in the blood displayed clear dose dependence (FIG. 14).

Necropsy Findings

Gross pathology findings at necropsy of animals that succumbed to ARS before Day 40 were generally consistent with those expected from ARS pathogenesis and consisted of hemorrhages (of varying extents and degrees of severity, mainly observed in the skin, GI tract, lungs and pericardium), septic complications (mainly in the lungs, pericardium, and skin), and generalized sepsis with multiple organ involvement. Among frequent findings, there were intussusceptions in the small and large intestines, adhesions in the abdominal and thoracic cavities, and signs of lung edema. There were no marked differences in gross pathology findings between entolimod- and vehicle-treated animals. This observation is not unexpected since entolimod treatment did not succeed in mitigating radiation damage in the animals that were necropsied during the course of the study, as evidenced by their mortality. At the same time, NHPs in which entolimod was actually effective (leading to their survival until study termination on Day 40 post-TBI—40-60% of animals at doses 10 µg/kg) could not be assessed for gross pathology status at the time of early recovery from ARS injury.

Gross pathology findings in animals that survived to the end of the study and were euthanized on Day 40-41 post-TBI were minimal regardless of treatment group, indicating that post-ARS recovery was generally complete by that time point. This observation was consistent with the lack of mortality from ARS after day 30 in all study groups.

The results described here demonstrate that entolimod possesses all of the aforementioned desirable properties for an MRC. In fact, when given to NHPs as a single agent (without additional intensive supportive care) via a simple i.m. injection up to 48 hours after TBI, entolimod had a strong and consistent radiomitigative effect in four independent experiments involving 164 NHPs. Overall, entolimod treatment reduced the risk of NHP death 2-3-fold at TBI doses of $LD_{50-75/40}$, providing an absolute survival advantage of 40-60% over vehicle treatment. In two additional studies with a total of 82 NHPs exposed to $LD_{20/40}$-$LD_{30/40}$ TBI doses, single injection of entolimod within at least 48 hours after TBI increased survival by 20-31%: from 69-80% in vehicle-treated control groups to 100% in entolimod-treated groups. Although the magnitude of achievable survival improvement in these latter two studies was limited by low lethality of the TBI doses used, the survival odds ratios were ≥4.75. The NHP studies reported here clearly show that entolimod treatment in the context of lethal TBI leads to reduced damage and accelerated recovery in both the radiosensitive HP and GI systems.

Figure 15:
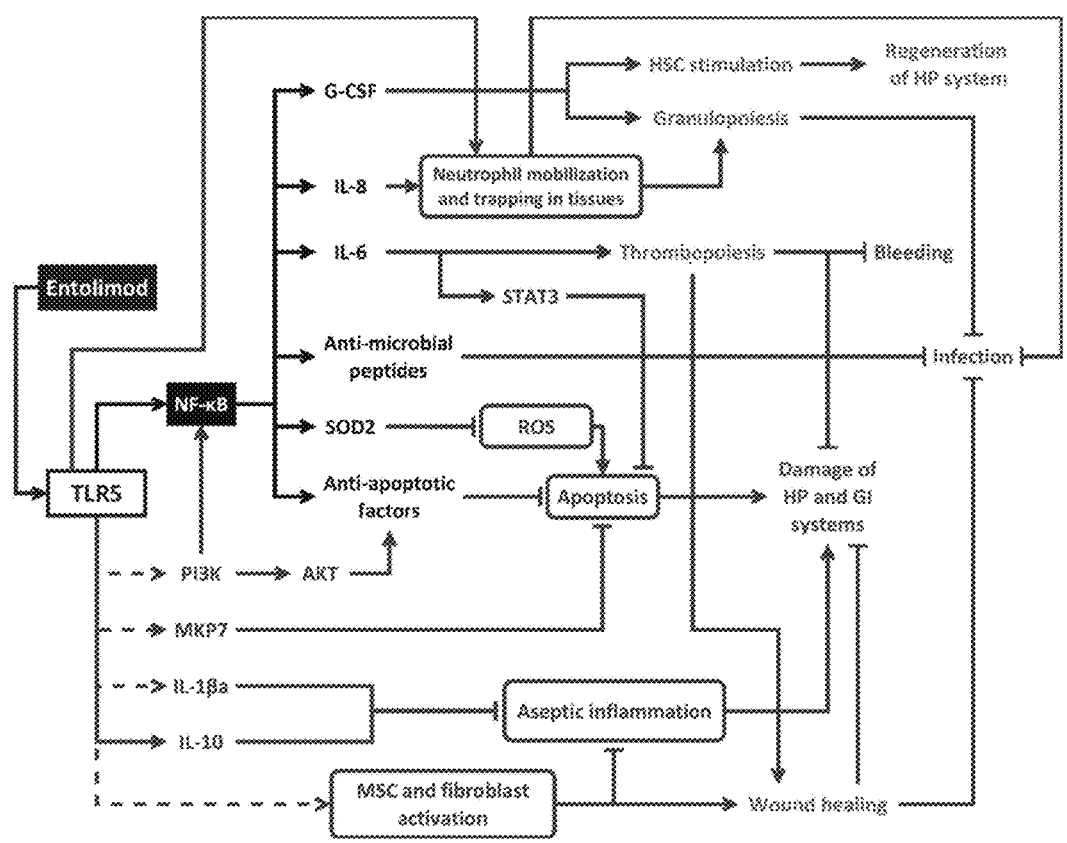
FIG. 15 is, without wishing to be bound by theory, a schematic presentation of mechanism(s) underlying anti-acute radiation syndrome (ARS) effects of entolimod. Entolimod binding to Toll-like receptor 5 (TLR5) initiates a cascade of events, all merging at attenuation of major pathological processes—leading causes of death in ARS: damage to hematopoietic (HP) and gastrointestinal (GI) systems resulting in bleeding and sepsis. The immediate TLR5-dependent effectors include anti-oxidants (e.g., SOD2), anti-apoptotic factors (both NF-κB-dependent (i.e., IAP and Bcl family members), and NF-κB-independent (i.e., PI3K/AKT, MKP7 and STAT3), hematopoietic cytokines (e.g., G-CSF and IL-6), anti-infective factors and processes (e.g., neutrophil mobilization). In addition, stimulation of TLR5 is expected to inhibit radiation-induced aseptic inflammation involved in secondary tissue damage e.g. via induction of an anti-inflammatory cytokine IL-10, IL-1β antagonist (IL-1βa) and stimulation of mesenchymal stem cells (MSC) known to express TLR5 and to have anti-inflammatory properties. Together with fibroblasts that can be induced to proliferate via TLR5 stimulation, MSC may also contribute to wound-healing processes. Dashed lines show all molecular connections downstream of TLR5 that are not directly established for entolimod, but are extrapolated from published data on TLR5-dependent effects of flagellin.

Binding of entolimod to TLR5 results in stimulation of a number of downstream pathways, including those regulated by the key TLR5-activated transcription factor, NF-κB. Ultimately, as shown in the non-limiting model in FIG. 15, this engages multiple mechanisms of action against the multi-faceted toxic effects of ionizing radiation.

Without wishing to be bound by theory, one of these mechanisms appears to be neutralization of radiation-triggered reactive oxygen species (ROS) by the enzyme superoxide dismutase (SOD2), which is strongly induced by entolimod in both mouse and NHP models of ARS. Another mechanism that is a likely contributor to entolimod's radio-protective and radiomitigative effects, without wishing to be bound by theory, is inhibition of radiation-induced apoptosis, which is well-recognized as a major cause of the tissue damage and cytopenias observed in ARS. Anti-apoptotic effects of entolimod are likely mediated via induction of NF-κB and its downstream anti-apoptotic effectors, such as members of the IAP and Bcl-2 protein families. Additional anti-apoptotic mechanisms of entolimod may include direct activation of the PI3K pathway and of a specific anti-apoptotic phosphatase, MKP7, recently identified as an inhibitor of radiation-dependent GI cell apoptosis, both triggered by flagellin stimulation of TLR5. Entolimod was shown to reduce radiation-induced apoptosis of cells in GI tissues both in mice and NHPs. It may also attenuate apoptosis of other types of cells relevant to development of ARS such as inhibition of neutrophil apoptosis. In addition, stimulation of TLR5 is expected to inhibit radiation-induced aseptic inflammation involved in secondary apoptotic tissue damage e.g. via induction of an anti-inflammatory cytokine IL-10, IL-1β antagonist (IL-1βa) and stimulation of mesenchymal stem cells (MSC) known to express TLR5 and to have anti-inflammatory properties.

Restoration of the integrity and functionality of damaged organs following irradiation depends on the availability of sufficient numbers of undamaged tissue stem cells. The ability to protect and stimulate stem cells is expected to be an important property of any effective radiomitigator. This study demonstrated protective and stimulatory effects of entolimod on stem cells in both HP and GI tissues. Entolimod-treated irradiated NHPs displayed increased clonogenic potential of the BM and improved survival of intestinal-crypt stem cells as indicated by robust and accelerated crypt proliferation. The beneficial effects of entolimod on HP and GI stem cells are translated into facilitation of morphological recovery of the corresponding tissues. Without wishing to be bound by theory, it is believed that the mechanism(s) underlying entolimod's stimulatory effects on stem cells are likely mediated by induced cytokines, some of which are known to possess this activity. Among the cytokines elevated in response to entolimod, two hematopoietic cytokines, G-CSF and IL-6, consistently showed the strongest induction. The importance of these cytokines for the radiomitigative activity of entolimod has been proven experimentally in vivo using neutralizing antibodies and is fully consistent with their defined biological activities as stimulators of granulo- and thrombopoiesis, respectively. Consequently, both the severity and duration of radiation-induced thrombocytopenia and neutropenia were significantly reduced in entolimod-treated NHPs. Entolimod's promotion of red blood cell lineage recovery (reticulocytes) with kinetics and magnitude similar to its effects on thrombocytopenia may be suggestive of stimulation of megakaryocyte/erythrocyte-restricted progenitors (MEPs). The combined effects of entolimod on reducing the severity and duration of thrombocytopenia, and accelerating recovery of the erythroid lineage result in markedly diminished incidence of life-threatening Grade 4 hemorrhagic anemia, one of the hallmarks of HP ARS.

Loss of tissue integrity due to TBI leads to development of wounds and septic complications, which are especially dangerous on the background of impaired tissue repair and immunosuppression. Anti-infective properties reported for flagellin (and likely also relevant for entolimod due to its similar mechanism of action) are consistent with its general role as a trigger of TLR5-mediated innate immune response to bacterial infection. Indeed, flagellin was shown to induce secretion of antimicrobial factors, such as IL-17, S100A8/S100A9, hepcidin and other small peptides with antimicrobial activity, to support anti-infective defenses and tissue repair in the lungs, gut, skin and cornea. Direct anti-bacterial activity of flagellin (or a flagellin variant with a structure similar to that of entolimod) has been demonstrated in animal infection models. This activity was likely associated with the ability of flagellin/entolimod to elicit early neutrophil mobilization (observed even in irradiated NHPs within 24 hours following entolimod treatment—see FIGS. 4, C and D; and FIGS. 5, C and D) followed by neutrophil infiltration into tissues where they play an important role in local antibacterial responses. Mobilization and tissue deposition of neutrophils (especially in the lung and the liver) can be explained by both entolimod-dependent induction of IL-8 and by entolimod's direct action on TLR5 expressed on the surface of neutrophils. TLR5 activation also enhances the phagocytic capacity and the respiratory burst activity of airway neutrophils, which likely contributes to their antibacterial potency. At later times in the course of ARS, entolimod-induced accelerated recovery from radiation cytopenias would also be expected to contribute to antibacterial immunity (via restored granulocyte/macrophage function) and wound healing (via restored blood clotting and tissue trophic function of platelets). Another mechanism through which entolimod may promote wound healing, without wishing to be bound by theory, is direct stimulation of fibroblasts and MSC.

Example 3: Dosing of CBLB502 is Safe in Humans

A clinical trial to assess that, in healthy human subjects, the proposed dosing regimen of CBLB502 is safe is undertaken. CBLB502 or placebo is administered to human subjects on a weight-adjusted basis within specific ranges of body weights to 1) describe the safety profile of the drug using this regimen, and 2) assess the PD effects of the drug on relevant biomarkers (in particular G-CSF, IL-6, and fold-change in ANC) using this regimen.

Trial subjects are healthy adult male and non-pregnant female subjects 18 years. Healthy subjects are considered a relevant population because the majority of the victims of a radiological event will have been healthy individuals prior to IR exposure. Subjects are enrolled in strata based on body weight and randomized in a 6:1 ratio to receive a single IM injection of CBLB502 or placebo according to the following Table 13:

TABLE 13

Dose Intervals Designed to Ensure Body-Weight-Adjusted Dosing within Range of 0.40-0.60 µg/kg

| Vial Size, µg 35 | | | | | | Body-Weight-Adjusted Dose, µg/kg | |
|---|---|---|---|---|---|---|---|
| Vial Amount, µL | Absolute Dose, µg | Body Weight, kg | | Body Weight, lb | | At Minimum Weight | At Maximum Weight |
| | | Minimum | Maximum | Minimum | Maximum | | |
| 20 | 2 | 4 | 5 | 9 | 11 | 0.50 | 0.40 |
| 30 | 3 | 6 | 8 | 13 | 17 | 0.50 | 0.40 |
| 50 | 5 | 9 | 13 | 19 | 28 | 0.59 | 0.40 |
| 80 | 8 | 14 | 20 | 30 | 44 | 0.59 | 0.40 |
| 120 | 12 | 21 | 30 | 46 | 66 | 0.57 | 0.40 |
| 130 | 13 | 31 | 33 | 68 | 72 | 0.42 | 0.40 |
| 200 | 20 | 34 | 50 | 74 | 110 | 0.60 | 0.40 |
| 300 | 30 | 51 | 75 | 112 | 165 | 0.59 | 0.40 |
| 450 | 45 | 76 | 113 | 167 | 248 | 0.59 | 0.40 |
| 450 | 45 | >114 | ∞ | >250 | ∞ | 0.40 | <0.40 |

The study is performed at a specialized inpatient clinic located in the US that is experienced in the conduct of trials in healthy subjects. Subjects undergo screening medical history, physical examination, vital signs, laboratory evaluation, and electrocardiogram (ECG) assessments. Subjects are administered CBLB502 or placebo IM in the morning of Day 1 and then observed as inpatients for ≥36 hours. Types of adverse events are coded using the standard Medical Dictionary for Regulatory Activities (MedDRA) and severity is graded using the Common Terminology Criteria for Adverse Events (CTCAE), Version 4.03. Adverse event frequency, timing of onset duration and relationship to study therapy is also recorded. Laboratory abnormalities are recorded. To describe hemodynamic changes that are expected with administration of a TLR agonist, supine and sitting blood pressures is assessed predose, hourly for 12 hours postdose, and then every 4 hours through 36 hours postdose. ECGs, clinical chemistry and hematology data, and plasma for cytokines—including G-CSF, IL-6, as well as ILs-1α, -1β, -2, -8, -10, -12, tumor necrosis factor-α, interferon (IFN)-β and IFN-γ, is obtained predose and at 1, 2, 4, 8, 12, 24 hours postdose to fully describe the CBLB502 safety, PD, and inflammatory profiles. Serum nitrate levels obtained at the same time points may offer correlates to changes in blood pressure. Subjects undergo follow-up at Days 8 and 29 for assessment of vital signs, ECGs, safety, PD parameters, and anti-CBLB502 antibodies. The sample size for the study provides a large statistical sample (i.e., ≥30 subjects) for each dosing regimen. Subject characteristics and study results are described by dosing group using tabular and graphical methods to support CBLB502 product labeling.

Example 4: CBLB502 can Reduce the Risk of Death Following not Only LD70, but Also LD30 and LD50 Doses of Total Body Irradiation (TBI)

Studies are undertaken to provide statistically robust data on the efficacy of CBLB502 in non-human primates (NHPs)

over an LD30-50 range of TBI doses. These radiation doses will be used to complement prior pivotal efficacy study performed at LD70/60 and provide efficacy testing at LD30, LD50, and LD70 TBI doses. Four groups of NHPs (~$_{1:1}$ male:female ratio) receive a single dose of TBI: $LD_{30/60}$ (Groups 1, 2: 36 animals/group) or $LD_{50/60}$ (Groups 3, 4: 30 animals/group), followed 25 hours later with a single IM injection of vehicle (Groups 1, 3) or the animal doses of CBLB502 of 10 μg/kg (Groups 2, 4). The study is randomized, blinded, and placebo-controlled. 60-day survival is the primary endpoint. The sample sizes (N=36 for LD30, N=30 for LD50 TBI levels) provide power >0.95 ($\alpha$=0.05, 2-sided, Cochran-Mantel-Haenszel test) to detect an CBLB502 60-day survival benefit. These sizes also provide a power of 0.80 for descriptive comparisons of the proportions of survivors at each TBI level ($\alpha$=0.05, 2-sided, Fisher's exact test). PK and PD effects on biomarkers and blood counts are evaluated secondarily. This study also looks for correlations between biomarker and hematopoietic responses to drug and the time dependence of efficacy. This study is performed under GLP with elements of GCP, including blinding, randomization, and pre-specified statistical plan. All PD and PK measurements are obtained using GLP-validated assays.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

---

What is claimed is:

1. A method of treating acute radiation syndrome (ARS) in a human patient, the method comprising administering to the human patient not more than a single dose of an effective amount of a composition comprising entolimod, wherein the effective amount is about 0.4 to about 0.6 µg/kg, and wherein the entolimod comprises the amino acid sequence of SEQ ID NO: 1.

2. The method of claim 1, wherein the ARS is a result of a high dose of radiation of about 5 to about 30 Gy.

3. The method of claim 1, wherein the high dose of radiation is sufficient for a classification of Unit Radiation Exposure Status of RES 3.

4. The method of claim 1, wherein the human patient is administered entolimod within about 48 hours of being exposed to radiation.

5. The method of claim 1, wherein the human patient is administered entolimod within one or more of the triage, emergency care, and definitive care stages of radiation exposure.

6. The method of claim 1, wherein entolimod is administered parenterally or orally.

7. The method of claim 1, wherein entolimod is administered by a single intramuscular injection.

8. The method of claim 1, wherein entolimod is administered by controlled-release or sustained-release.

9. The method of claim 1, wherein the ARS comprises one or more of gastrointestinal syndrome; hematopoietic syndrome; neurovascular syndrome; and apoptosis-mediated tissue damage.

10. The method of claim 1, wherein the human patient presents a lymphocyte count reduction of about 50% within about 24 to about 48 hours of being exposed to radiation.

11. The method of claim 1, wherein the human patient's lymphocyte count is less than about 1000/pL.

12. The method of claim 1, wherein the treatment with entolimod is used as an adjuvant or neoadjuvant to one or more of blood products, colony stimulating factors, cytokines and/or growth factors, antibiotics, diluting and/or blocking agents, mobilizing or chelating agents, stem cell transplants, antioxidants or free radicals, and radioprotectants.

13. The method of claim 1, wherein entolimod induces expression of NF-κB through toll-like receptor (TLR)-mediated activation.

* * * * *